(12) United States Patent
Lev et al.

(10) Patent No.: US 11,549,956 B2
(45) Date of Patent: Jan. 10, 2023

(54) ASSAY SYSTEM INCLUDING ASSAY APPARATUS AND HANDHELD SINGLE USE ASSAY DEVICES FOR USE THEREWITH

(71) Applicant: Gyntools Ltd, Jerusalem (IL)

(72) Inventors: Nimrod Lev, Savion (IL); Menachem Lev-Sagie, Lapid (IL); Tal Shlomovitz, Tel Aviv (IL); Zohar Horowitz Limor, Even Yehuda (IL)

(73) Assignee: GYNTOOLS LTD, Jerusalem (IL)

( * ) Notice: Subject to any disclaimer, the term of this patent is extended or adjusted under 35 U.S.C. 154(b) by 0 days.

(21) Appl. No.: 17/769,264

(22) PCT Filed: Oct. 27, 2020

(86) PCT No.: PCT/IL2020/051116
§ 371 (c)(1),
(2) Date: Apr. 14, 2022

(87) PCT Pub. No.: WO2021/084528
PCT Pub. Date: May 6, 2021

(65) Prior Publication Data
US 2022/0357350 A1 Nov. 10, 2022

(30) Foreign Application Priority Data
Oct. 30, 2019 (IL) .......................................... 270300

(51) Int. Cl.
*G01N 35/00* (2006.01)
*G01N 35/10* (2006.01)
(Continued)

(52) U.S. Cl.
CPC ....... *G01N 35/00029* (2013.01); *G01N 1/312* (2013.01); *G01N 35/1002* (2013.01);
(Continued)

(58) Field of Classification Search
None
See application file for complete search history.

(56) References Cited

U.S. PATENT DOCUMENTS

| 4,190,314 A | 2/1980 | Goldsmith |
| 5,428,470 A | 6/1995 | Labriola, II |

(Continued)

FOREIGN PATENT DOCUMENTS

| AU | 2005240757 B2 | 2/2011 |
| KR | 20140140068 A | 12/2014 |

(Continued)

OTHER PUBLICATIONS

Extended Supplementary Search Report dated Feb. 18, 2021 in EP Application No. 18819634.9.

(Continued)

*Primary Examiner* — Jyoti Nagpaul
(74) *Attorney, Agent, or Firm* — Panitch Schwarze Belisario & Nadel LLP

(57) ABSTRACT

Assay system including assay apparatus and handheld single use assay devices for ElectroMagnetic Radiation (EMR) examination of a specimen. The assay devices include a housing, a specimen slide for elevation from an initial lowermost specimen introduction position to a final uppermost specimen examination position and a built-in liquid reagent dispensing arrangement for dispensing liquid reagent on the specimen slide. The assay apparatus automatically actuates an assay device and includes an imaging arrangement for obtaining specimen images.

17 Claims, 33 Drawing Sheets

(51) Int. Cl.
*G01N 1/31* (2006.01)
*G01N 1/02* (2006.01)

(52) U.S. Cl.
CPC .......... *G01N 2001/028* (2013.01); *G01N 2035/00138* (2013.01)

(56) References Cited

U.S. PATENT DOCUMENTS

| | | | |
|---|---|---|---|
| 5,760,315 | A | 6/1998 | Verheijden et al. |
| 6,170,318 | B1 | 1/2001 | Lewis |
| 6,316,205 | B1 | 11/2001 | Guan et al. |
| 7,434,986 | B2 | 10/2008 | Ignatowicz |
| 7,434,988 | B1 | 10/2008 | Kychakoff et al. |
| 8,371,182 | B1 | 2/2013 | Israelachvili |
| 9,222,935 | B1 * | 12/2015 | Bransky .............. F04B 9/042 |
| 9,265,580 | B2 | 2/2016 | Speck et al. |
| 9,518,920 | B2 | 12/2016 | Fine et al. |
| 2002/0182739 | A1 | 12/2002 | Sadik et al. |
| 2007/0202564 | A1 | 8/2007 | Glasson et al. |
| 2008/0188769 | A1 | 8/2008 | Lu |
| 2009/0030342 | A1 | 1/2009 | Flanigan et al. |
| 2011/0021950 | A1 | 1/2011 | Daniels |
| 2012/0031605 | A1 | 2/2012 | Takayama et al. |
| 2012/0157878 | A1 | 6/2012 | Mendez |
| 2012/0288890 | A1 | 11/2012 | Oouchi |
| 2013/0211288 | A1 | 8/2013 | Zwart |
| 2013/0338533 | A1 | 12/2013 | Olsen |
| 2015/0004717 | A1 | 1/2015 | McDevitt et al. |
| 2015/0094219 | A1 | 4/2015 | Trowell et al. |
| 2016/0186240 | A1 | 6/2016 | Andreyev et al. |
| 2017/0209865 | A1 | 7/2017 | Carrano et al. |
| 2018/0070928 | A1 | 3/2018 | Jones et al. |
| 2019/0120727 | A1 | 4/2019 | Harding et al. |
| 2019/0233888 | A1 | 8/2019 | Wunderle et al. |
| 2020/0132703 | A1 | 4/2020 | Lev-Sagie et al. |

FOREIGN PATENT DOCUMENTS

| | | |
|---|---|---|
| WO | 2005108604 A2 | 11/2005 |
| WO | 2012033796 A2 | 3/2012 |
| WO | 2013078014 A1 | 5/2013 |
| WO | 2013134179 A2 | 9/2013 |
| WO | 2017001922 A1 | 1/2017 |
| WO | 2018235073 A1 | 12/2018 |

OTHER PUBLICATIONS

Intl Search Report and Written Opinion dated Feb. 11, 2021 in Intl Application No. PCT/IL2020/051116.

* cited by examiner

ASSAY SYSTEM INCLUDING ASSAY APPARATUS AND HANDHELD SINGLE USE ASSAY DEVICES FOR USE THEREWITH

CROSS-REFERENCE TO RELATED APPLICATIONS

This application is a Section 371 of International Application No. PCT/IL2020/051116, filed Oct. 27, 2020, which was published in the English language on May 6, 2021, under International Publication No. WO 2021/084528 A1, which claims priority under 35 U.S.C. § 119(b) to Israeli Application No. 270300, filed Oct. 30, 2019, the disclosures of each of which are incorporated herein by reference.

FIELD OF THE INVENTION

This invention relates to assay systems including assay apparatus and handheld assay devices for use therewith.

BACKGROUND OF THE INVENTION

Commonly owned PCT International Application No. PCT/IL2018/050671 entitled Assay Devices and Assay Apparatus for Use Therewith published as PCT International Publication No. WO 2018/235073 A1 discloses assay devices for EMR examination of a specimen along one or more lines of examination through the assay devices. The assay devices include a housing having a specimen slide for placing a bodily specimen thereon. The specimen slide is designed to be urged from a lowermost specimen introduction position to an uppermost specimen examination specimen in which the specimen slide presses the bodily specimen against the housing top face's underside. A bodily specimen is preferably reacted with one or more liquid reagents, for example, saline, potassium hydroxide, and the like, after being placed onto a specimen slide before examination. A pH detection surface is also preferably smeared with a bodily specimen for providing a pH reading for diagnostic purposes.

There is a need for assay systems for diagnostic purposes of bodily specimens.

SUMMARY OF THE INVENTION

The present invention is directed towards assay systems for diagnostic purposes of bodily specimens. The assay systems include single use handheld assay devices for each preparing a bodily specimen for diagnostic purposes and assay apparatus for use with interchangeable assay devices for acquiring diagnostic information of bodily specimens for diagnostic purposes. The handheld assay devices are each intended for use with a single use handheld specimen collection tool including a handle and a specimen collection tip for obtaining a bodily specimen from a bodily orifice or an exposed bodily surface. Bodily orifices include inter alia facial orifices, urethra, rectum, and vagina. Exposed bodily surfaces include inter alia a skin eruption, a skin efflorescence, an open wound, lips, eyes, and the like. The handheld assay devices can be pre-assembled with a handheld specimen collection tool or alternatively a handheld specimen collection tool can be provided separately.

The assay devices include a longitudinal assay device centerline and a generally box-shaped cartridge housing having a specimen slide with preferably two or more spatially discrete work surfaces disposed along the longitudinal assay device centerline. The work surfaces are preferably smeared with bodily specimen on sliding withdrawal of a specimen collection tool through an assay device. The work surfaces preferably include a pH detection surface for providing a pH reading.

The assay devices include a built-in liquid reagent dispensing arrangement for dispensing at least one liquid reagent onto a bodily specimen smeared onto a work surface. The built-in liquid reagent dispensing arrangement includes a barrel, a leading seal, a trailing seal member, liquid reagent between the leading seal and the trailing seal member and a liquid reagent dispensing port for dispensing liquid reagent for per working surface. The leading seal is displaced along its barrel by a plunger from a pre-liquid reagent dispensing position to a liquid reagent dispensing position. The built-in liquid reagent dispensing arrangement can include different trailing seal members. One trailing seal member is intended to be displaced along a barrel from a pre-liquid reagent dispensing position in front of its liquid reagent dispensing port to a liquid reagent dispensing position beyond its liquid reagent dispensing port. Another trailing seal member is a stopcock permanently deployed at its liquid reagent dispensing port and intended to be rotated from a closed position to an open position for dispensing purposes. The built-in liquid reagent dispensing arrangement can be designed to dispense different liquid reagents on bodily specimens smeared onto two or more spatially discrete work surfaces such that the liquid reagents don't cross react. The built-in liquid reagent dispensing arrangement can be designed to dispense different liquid reagent volumes either by adjusting the distance between a leading seal member and a trailing seal member or adjusting a plunger's length.

The assay devices are required to undergo two actuations after bodily specimen smearing in order to be ready for examination of their bodily specimen for diagnostic purposes as follows: First, actuation of their built-in liquid reagent dispensing arrangement. And second, linear elevation of their specimen slides from their lowermost specimen introduction position to their uppermost specimen examination specimen. Specimen slide elevation can occur concurrently with or after liquid reagent dispensing on the condition that liquid reagent dispensing ends before specimen slide elevation ends.

The assay apparatus includes a tray with a tray pocket for interchangeably receiving an assay device in which a bodily specimen has been preferably smeared onto its specimen slide. The assay apparatus includes one or more plungers for actuating a handheld assay device's built-in liquid reagent dispensing arrangement and one or more specimen slide elevation members for elevating a handheld assay device's specimen slide through its cartridge housing bottom face from its lowermost specimen introduction position to its uppermost specimen examination position. The assay apparatus preferably includes a single electric motor with mechanical arrangements for actuating an assay device's built-in liquid reagent dispensing arrangement and elevating its specimen slide. Alternatively, assay apparatus can include electro-mechanical means, for example, small electric motors, solenoids, and the like, for actuating an assay device's built-in liquid reagent dispensing arrangement and elevating its specimen slide. The assay apparatus preferably includes one or more micro-switches for ensuring that a newly inserted assay device is correctly inserted in its tray pocket. The assay apparatus preferably includes a used assay device detector for detecting a previously used assay device for rejecting same.

Assay apparatus preferably includes two or more optical paths with different magnifications as follows: A first optical path with no magnification and a second optical path having ×10 to ×1000 magnification. The first optical path can be used for acquiring low resolution images, for example, a target image, a pH reading image, and the like. The second optical path can be used for acquiring, for example, high resolution microscope images of bodily specimens along a preferably linear scan path. Assay apparatus preferably includes focusing along the second optical path for accurately focusing on a bodily specimen. Assay apparatus can initially acquire images along the first optical path and subsequently the second optical path or vice versa. Alternatively, assay apparatus can simultaneously acquire images along both the first optical path and the second optical path.

The assay apparatus can include two digital image cameras for acquiring first optical path images and second optical path images. Alternatively, the assay apparatus can preferably include a single digital image camera for acquiring first optical path images and second optical path images. In the latter case, the assay apparatus necessarily requires a dual optical path structure having a shutter arrangement for selectively opening and closing a first optical path for obtaining first optical path images and correspondingly closing and opening a second optical path for obtaining second optical path images such that the single digital image camera acquires first optical path images on opening the first optical path and closing the second optical path and second optical path images on closing the first optical path and opening the second optical path.

The one or more digital image camera can operate at different EMR spectrum including inter alia visual spectrum, IR spectrum, UV spectrum and the like. Accordingly, the assay apparatus can include different illumination sources for illuminating an assay device at different predetermined EMR spectrum. Illumination sources can illuminate an assay device from different directions. Illumination sources can be associated with one or more specific optical paths. Some digital images, for example, of pH readings are necessarily color images in the visual spectrum. Some microscope images are also preferably color images in the visual spectrum. The microscope images and/or video scans of bodily specimen are preferably acquired at between 30 to 60 frames per second (FPS) to avoid camera blur during motion or at a lower rate when an assay device is moved slowly inside an assay apparatus.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF DRAWINGS

WO 2018/235073 Assay Devices and Assay Apparatus for Use Therewith

Figure 1:
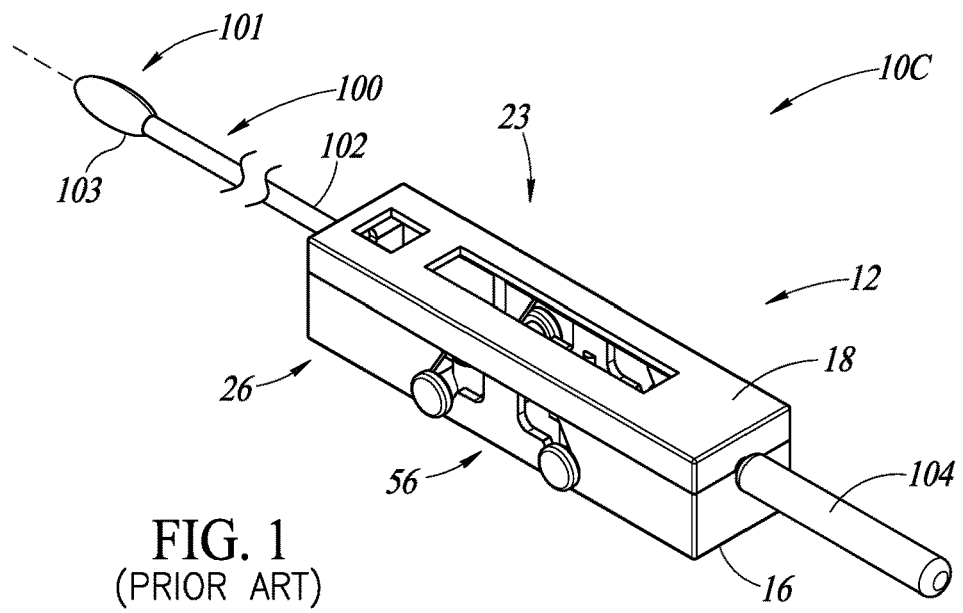
FIG. 1 corresponds to WO 2018/235073 A1's FIG. 11.
Figure 4:
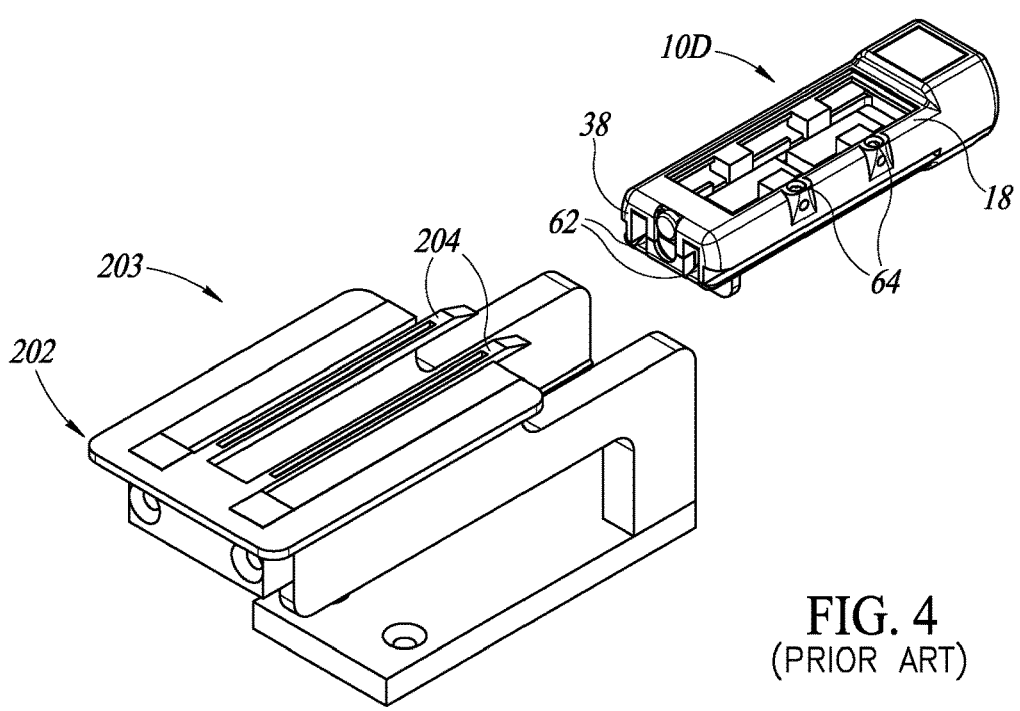
FIG. 4 corresponds to WO 2018/235073 A1's FIG. 19.

Prior art FIG. 1 to prior art FIG. 4 correspond to commonly owned WO 2018/235073 A1's FIG. 11, FIG. 12, FIG. 18 and FIG. 19. Prior art FIG. 1 to prior art FIG. 4 show WO 2018/235073 reference numbers.

Figure 2:
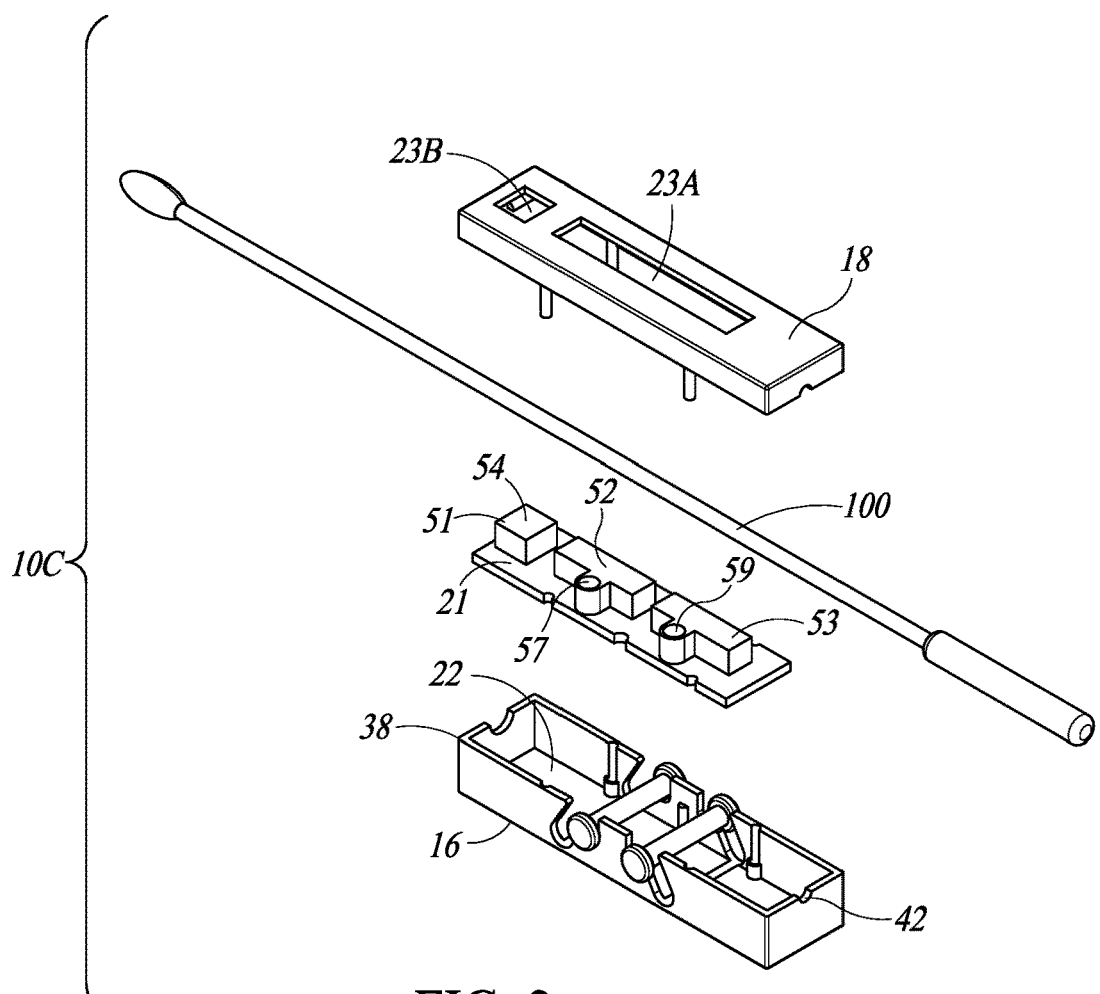
FIG. 2 corresponds to WO 2018/235073 A1's FIG. 12.

FIG. 1 and FIG. 2 disclose an assay device 10C and a specimen handling tool 100. The assay device 10C includes a box-like housing 12 having a housing bottom face 16 and a housing top face 18. The housing bottom face 16 has a transparent housing bottom face panel 22. The housing top face 18 has a transparent housing top face panel 23 in registration with the transparent housing bottom face panel 22. The transparent housing top face panel 23 includes sub-panels 23A and 23B. The assay device 10C includes a specimen slide 21 including three work surfaces: a leading work surface 51 having a pH detection surface 54 for indicating a bodily specimen's pH value, a central work surface 52 and a trailing work surface 53. The leading work surface 51, the central work surface 52 and the trailing work surface 53 are spatially discrete to avoid cross contamination.

The specimen handling tool 100 has a leading specimen collection end 101, a shank 102, a swab end 103 and a trailing handle 104. The specimen handling tool 100 is longer than the box-like housing 12 such that its leading swab end 103 extends therebeyond in one direction and its handle 104 extends therebeyond in the opposite direction. The assay device 10C is preferably pre-assembled with the specimen handling tool 100 such that pursuant to obtaining a bodily specimen on its leading swab end 103, pulling the specimen handling tool 100 through the assay device 10C smears bodily specimen on the three work surfaces 51, 52 and 53.

The assay device 10C includes a manually operated specimen slide elevation arrangement 26 for elevating the specimen slide 21 from its lowermost specimen introduction position to its uppermost specimen examination position in which the work surfaces 51, 52 and 53 are juxtaposed against the housing top face panel 23's underside. The assay device 10C includes an integral liquid reagent pump arrangement 56 with a central liquid reagent reservoir 57 and a trailing liquid reagent reservoir 59. The integral liquid reagent pump arrangement 56 automatically dispenses liquid reagents from the central liquid reagent reservoir 57 and the trailing liquid reagent reservoir 59 correspondingly on the central work surface 52's bodily specimen and the trailing work surface 53's bodily specimen on manual operation of the specimen slide elevation arrangement 26.

The transparent housing bottom face panel 22, the transparent housing top face panel 23 and the specimen slide 21 are transparent at one or more predetermined EMR spectrum including inter alia visual spectrum, IR spectrum, UV spectrum and the like. Accordingly, in the uppermost specimen examination position, the assay device 10C has a line of examination for examining the pH detection surface 54 and two lines of examination for examining the bodily specimens on the central work surface 52 and the trailing work surface 53.

Figure 3:
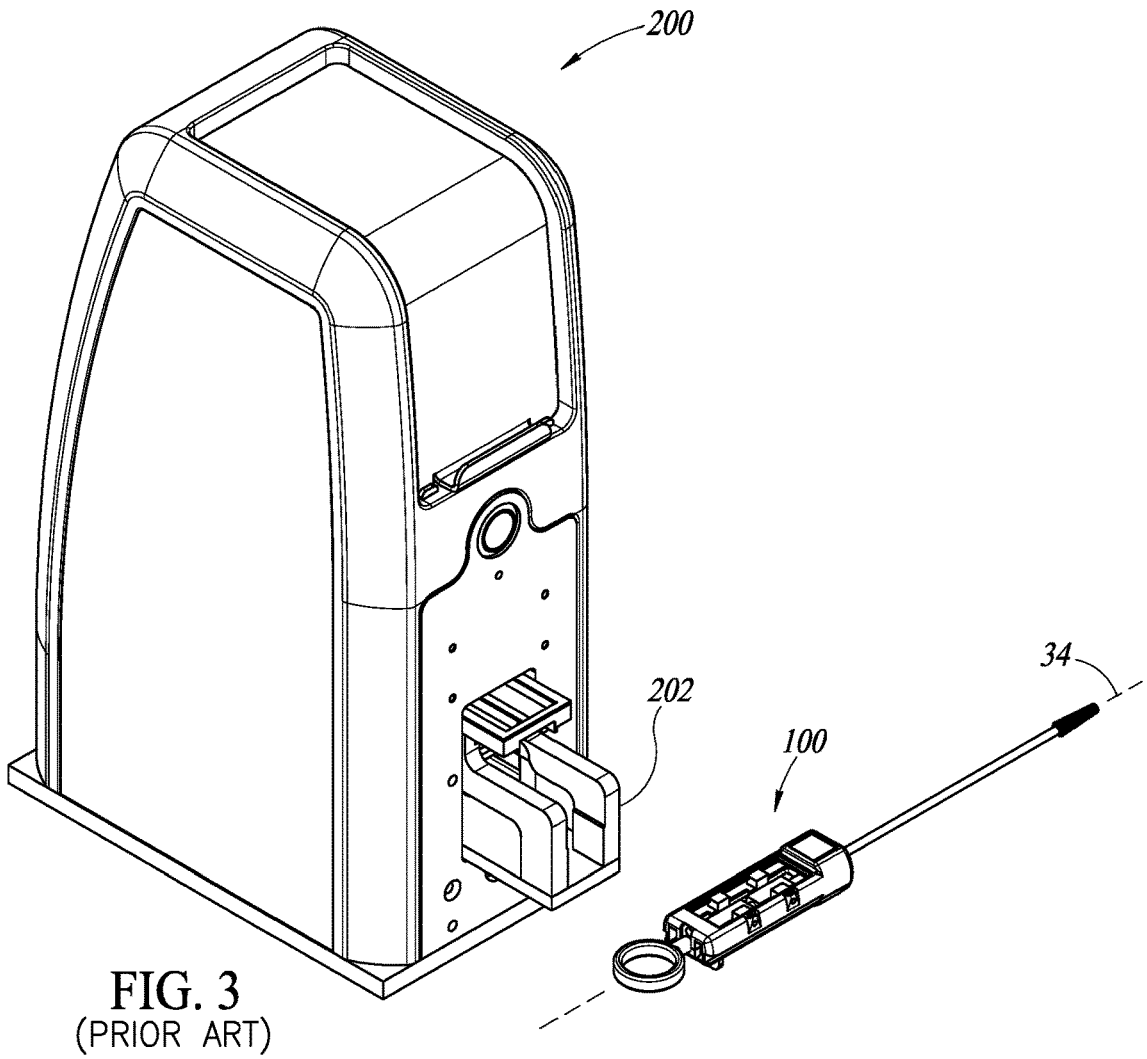
FIG. 3 corresponds to WO 2018/235073 A1's FIG. 18.

FIG. 3 and FIG. 4 disclose an assay device 10D for use with assay apparatus 200 typically in the form of a digital microscope. The assay device 10D has a longitudinal assay device centerline 34 and a leading minor end face 38. The assay device 10D includes a liquid reagent injection port pair 64 in its housing top face 18 for manual injection of liquid reagent onto its work surfaces. The leading minor end face 38 includes a slot pair 62 spaced apart across its width and under its specimen slide 21 in its initial lowermost specimen introduction position.

The assay apparatus 200 includes an assay device tray 202 reciprocal between WO 2018/235073 FIG. 18's assay device access position and WO 2018/235073 FIG. 21's assay device examination position. The assay device tray 202 includes a specimen slide elevation member 203 for sliding insertion through the slot pair 62 into the assay device 10D along its longitudinal assay device centerline 34 for urging its specimen slide 21 from its lowermost specimen introduction position to its uppermost specimen examination position after injection of liquid reagents. The specimen slide elevation member 203 is preferably forked shape with spaced apart elevation prongs 204 which do not obstruct lines of examination through the assay device 10D. The assay apparatus 200 can be a standalone device with built-in information collection and diagnosis capabilities for examining a bodily specimen. Alternatively, assay apparatus 200 can transmit acquired images and other information from a bodily specimen for remote processing.

Assay System

Figure 5:
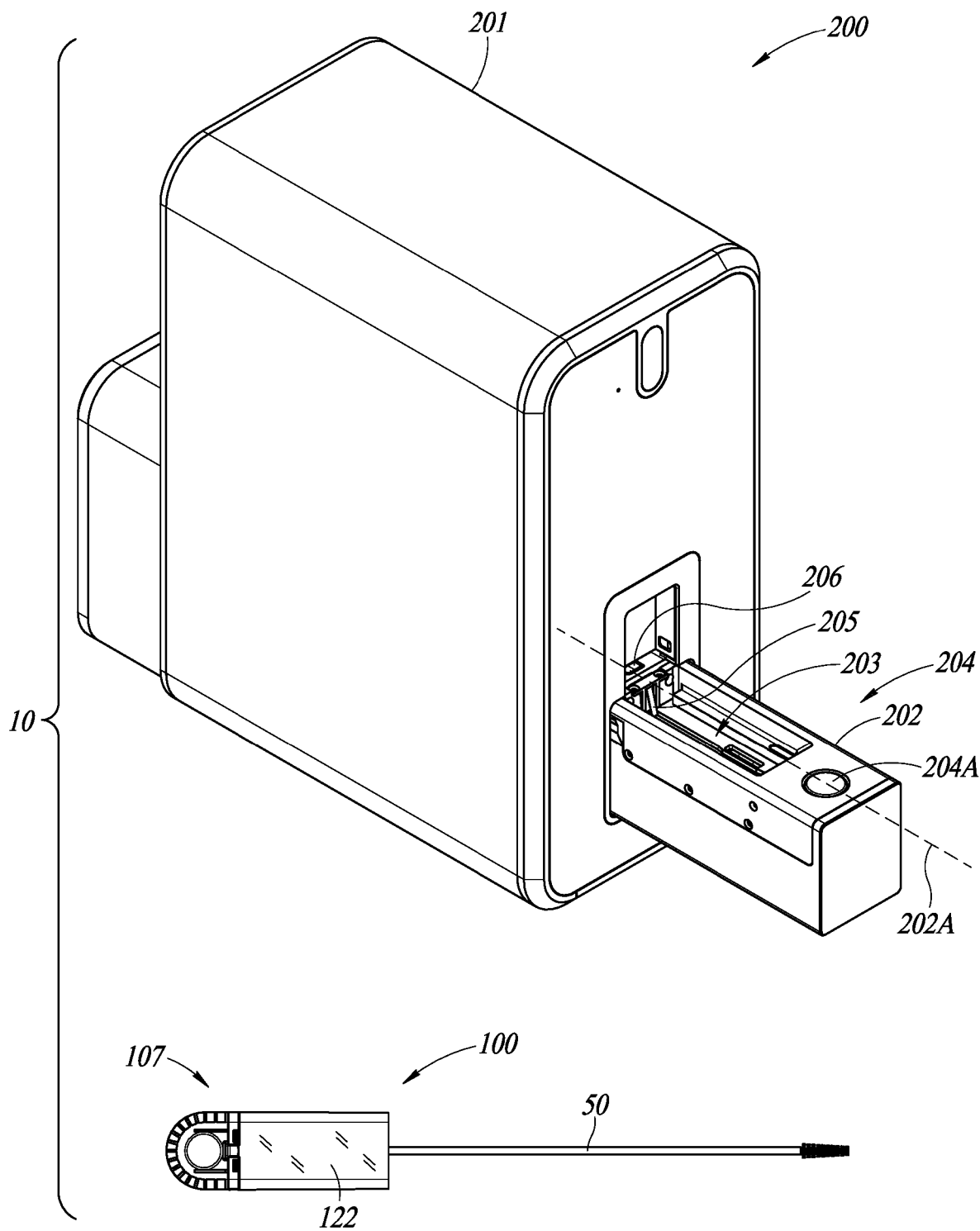
FIG. 5 is a pictorial view of an assay system including assay apparatus and a handheld assay device with a pre-assembled handheld specimen collection tool.
Figure 6:
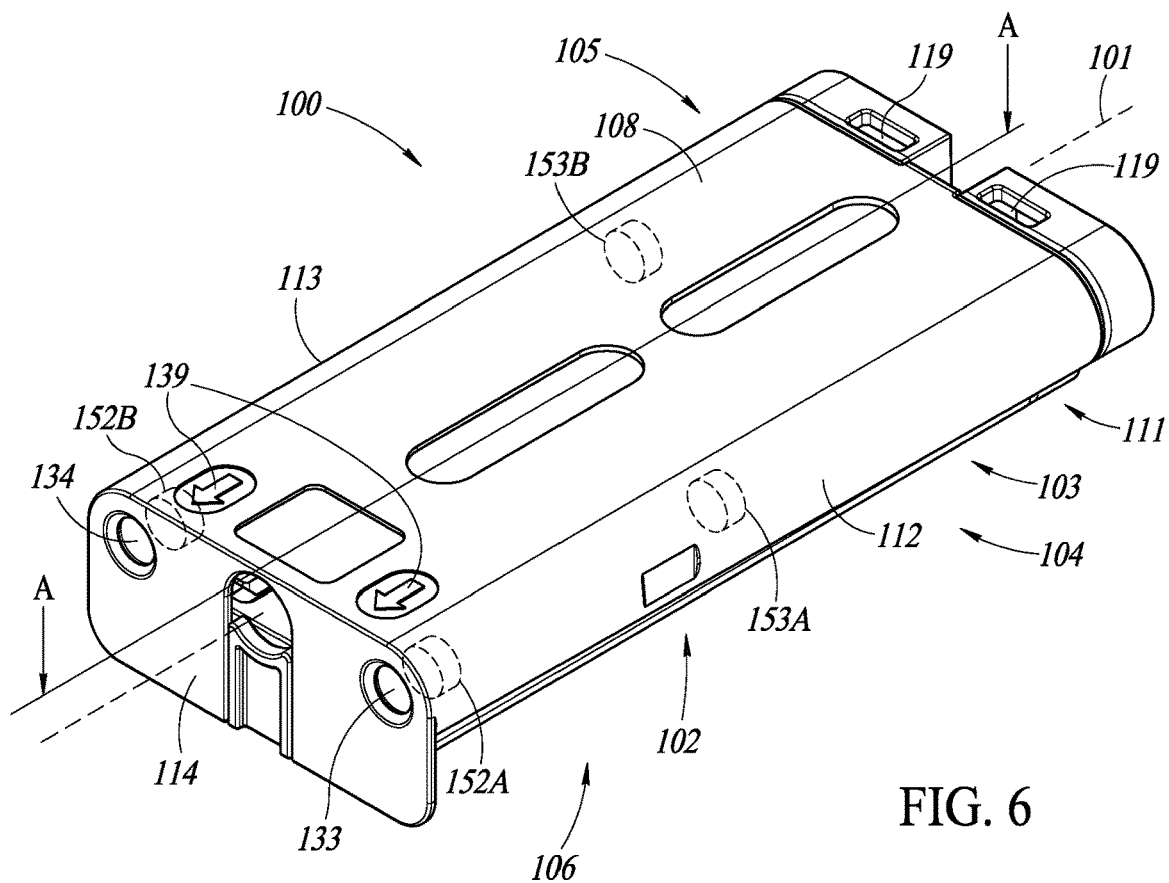
FIG. 6 is a top perspective view of the handheld assay device with a built-in liquid reagent dispensing arrangement.
Figure 7:
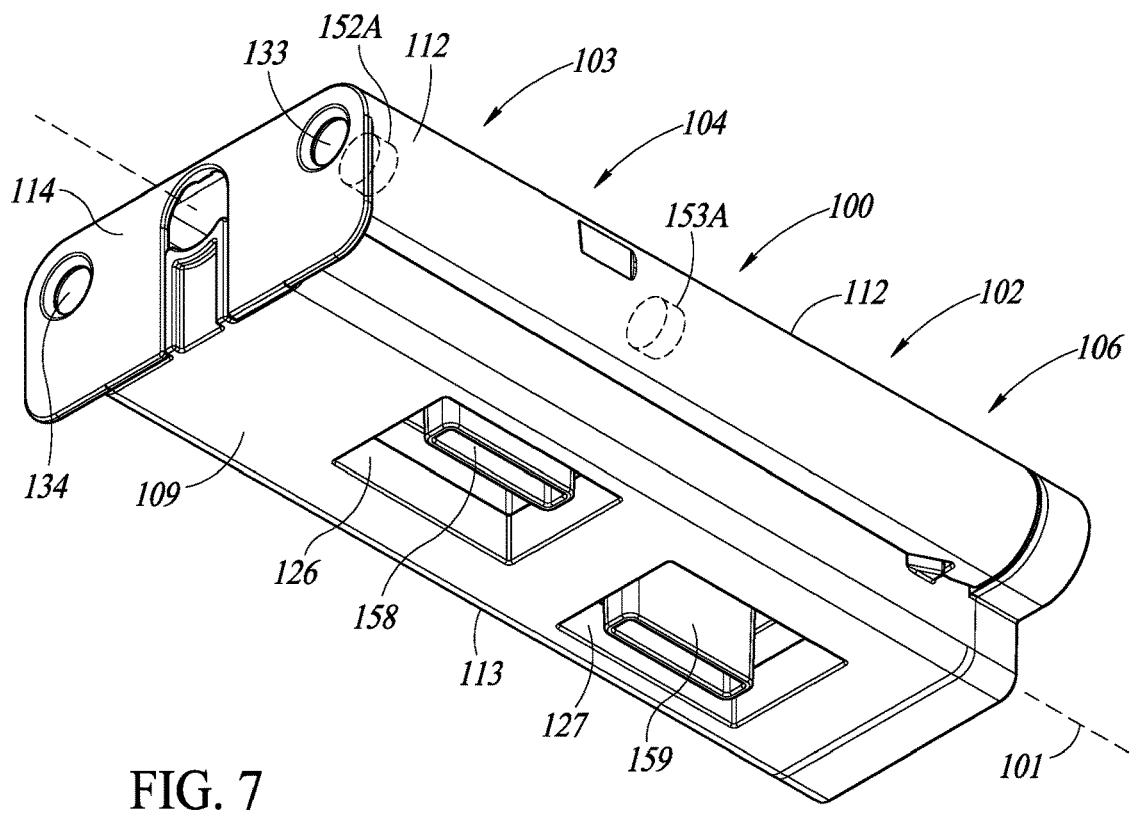
FIG. 7 is a bottom perspective view of the FIG. 6 assay device.
Figure 8:
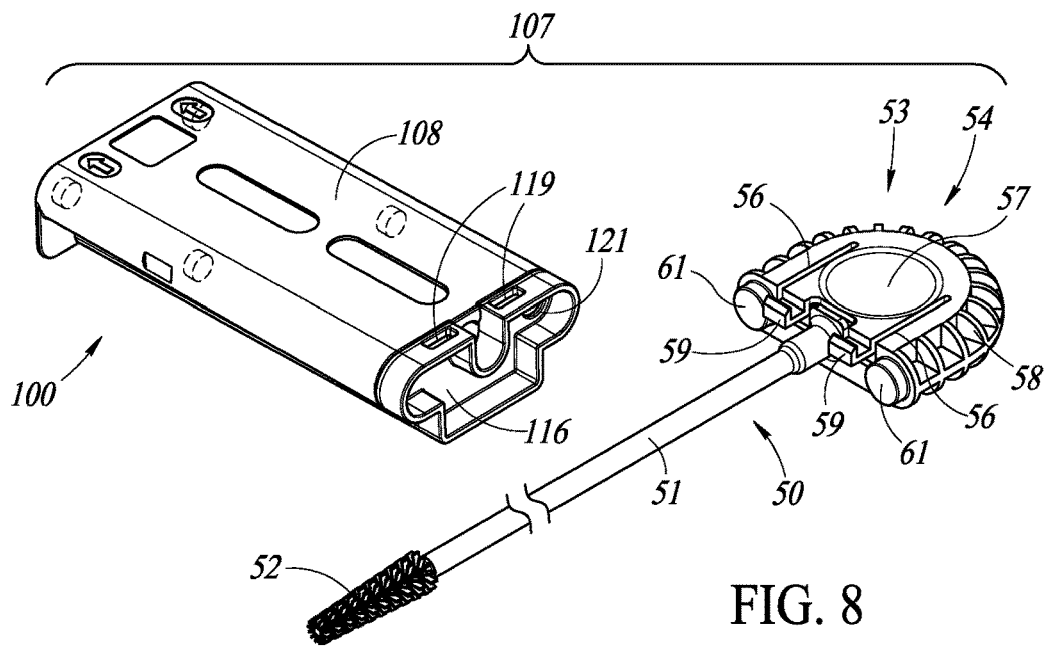
FIG. 8 is a close up view showing a manual operated clamping arrangement for clamping the handheld specimen collection tool to the FIG. 6 assay device.

FIG. 5 shows an assay system 10 for diagnostic purposes of bodily specimens. The assay system 10 includes a handheld assay device 100 for use in a desktop assay apparatus 200 suitable for deployment in an outpatient clinic and the like. The assay apparatus 200 can be powered by a mains supply, a rechargeable battery, and the like. Similar to the afore-mentioned WO 2018/235073 assay apparatus 200, the assay apparatus 200 can be a standalone device with built-in diagnosis capabilities for diagnostic purposes and/or can transmit acquired images and other information for remote processing.

The assay device 100 is preferably pre-assembled with a specimen collection tool 50 for facilitating usage. The assay device 100 and the specimen collection tool 50 preferably include a manual operated clamping arrangement 107 for initially clamping the specimen collection tool 50 to the assay device 100 for preventing relative movement therebetween during transportation and also during obtaining a bodily specimen. The manual operated clamping arrangement 107 is released for enabling sliding removal of the specimen collection tool 50 from the assay device 100 after obtaining a bodily specimen and before insertion of the assay device 100 in the assay apparatus 200 for diagnostic purposes. Alternatively, the assay device 100 and the specimen collection tool 50 can be provided as discrete items.

The assay apparatus 200 includes an apparatus housing 201 having a tray 202 reciprocal between an outermost position and an innermost position. The tray 202 has a longitudinal tray centerline 202A and a longitudinal tray pocket 203 centered therealong for interchangeably receiving assay devices 100. The tray 202 includes a manual operated eject mechanism 204 with an eject button 204A for ejecting an assay device 100 from the tray pocket 203 after it has been processed for diagnostic information. The tray pocket 203 preferably includes one or more micro-switches 205 for ensuring an assay device 100 has been correctly inserted. The tray 200 includes a color target 206 for calibration purposes as explained hereinbelow. The assay apparatus 200 may include a barcode reader for reading an assay device's barcode for determining that an assay device 100 is an authorized assay device.

Assay Devices Including Specimen Collection Tool

FIG. 6 to FIG. 15 show the assay device 100 having a longitudinal assay device centerline 101 and including a generally box-shaped cartridge housing 102 with a cartridge housing interior 103 snugly accommodating a specimen slide 104 slidingly elevated from an initial lowermost specimen introduction position to a final uppermost specimen examination position. The cartridge housing 102 is preferably formed from transparent plastic material, for example, polycarbonate, and the like. The assay device 100 includes a specimen slide securing arrangement 105 for securing the specimen slide 104 in its final uppermost specimen examination position. The assay device 100 includes a built-in liquid reagent dispensing arrangement 106 for dispensing liquid reagent on a bodily specimen smeared on the specimen slide 104 in its initial lowermost specimen introduction position.

The cartridge housing 102 includes a cartridge housing top face 108, a cartridge housing bottom face 109 opposite the cartridge housing top face 108 and a cartridge housing peripheral face 111. The cartridge housing peripheral face 111 includes an opposite pair of a major side wall 112 and a major side wall 113 co-directional with the longitudinal assay device centerline 101, a leading minor end face 114 transverse to the longitudinal assay device centerline 101 and a trailing minor end face 116 transverse to the longitudinal assay device centerline 101 and opposite the leading minor end face 114. For explanatory purposes, the major side wall 112 is hereinafter referred to as the major right side wall and the major side wall 113 is hereinafter referred to as the major left side wall from a viewpoint affording a view of the leading minor end face 114. Additional parts are similarly hereinafter referred to as right and left from a viewpoint affording a view of the leading minor end face 114.

The leading minor end face 114 has a leading throughgoing aperture 117 and the trailing minor end face 116 has a trailing throughgoing aperture 118 both deployed along the longitudinal assay device centerline 101 for enabling passage of the specimen collection tool 50 therethrough. The cartridge housing top face 108 includes a spaced apart pair of cutouts 119 on either side of the longitudinal assay device centerline 101 adjacent the trailing minor end face 116. The trailing minor end face 116 includes a spaced apart pair of trailing blind bores 121 on either side of the trailing throughgoing aperture 118.

The specimen collection tool 50 includes an elongated shaft 51 having a leading specimen collection tip 52 in the form of a brush, a swab, and the like, and a trailing end 53. The trailing end 53 includes a half oval shaped planar hand grip 54 having a spaced apart pair of longitudinal slits 56 co-directional with the shaft 51 for forming a manually depressible release button 57 flexibly connected to a hand grip surround 58. The release button 57 includes a spaced apart of leading clips 59 for snap fitting to the assay device's spaced apart pair of cutouts 119 in the assay device 100 and the specimen collection tool 50's assembled state. The hand grip surround 58 includes a spaced apart pair of circular protrusions 61 for insertion into the assay device's spaced apart pair of trailing blind bores 121 in the assay device 100 and the specimen collection tool 50's assembled state.

FIG. 5 shows the assay device 100 includes a protective foil 122 covering the cartridge housing top face 108 and the leading minor end face 114. The protective foil 122 is kept in place during the obtaining of a bodily sampling and is removed before insertion of the assay device 100 into the assay apparatus 200 for diagnostic purposes. The protective foil 122 prevents finger prints on the cartridge housing top face 108 which can degrade imaging by the assay apparatus 200. The protective foil 122 ensures the leading minor end face 114 remains clean of any bodily specimen which might otherwise be left on sliding removal of a specimen collection tool 50 from an assay device 100 and lead to dirtying the assay apparatus 200's interior.

The cartridge housing 102 includes a dual component construction: a base 123 and a cover 124 for mounting on the base 123. The base 123 includes the cartridge housing bottom face 109, the trailing minor end surface 116 and a trailing section of the cartridge housing top face 108 with the spaced apart pair of cutouts 119. The cartridge housing bottom face 109 is formed with a leading throughgoing aperture 126 and a trailing throughgoing aperture 127 both deployed along the longitudinal assay device centerline 101 for providing access to the cartridge housing interior 103. The base 123 includes an opposite pair of a major right side wall 128 and a major left side wall 129 lateral to the longitudinal assay device centerline 101 correspondingly formed with a longitudinal right barrel 131 and a longitudinal left barrel 132 of the built-in liquid reagent dispensing arrangement 106.

The cover 124 includes the cartridge housing top face 108 and the leading minor end face 114. The leading minor end face 114 is formed with a spaced apart pair of leading throughgoing apertures 133 and 134 in registration with the spaced apart pair of longitudinal right barrel 131 and longitudinal left barrel 132. The cartridge housing top face 108 includes a longitudinal arrangement of three panels transparent to predetermined EMR spectrum. The three panels include a generally square leading cartridge housing top face panel 136 adjacent the leading minor end face 114, a generally rectangular intermediate cartridge housing top face panel 137 midway between the leading minor end face 114 and the trailing minor end face 116, and a generally rectangular trailing cartridge housing top face panel 138 adjacent the trailing minor end face 116. The intermediate cartridge housing top face panel 137 overlies the leading throughgoing aperture 126. The trailing cartridge housing top face panel 138 overlies the trailing throughgoing aperture 127. Alternatively, the leading cartridge housing top face panel 136, the intermediate cartridge housing top face panel 137 and the trailing cartridge housing top face panel 138 can be formed as a single panel.

Figure 12:
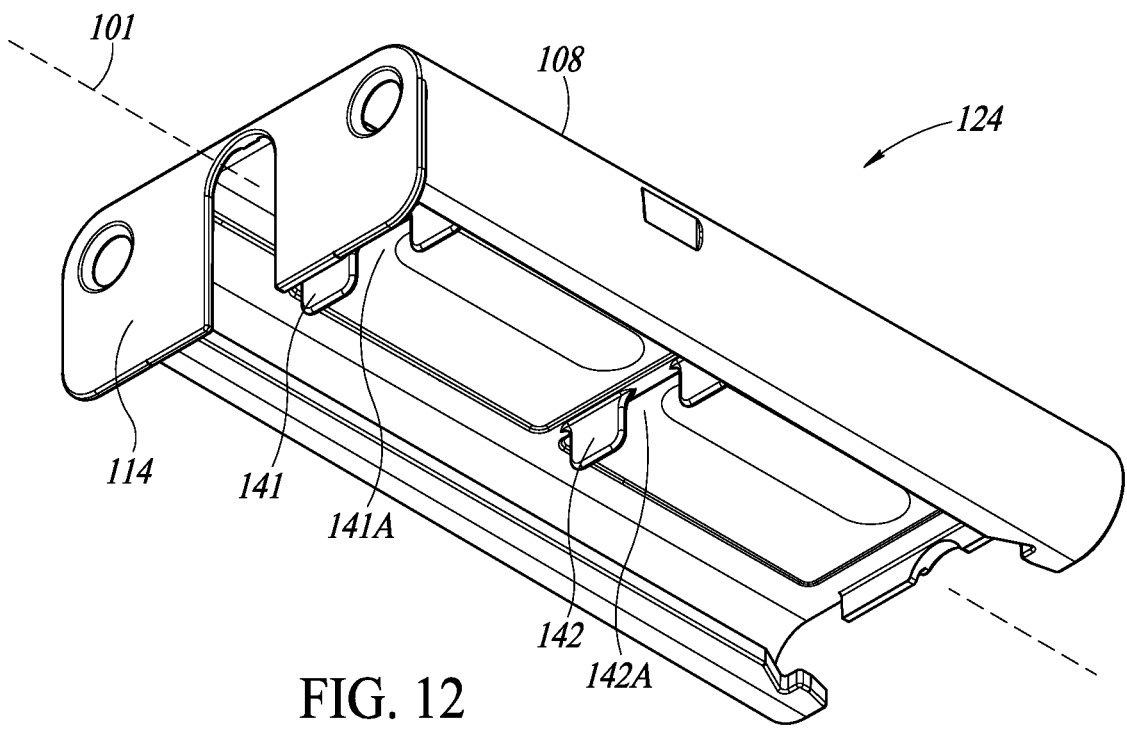
FIG. 12 is a bottom perspective view of a cover of the FIG. 6 assay device.
Figure 13:
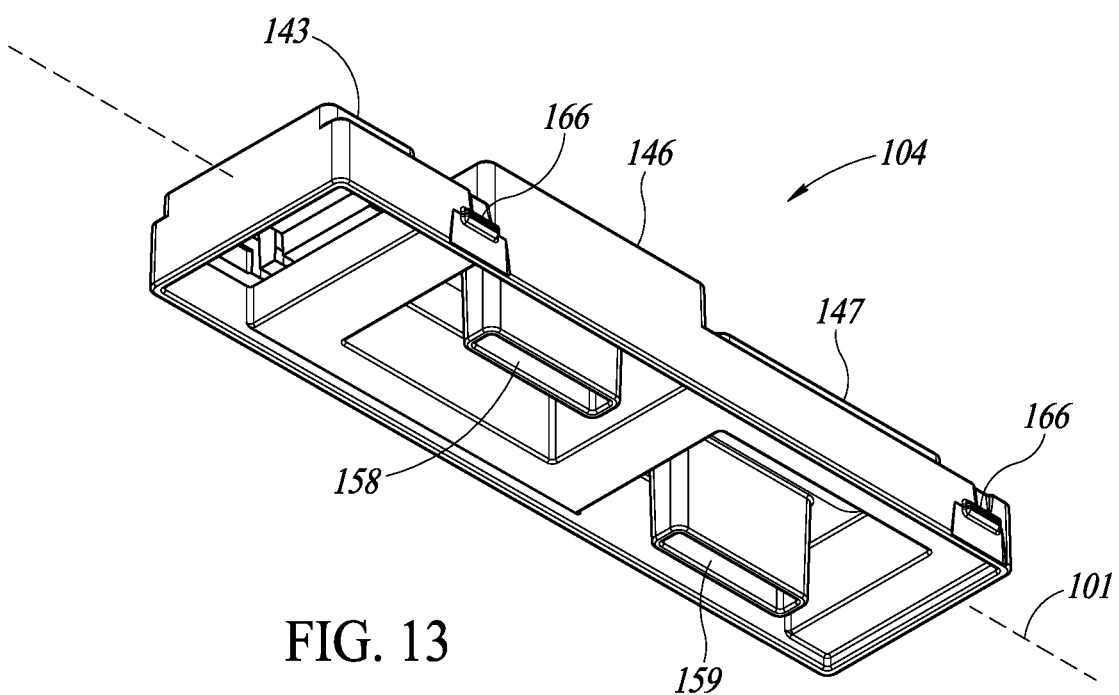
FIG. 13 is a bottom perspective view of a specimen slide of the FIG. 6 assay device.

The cartridge housing top face 108 includes a spaced apart pair of arrows 139 towards the leading minor end surface 114 pointing in the direction of the leading minor end surface 114 for assisting a user to correctly place an unused assay device 100 in the assay apparatus 200. FIG. 12 shows the cartridge housing top face 108 includes a leading guidance member 141 and a trailing guidance member 142 downward depending into the cartridge housing interior 103 for guiding sliding withdrawal of the handheld specimen collection tool 50 from the assay device 100 for smearing bodily specimen on the specimen slide 104. The leading guidance member 141 and the trailing guidance member 142 correspondingly have central apertures 141A and 142A along the longitudinal assay device centerline 101 for passage therethrough of the handheld specimen collection tool 50.

The specimen slide 104 has three spatially discrete work surfaces along the longitudinal assay device centerline 101 as follows: a leading work surface 143 with a pH detection surface 144 for indicating a bodily specimen's pH value, a central work surface 146 and a trailing work surface 147. The pH detection surface 144 can be litmus paper or other pH sensitive material. The central work surface 146 has a longitudinal directed generally rectangular shaped specimen slide panel 148 along the longitudinal assay device centerline 101 and a target 148A toward its leading end. The trailing work surface 147 has a longitudinal directed generally rectangular shaped specimen slide panel 151 along the longitudinal assay device centerline 101 and target 151A towards its leading end. The leading work surface 143 is in registration with the leading cartridge housing top face panel 136, the specimen slide panel 148 and the target 148A are in registration with the intermediate cartridge housing top face panel 137, and the specimen slide panel 151 and the focus target 151A are in registration with the trailing cartridge housing top face panel 138. The specimen slide panel 148 and the specimen slide panel 151 are transparent to the same EMR wavelengths as the intermediate cartridge housing top face panel 137 and the trailing cartridge housing top face panel 138.

The opposite pair of longitudinal right and left barrels 131 and 132 are correspondingly associated with the specimen slide's central work surface 146 and trailing work surface 147. The right and left barrels 131 and 132 have a similar construction and their corresponding components are denoted A and B. The right and left barrels 131 and 132 include leading seals 152A and 152B towards the leading minor end face 114. The leading seals 152A and 152B are exposed through the leading throughgoing apertures 133 and 134. The right and left barrels 131 and 132 include trailing seal members 153A and 153B towards the trailing minor end face 116. The right and left barrels 131 and 132 contain liquid reagents 154A and 154B. The leading seals 152 and the trailing seal members 153 are preferably highly visually distinguishable within the cartridge housing 102 for determining whether an assay device has been used as described hereinbelow with reference to the assay apparatus 200. The right and left barrels 131 and 132 have liquid reagent dispensing ports 156A and 156B correspondingly midway along the central work surface 146 and the trailing work surface 147 for dispensing liquid reagents 154A and 154B thereon.

Figure 14A:
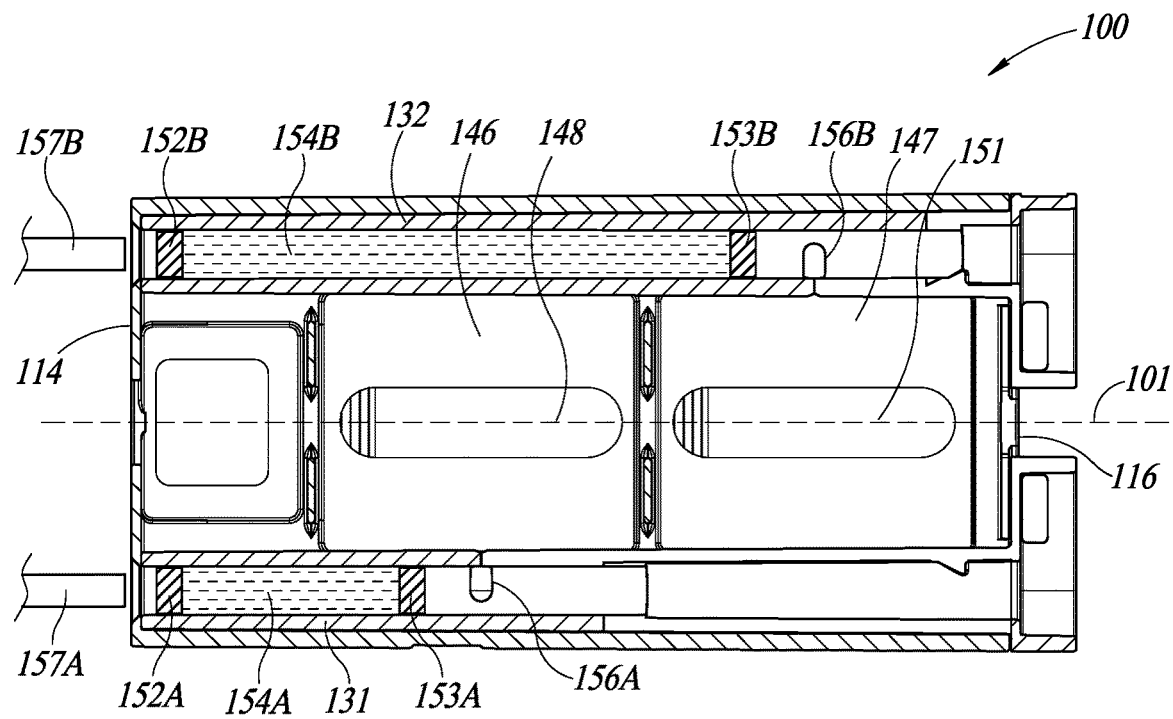
FIG. 14A is a top plan view of the FIG. 6 assay device before dispensing of liquid reagent.

FIG. 14A shows the assay device 100 in an initial pre-liquid reagent dispensing position in which its leading seals 152A and 152B are disposed adjacent the leading minor end surface 114 and its trailing seal members 153A and 153B are both disposed adjacent to and in front of their respective liquid reagent dispensing ports 156A and 156B relative to the leading minor end face 114. FIG. 14A also shows plungers 157A and 157B of the assay assembly 200 are yet to be inserted into the right and left barrels 131 and 132.

Figure 14B:
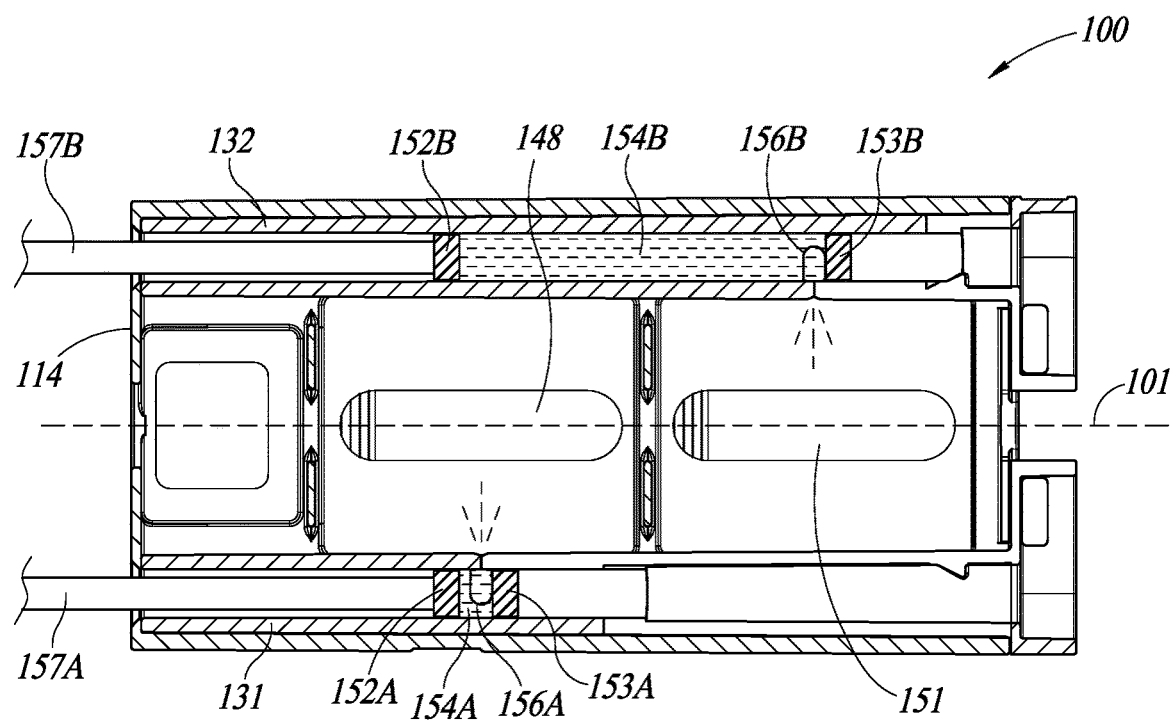
FIG. 14B is a top plan view of the FIG. 6 assay device during dispensing of liquid reagent.

FIG. 14B shows sliding insertion of the plunger 157A into the right barrel 131 urges the leading seal 152A, the liquid reagent 154A, and the trailing seal member 153A along the right barrel 131 until the trailing seal member 153A passes the liquid reagent dispensing port 156A thereby enabling dispensing of the liquid reagent 154A through the liquid reagent dispensing port 156A onto the central work surface 146 and the specimen slide panel 148.

FIG. 14B similarly shows sliding insertion of the plunger 157B into the left barrel 132 urges the leading seal 152B, the liquid reagent 154B, and the trailing seal member 153B along the left barrel 132 until the trailing seal member 153B passes the liquid reagent dispensing port 156B thereby enabling dispensing of the liquid reagent 154B through the liquid reagent dispensing port 156B onto the trailing work surface 147 and the specimen slide panel 151.

FIG. 14B shows the assay device 100 towards the end of dispensing the liquid reagents 154A and 154B as evidenced by the right and left barrels 131 and 132 being nearly empty. Depending on the length of plungers 157A and 157B inserted into the right and left barrels 131 and 132, the leading seals 152A and 152B can also be urged past the liquid reagent dispensing ports 156A and 156B.

The specimen slide 104 includes a central longitudinal directed elongated elevation support 158 and a trailing longitudinal directed elongated elevation support 159 correspondingly downwardly depending from the central work surface 146 and the trailing work surface 147 and correspondingly in registration with the leading throughgoing aperture 126 and the trailing throughgoing aperture 127. The central elevation support 158 and the trailing elevation support 159 are lateral to the longitudinal assay device centerline 101 for not precluding EMR transmission through the assay device 100 and scanning along the specimen slide panel 148 and the specimen slide panel 151.

Figure 15A:
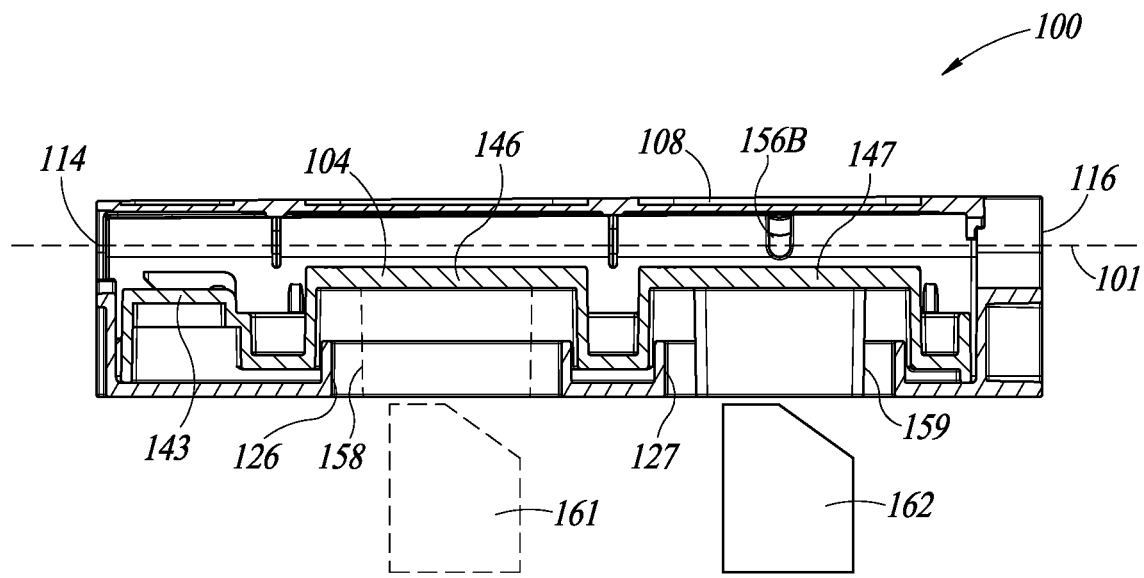
FIG. 15A is a longitudinal cross section of the FIG. 6 assay device with its specimen slide in its initial lowermost specimen introduction position along line A-A in FIG. 6.
Figure 15B:
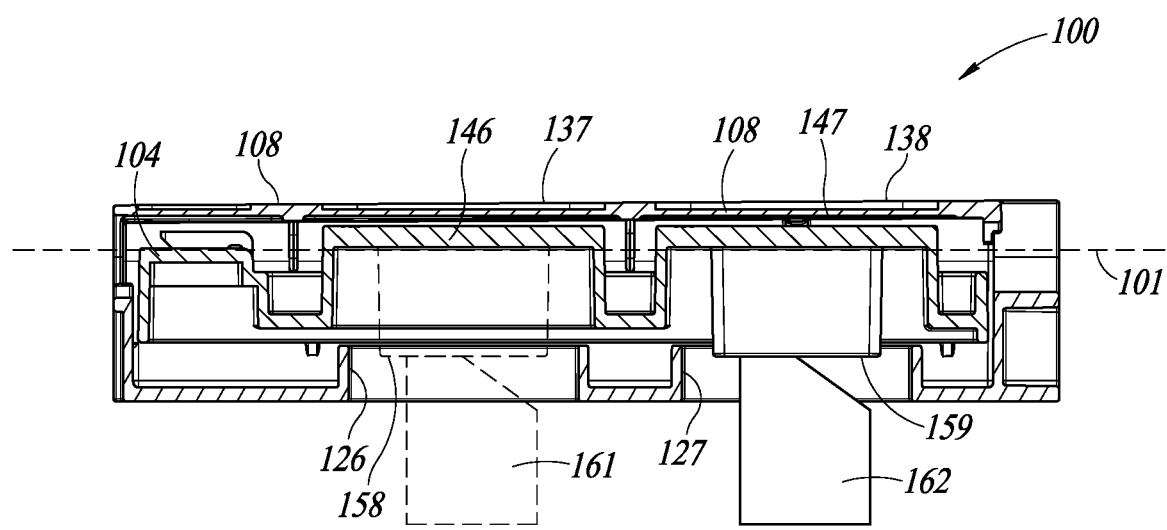
FIG. 15B is a longitudinal cross section of the FIG. 6 assay device with its specimen slide in its final uppermost specimen examination position along line A-A in FIG. 6.

The central elevation support 158 and the trailing elevation support 159 are urged upwards by a leading elevation member 161 and a trailing elevation member 162 of the assay assembly 200 for elevating the specimen slide 104 from its lowermost specimen introduction position (see FIG. 15A) to its uppermost specimen examination position (see FIG. 15B). The specimen slide 104 is correspondingly remote from and adjacent the cartridge housing top face 108 in the initial lowermost specimen introduction position and the final uppermost specimen examination position. In the final uppermost specimen examination position, bodily specimen reacted with the liquid reagent 154A on the central work surface 146 is compressed against the intermediate cartridge housing top face panel 137's underside and bodily specimen reacted with the liquid reagent 154B on the trailing work surface 147 is compressed against the trailing cartridge housing top face panel 138's underside.

Figure 9:
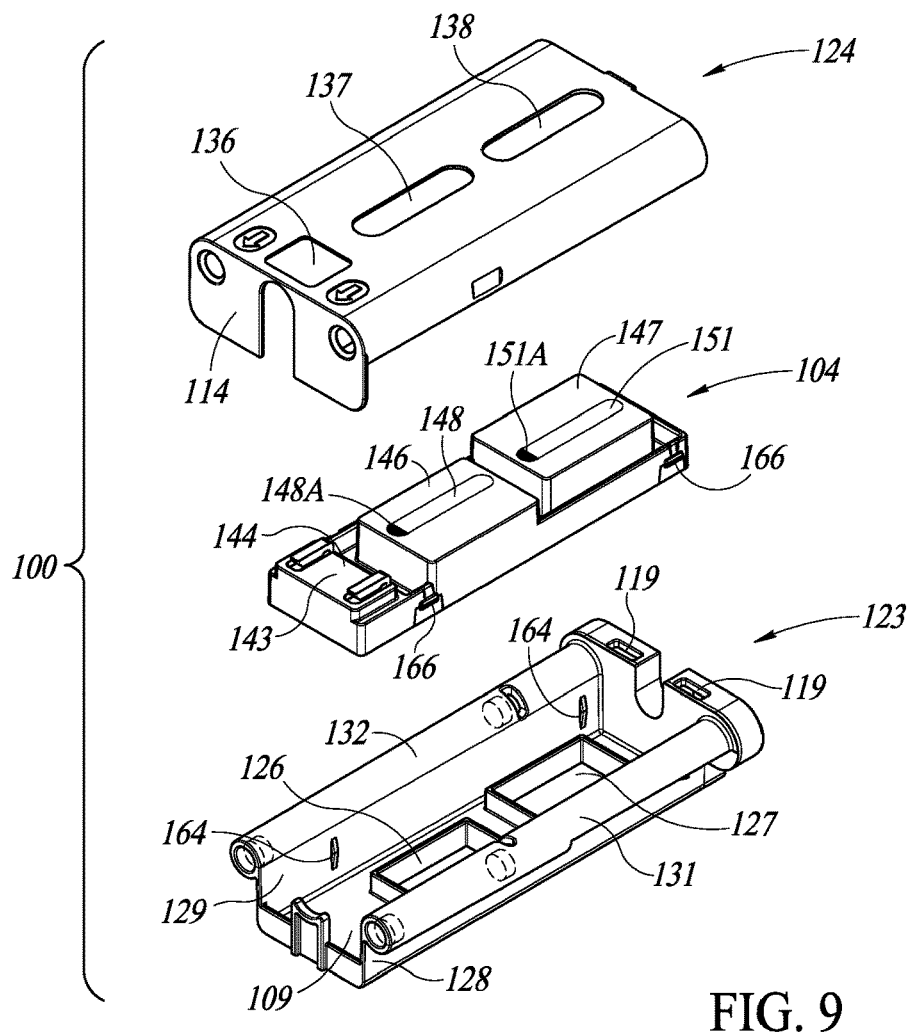
FIG. 9 is an exploded view of the FIG. 6 assay device.
Figure 10:
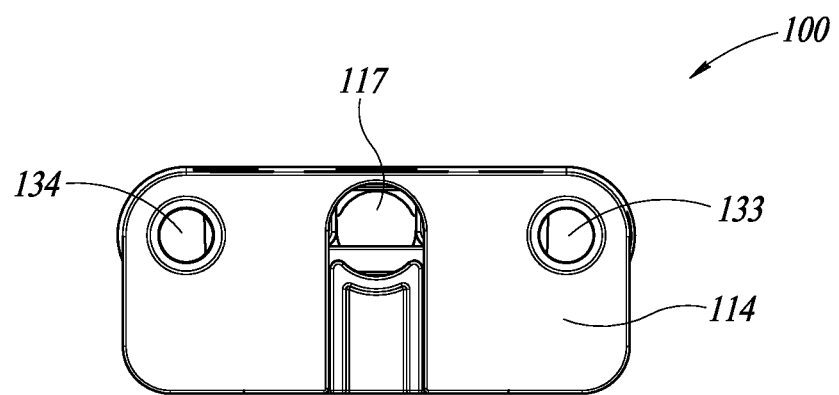
FIG. 10 is a left side elevation view of the FIG. 6 assay device.
Figure 11:
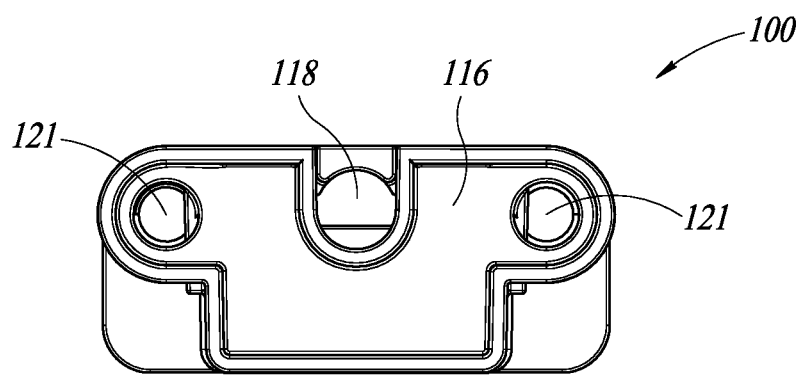
FIG. 11 is a right side elevation view of the FIG. 6 assay device.

The specimen slide securing arrangement 105 for securing the specimen slide 104 in its final uppermost specimen examination position preferably enables an irreversible single displacement from the initial lowermost specimen introduction position to the final uppermost specimen examination position to prevent re-use of the assay device 100. Implementation of the specimen slide securing arrangement 105 is best seen in FIG. 9: The base 123's major right side wall 128 has a spaced apart pair of inward directed protrusions 163 (obstructed from view) and its major left side wall 129 has a spaced apart pair of inward directed protrusions 164 opposite the spaced apart pair of inward directed protrusions 163. The specimen slide 104 has a spaced apart pair of outwardly biased clips 166 in registration with the spaced apart pair of inward directed protrusions 163. The specimen slide 104 has a spaced apart pair of outwardly biased clips 167 (obstructed from view) in registration with the spaced apart pair of inward directed protrusions 164. On upward displacement of the specimen slide 104 from its initial lowermost specimen introduction position to its final uppermost specimen examination position, the spaced apart pair of outwardly biased clips 166 irreversible pass the spaced apart pair of inward directed protrusions 163 and the spaced apart pair of outwardly biased clips 167 irreversible pass the spaced apart pair of inward directed protrusions 164.

The assay device 100 can be provided with an alternative built-in liquid reagent dispensing arrangement 106' in which the right barrel 131 is fitted a right stopcock 168A and the left barrel 132 is fitted with a left stopcock 168B. The right stopcock 168A and the left stopcock 168B act as trailing seal members. The construction of the latter 106' is largely similar to the former 106 and therefore similar parts are likewise numbered.

FIG. 16A to FIG. 19B show the right barrel 131 and the left barrel 132 rotatingly receive the stopcocks 168A and 168B at their liquid reagent dispensing ports 156A and 156B. The right and left stopcocks 168A and 168B are permanently deployed at their corresponding liquid reagent dispensing ports 156A and 156B. The right and left barrels 131 and 132 are correspondingly formed with stopcock grooves 169A and 169B opposite their liquid reagent dispensing ports 156A and 156B. The stopcocks 168A and 168B have stopcock actuation tabs 171A and 171B protruding through the stopcock grooves 169A and 169B (see FIG. 18B and FIG. 19B). The assay assembly 200 includes right and left stopcock actuators 190A and 190B for correspondingly rotating the right and left stopcocks 168A and 168B from an initial closed position at a pre-liquid reagent dispensing position to an open position for liquid reagent dispensing purposes on their forward displacement towards the right and left stopcocks 168A and 168B.

Figure 16A:
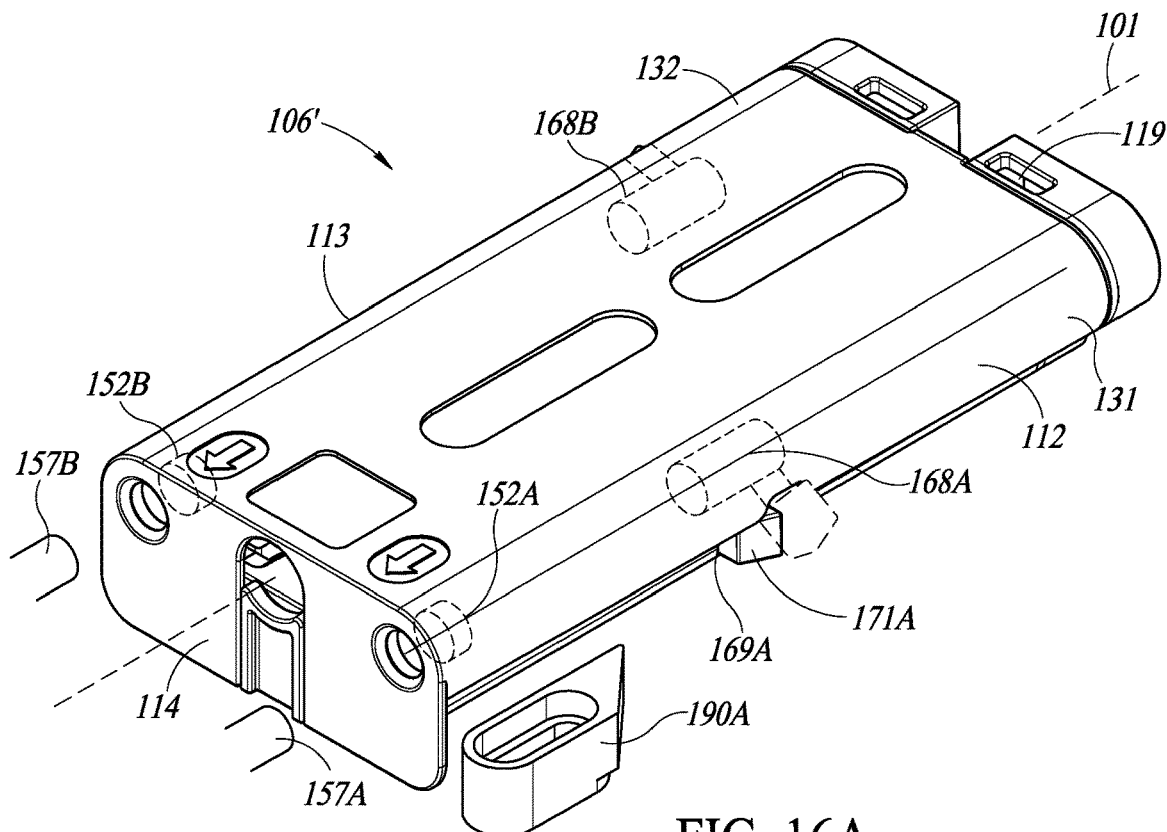
FIG. 16A is a right top perspective view of a handheld assay device with a built-in liquid reagent dispensing arrangement including stopcocks.
Figure 16B:
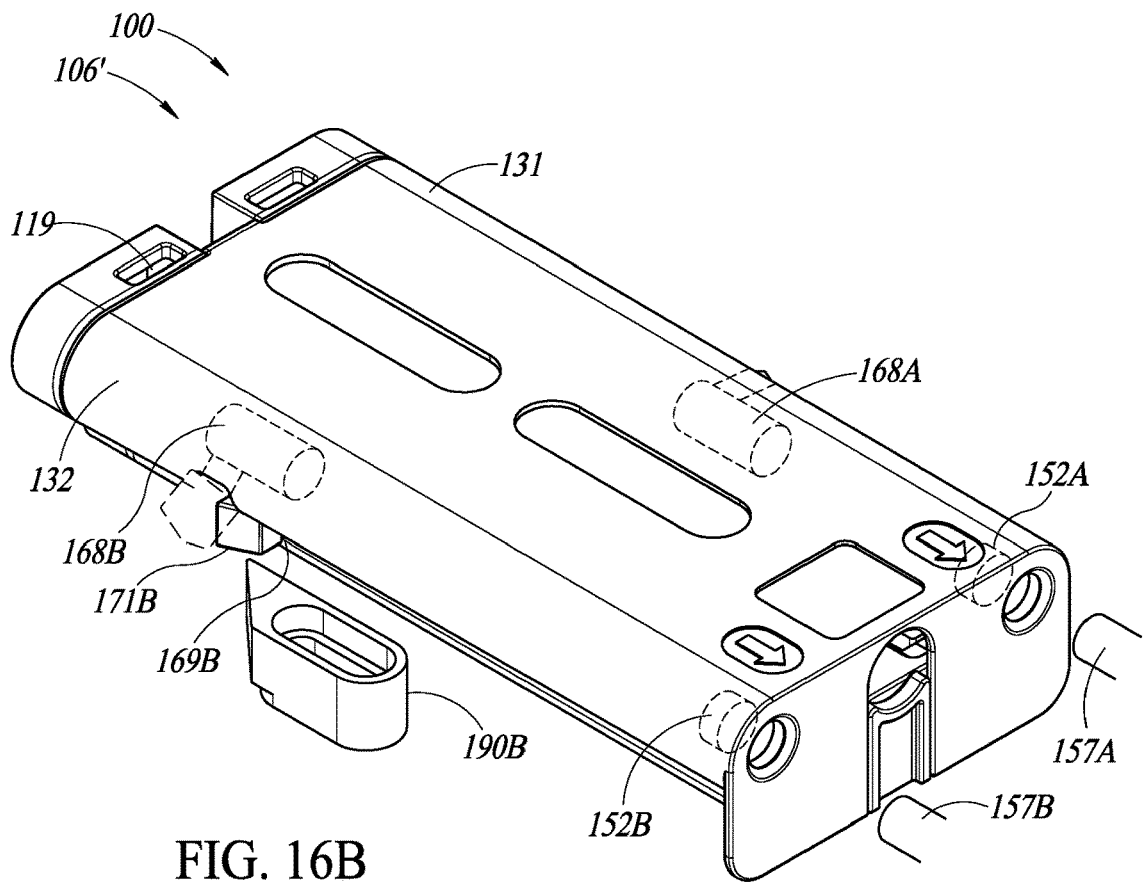
FIG. 16B is a left top perspective of the FIG. 16 assay device.

FIG. 16A shows rotation of the right stopcock 168A through about 45° counterclockwise from its initial closed position to its open position as evidenced by the change of the position of its stopcock actuation tab 171A from its closed position shown in solid lines to its open position shown in dashed lines. FIG. 16B similarly shows rotation of the left stopcock 168B through about 45° clockwise from its initial closed position to its open position as evidenced by the change of the position of its stopcock actuation tab 171B from its closed position shown in solid lines to its open position shown in dashed lines.

Figure 17A:
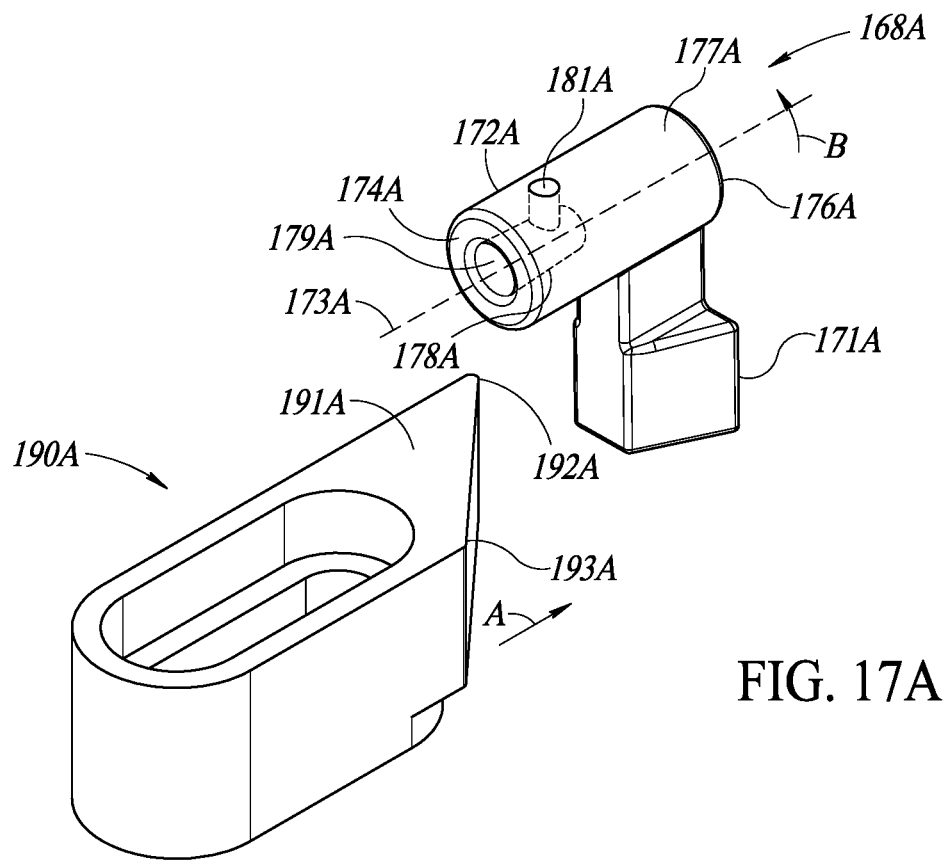
FIG. 17A is a schematic view of a right stopcock of the FIG. 16 assay device before actuation by its stopcock actuator.
Figure 17B:
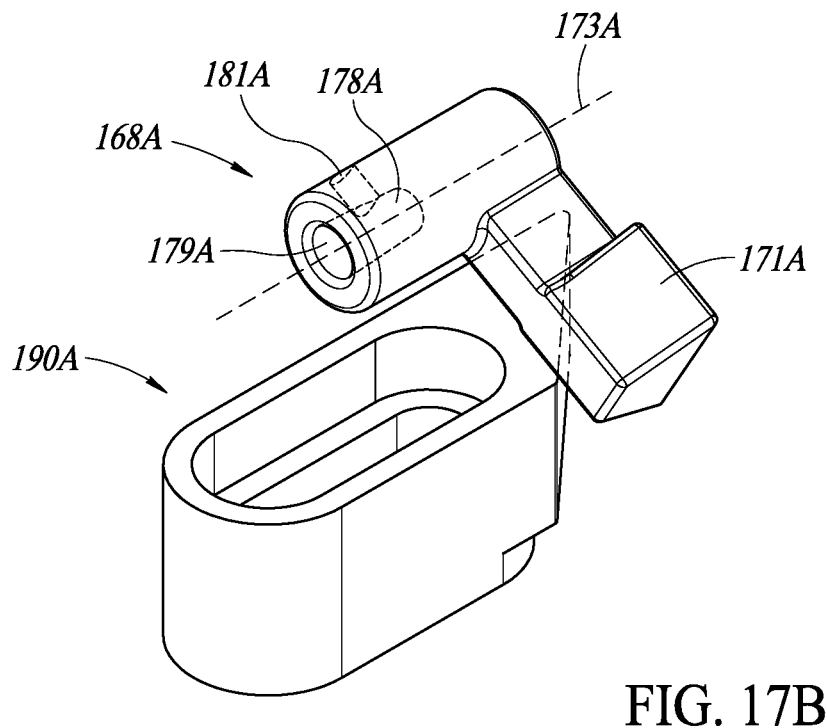
FIG. 17B is a schematic view of the right stopcock after actuation by its stopcock actuator.

FIG. 17A and FIG. 17B show the right stopcock 168A has a cylindrical body 172 having a rotation axis 173 co-axial with the right barrel 131 with a leading stopcock face 174 facing the leading minor end face 114, a trailing stopcock face 176 facing away from the leading minor end face 114 and a peripheral stopcock face 177 extending between the leading stopcock face 174 and the trailing stopcock face 176. The right stopcock 168A includes a L-shaped channel 178A extending from its front stopcock face 174A to its peripheral stopcock face 177A. The L-shaped channel 178A has a L-shaped channel inlet 179A in the front stopcock face 174A in flow communication with the right barrel 131 and a L-shaped channel outlet 181A in the peripheral stopcock face 177A for selective flow communication with the liquid reagent dispensing port 156A.

FIG. 17A and FIG. 17B show the right stopcock actuator 190A has a leading stopcock actuator taper 191A facing the stopcock actuation tab 171A. The leading stopcock actuator taper 191A tapers from a forwardmost innermost tip 192A to a rearmost outermost edge 193A. The stopcock actuator 190A initially contacts the stopcock actuation tab 171A at its forwardmost innermost tip 192A. On subsequent approaching of the stopcock actuator 190A and the right stopcock 168A as denoted by arrow A, the stopcock actuator 190A progressively counterclockwise rotates the right stopcock 168A as denoted by arrow B to its liquid reagent dispensing position as the leading stopcock actuator taper 191A moves under the right stopcock actuation tab 171A.

The left stopcock 168B is a mirror image of the right stopcock 168A relative to the longitudinal assay device centerline 101. Similarly, the left stopcock actuator 190B is a mirror image of the right stopcock actuator 190A relative to the longitudinal assay device centerline 101.

Figure 18A:
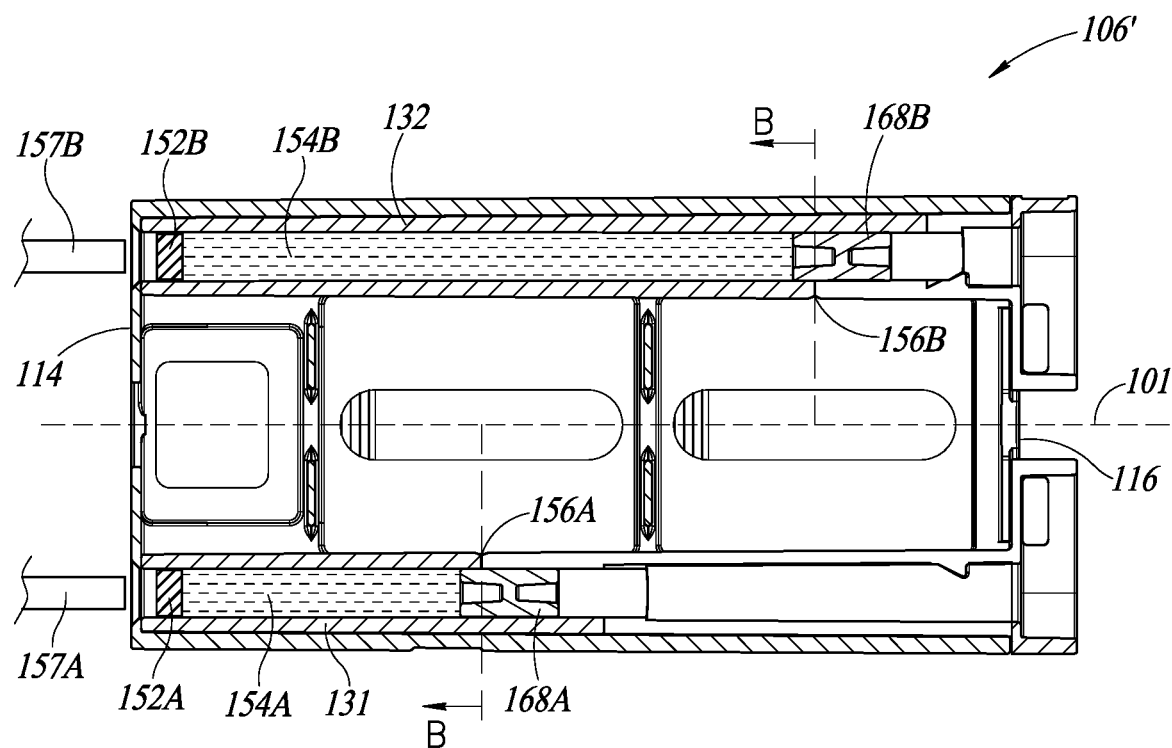
FIG. 18A is a top plan view of the FIG. 16 assay device before dispensing liquid reagent.
Figure 18B:
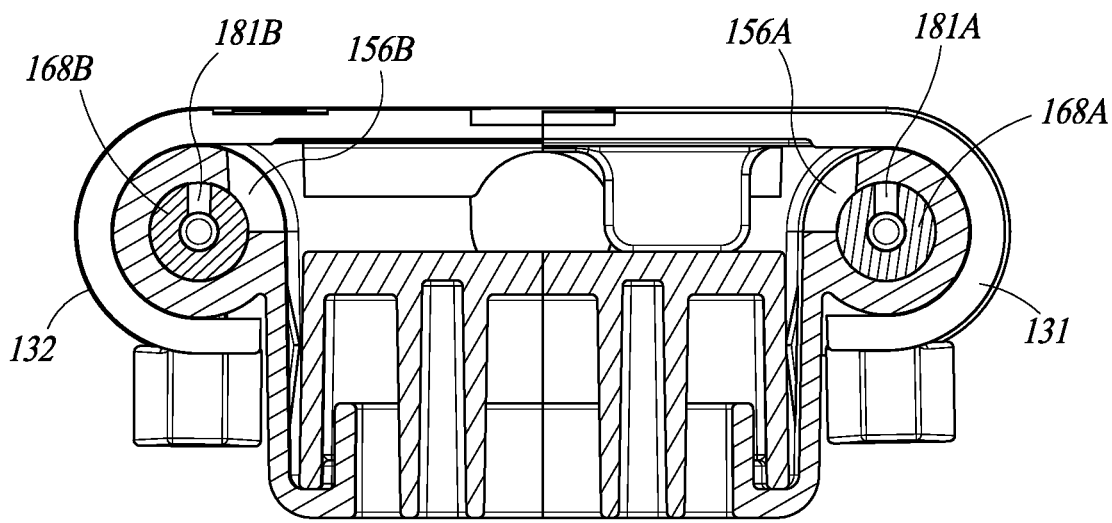
FIG. 18B is a transverse cross section of the FIG. 16 assay device along a stepped line B-B in FIG. 18A before dispensing liquid reagent.

FIG. 18A and FIG. 18B show the right and left stopcocks 168A and 168B in their initial pre-liquid reagent dispensing position with their stopcock actuation tabs 171A and 171B directed downwards adjacent the major right side wall 112 and the major left side wall 113 and their L-shaped channel outlets 181A and 181B sealed against the inside surfaces of their corresponding barrels 131 and 132. The plungers 157A and 157B of the assay assembly 200 are yet to be inserted into the right and left barrels 131 and 132. The right stopcock actuator 190A and the left stopcock actuator 190B are correspondingly in front of the right stopcock 168A and left stopcock 168B.

Figure 19A:
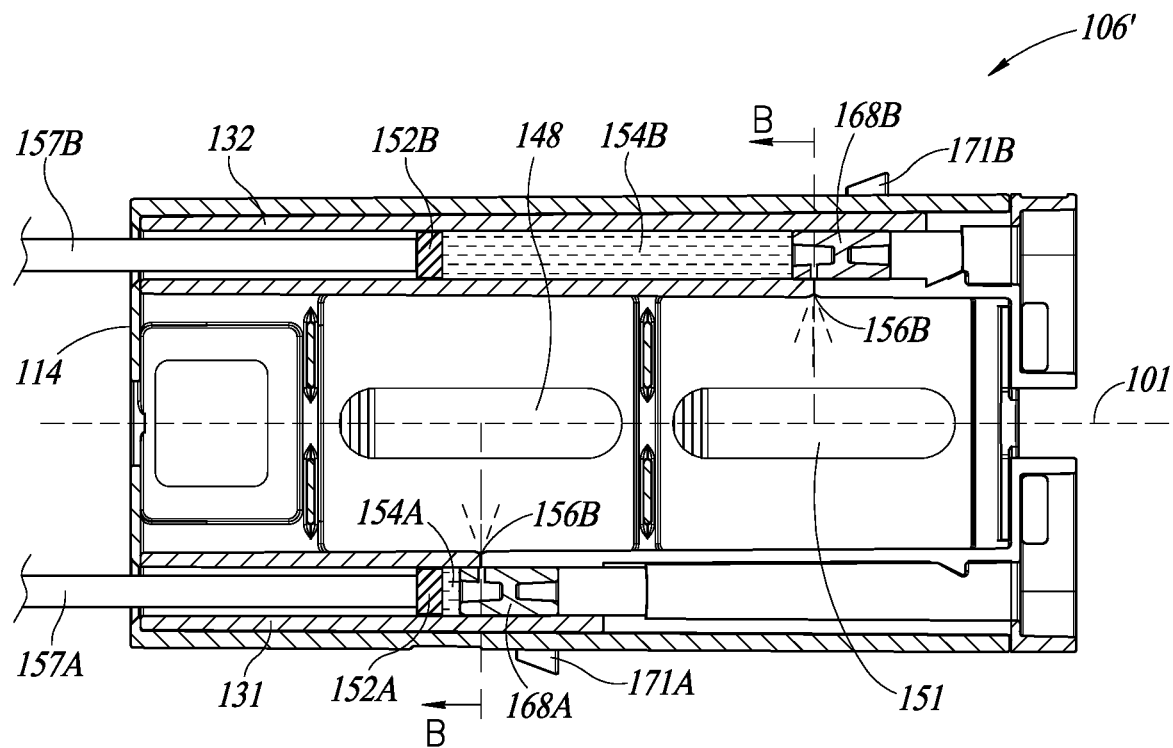
FIG. 19A is a top plan view of the FIG. 16 assay device during dispensing liquid reagent.
Figure 19B:
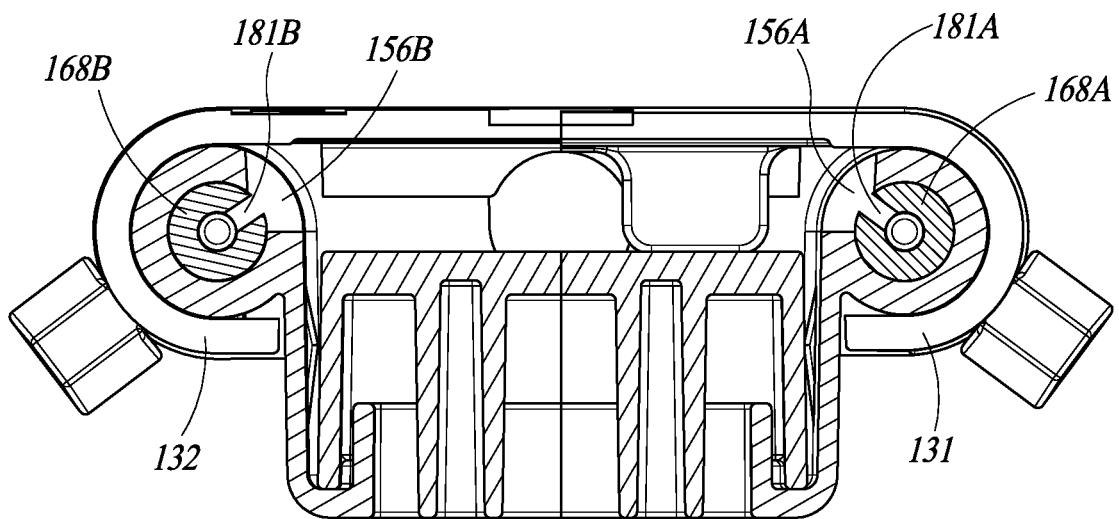
FIG. 19B is a transverse cross section of the FIG. 16 assay device along a stepped line B-B in FIG. 19A during dispensing liquid reagent.
Figure 20:
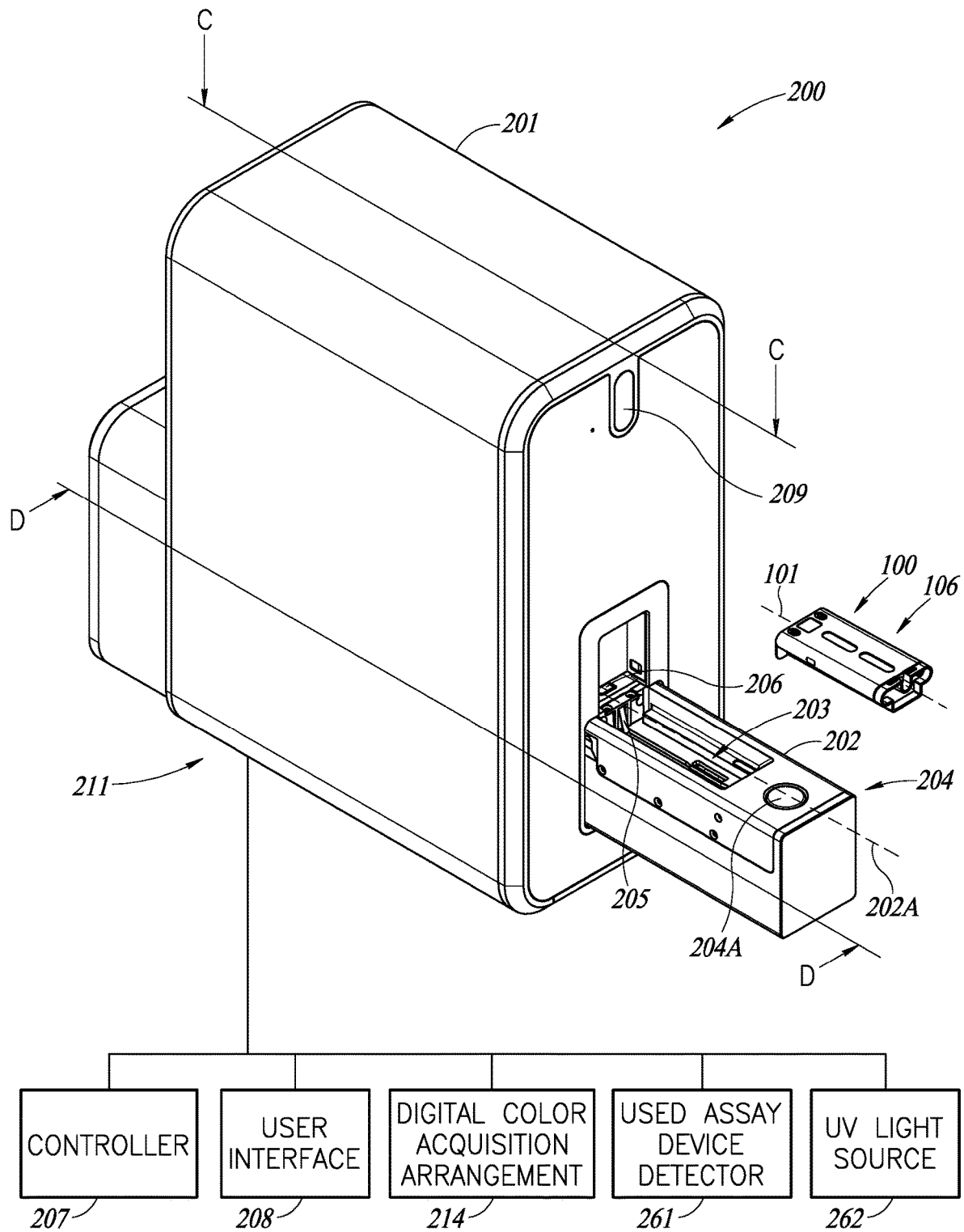
FIG. 20 is a combined perspective view and block diagram of assay apparatus for use with the FIG. 6 assay device.

FIG. 19A and FIG. 19B show the plungers 157A and 157B inserted into the right and left barrels 131 and 132 and the right stopcock actuator 190A and the left stopcock actuator 190B have correspondingly rotated the right stopcock 168A and the left stopcock 168B to their liquid reagent dispensing positions as evidenced by their stopcock actuation tabs 171A and 171B outwardly protruding with respect to their respective major right side wall 112 and the major left side wall 113. The L-shaped channel outlets 181A and 181B are aligned with their respective liquid reagent dispensing ports 156A and 156B. The liquid reagent dispensing arrangement 106' dispenses liquid reagent 154A through the liquid reagent dispensing port 156A onto the specimen slide panel 148 and liquid reagent 154B through the liquid reagent dispensing port 156B onto the specimen slide panel 151.

Assay Apparatus

Figure 21A:
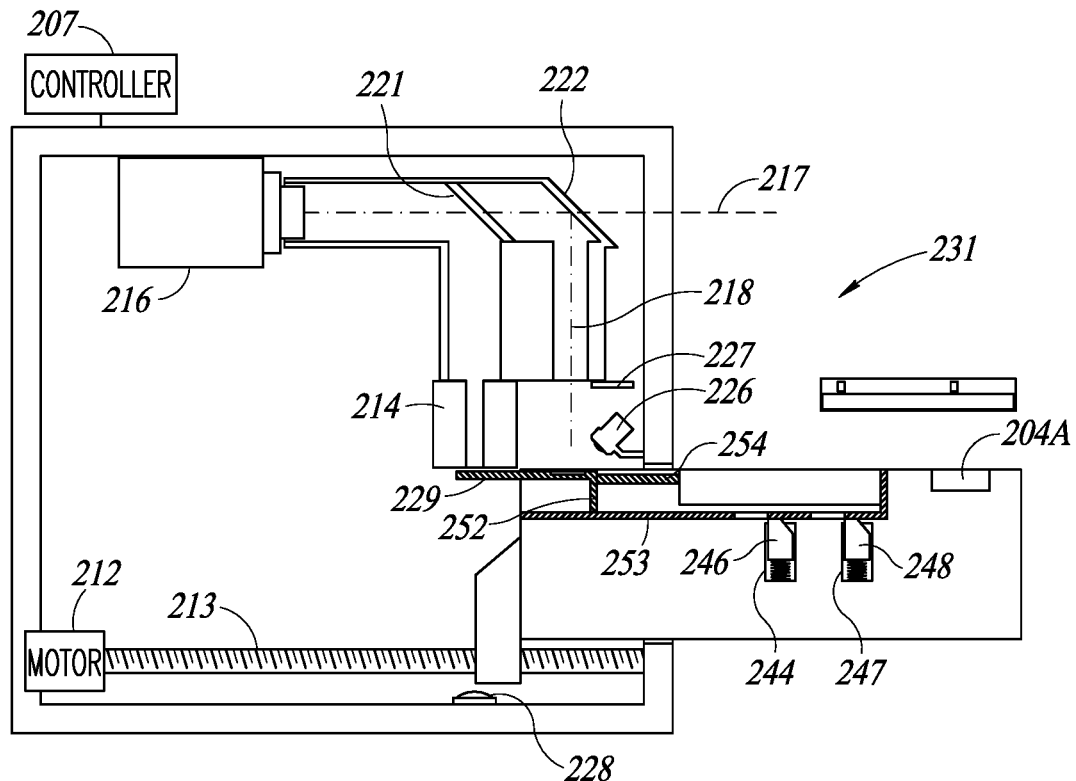
FIG. 21A is a schematic longitudinal cross section of the assay apparatus along line C-C in FIG. 20 with its complete tray in its outermost position.
Figure 21B:
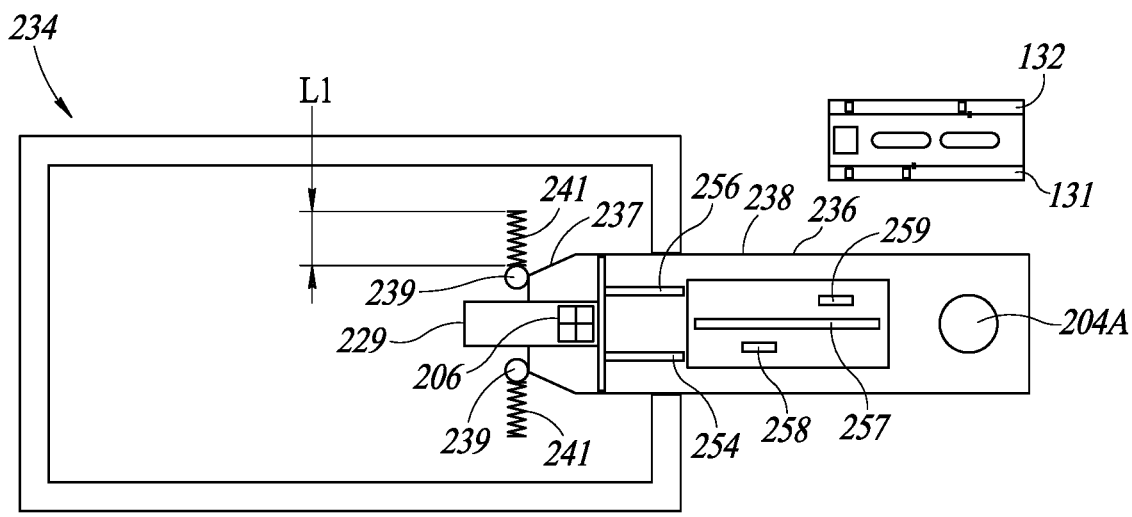
FIG. 21B is a schematic transverse cross section of the assay apparatus along line D-D in FIG. 20 with its complete tray in its outermost position.
Figure 22A:
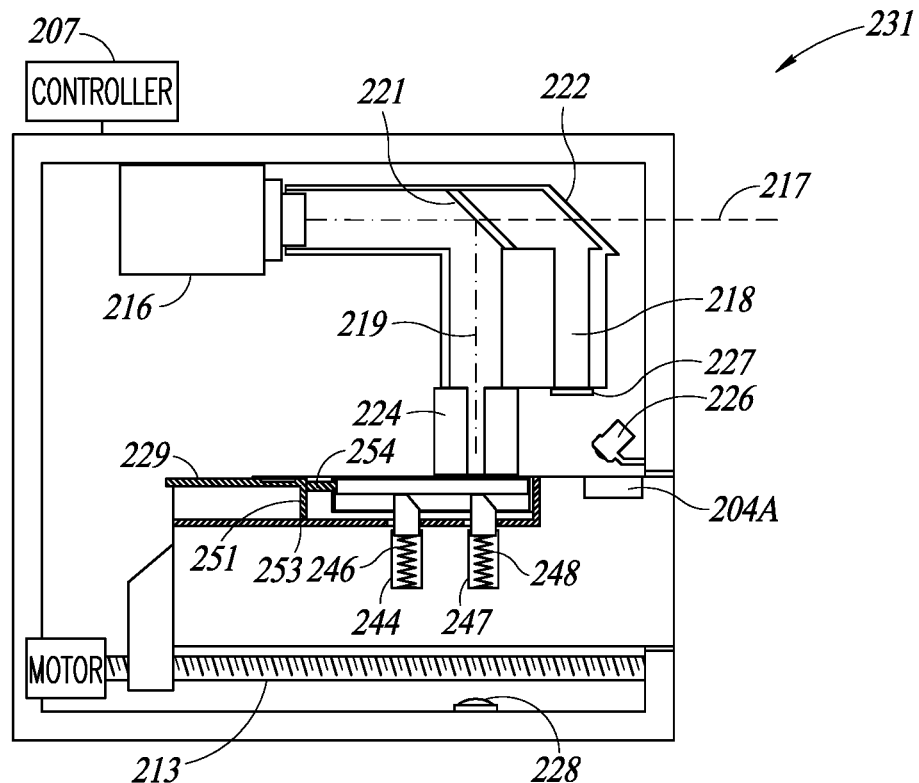
FIG. 22A is a schematic longitudinal cross section of the assay apparatus along line C-C in FIG. 20 with its complete tray in its innermost position.
Figure 22B:
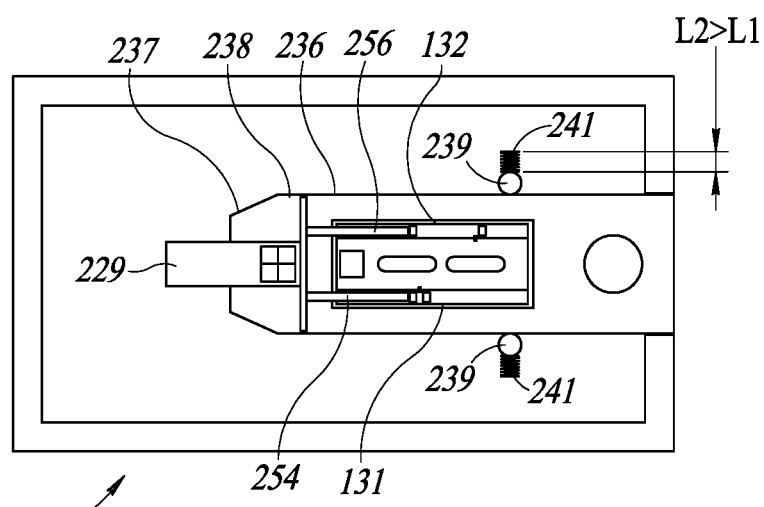
FIG. 22B is a schematic transverse cross section of the assay apparatus along line D-D in FIG. 20 with its complete tray in its innermost position.

The assay apparatus 200 is now described with reference to FIG. 20 to FIG. 24 for use with assay devices 100 having a built-in liquid reagent dispensing arrangement 106. FIG. 21A and FIG. 22A are schematic longitudinal cross sections of the assay apparatus 200 which have been modified to show components which would otherwise not be shown in a longitudinal cross section along the longitudinal cross section line C-C. FIG. 21B and FIG. 22B include components along a stepped longitudinal cross section line E-E shown in FIG. 23. FIG. 21B and FIG. 22B are schematic transverse cross sections of the assay apparatus 200 which have been modified to show components which would otherwise not be shown in a transverse cross section along the transverse cross section line D-D.

As described hereinabove with reference to FIG. 5, the assay apparatus 200 includes apparatus housing 201 having a tray 202 having a longitudinal tray centerline 202A and being reciprocal between an outermost position (see FIG. 21A and FIG. 21B) and an innermost position (see FIG. 22A and FIG. 22B). The tray 202 includes a tray pocket 203 for interchangeably receiving an assay device 100 such that its longitudinal assay device centerline 101 is co-directional with the longitudinal tray centerline 202A. The tray 202 includes a manually operated eject mechanism 204 including an eject button 204A for ejecting an assay device 100 after it has been processed for diagnostic information. The tray 202 has a color target 206 for calibration purposes for accurately determining as assay device 100's pH color reading. The assay apparatus 200 stops the tray 202 at its outermost position if an assay device 100 has been incorrectly inserted and issues an audible or visual alert for alerting a user.

The assay apparatus 200 includes a controller 207 for controlling operation of same, a user interface 208 for entering information regarding a clinical procedure, and a START button 209. The assay apparatus 200 includes a motorized arrangement 211 having a motor 212 for driving a screw threaded drive shaft 213 for reciprocating the tray 202 between its outermost position and its innermost position. Clockwise rotation of the drive shaft 213 urges the tray 202 from its outermost position to its innermost position and conversely counterclockwise rotation of the drive shaft 213 urges the tray 202 from its innermost position to its outermost position.

The assay apparatus 200 includes a digital color acquisition arrangement 214 having a single color camera 216 with an optical axis 217 and dual optical paths as follows: A first optical path 218 (see FIG. 21A) for acquiring a color target image of the tray 202's color target 206 and a color pH reading image of an assay device's pH detection surface 144. And a second optical path 219 (see FIG. 22A) for obtaining microscope images of bodily specimen from an assay device's central work surface 146 and trailing work surface 147 after being correspondingly reacted with liquid reagent 154A and liquid reagent 154B. The color camera 216 is, for example, any commercially available 4 to 25 Megapixel CMOS image sensor. The assay apparatus 200 preferably acquires the color target image, the color pH reading image and the microscope images for an assay device 100 during a single continuous inward movement of the tray 202 from its outermost position to its innermost position.

The digital color acquisition arrangement 214 includes two mirrors along the optical axis 217 and inclined at 45° thereto as follows: a semi-reflective mirror 221 proximate to the color camera 216 and a fully reflective mirror 222 distal to the color camera 216. Accordingly, the first optical path 218 includes the semi-reflective mirror 221 and the fully reflective mirror 222. The digital color acquisition arrangement 214 includes an ×10 to ×1000 magnification lens system 224 for acquiring microscope images. Accordingly, the second optical path 219 includes the semi-reflective mirror 221 and the ×10 to ×1000 magnification lens system 224. The digital color acquisition arrangement 214 also preferably includes auto-focusing capability along the second optical path 219.

For use during image acquisitions along the first optical path 218, the digital color acquisition arrangement 214 includes a first illumination source 226 disposed above the tray 202 for illuminating an assay device 100 from above and a first optical path shutter 227 for selectively opening and closing the first optical path 218. For use during image acquisitions along the second optical path 219, the digital color acquisition arrangement 214 includes a second illumination source 228 disposed beneath the tray 202 for backlighting an assay device 100 through the tray 202 and a second optical path shutter 229 inwardly extending from the tray 202 for selectively opening and closing the second optical path 219. The first optical path shutter 227 and the second optical path shutter 229 work in unison to constitute a shutter arrangement 231 for selectively opening and closing the first optical path 218 and correspondingly closing and opening the second optical path 219. Accordingly, the digital color acquisition arrangement 214 acquires a color target image and a pH reading image by switching on the illumination source 226 only, opening the first optical path 218 and closing the second optical path 219. And the digital color acquisition arrangement 214 acquires microscope images by switching on the illumination source 228 only, closing the first optical path 218 and opening the second optical path 219.

Figure 23:
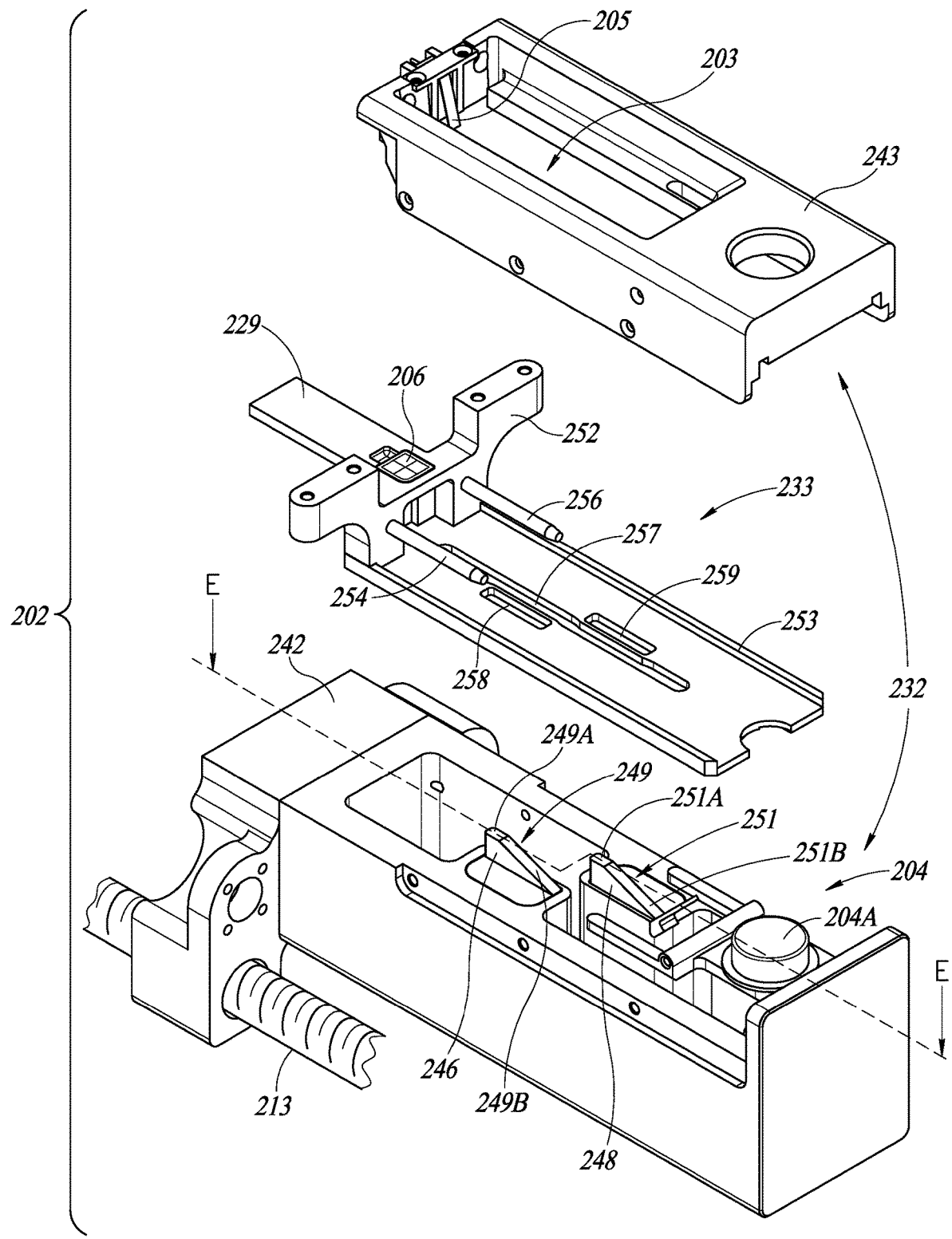
FIG. 23 is an exploded view of the assay assembly's tray.
Figure 24A:
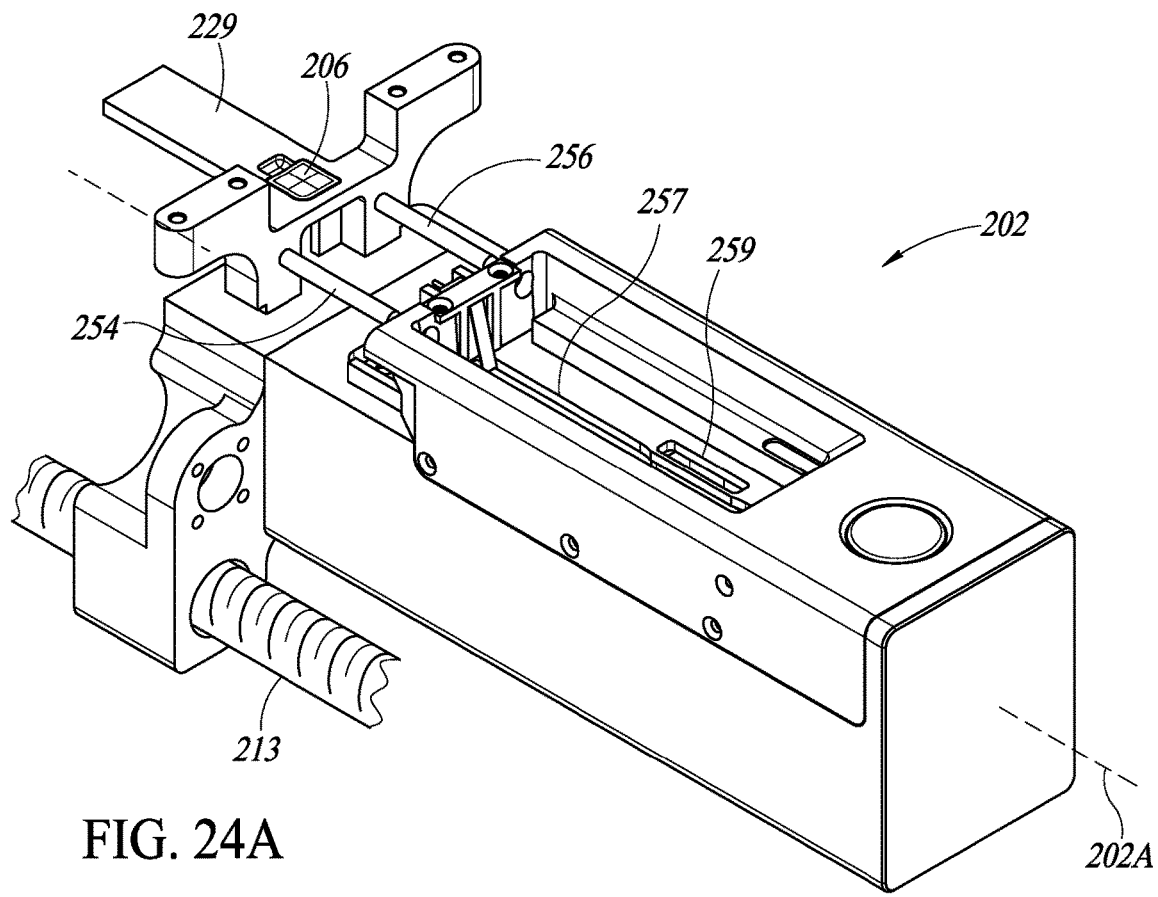
FIG. 24A is a front perspective view of the assay assembly's tray with its internal tray member in its insertion/ejection position relative to its external tray member.
Figure 24B:
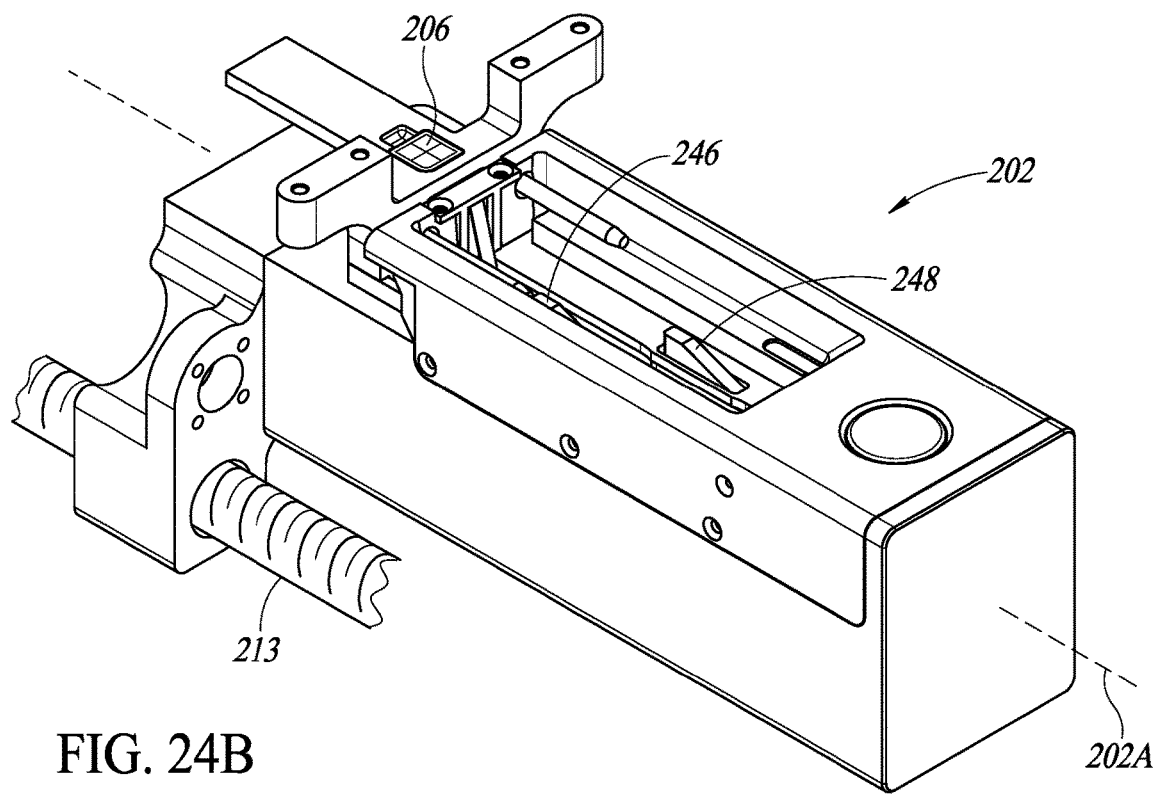
FIG. 24B is a front perspective view of the assay assembly's tray with its internal tray member in its actuated position relative to its external tray member.

FIGS. 23 and 24 show the tray 202 includes the following components: An external tray member 232 with the tray pocket 203 and the eject button 204A. An internal tray member 233 longitudinally slidingly reciprocal within the external tray member 232 between an assay device insertion/ejection position of an assay device 100 in the tray pocket 203 (see FIG. 24A) and an actuated assay device position of an assay device 100 in the tray pocket 203 (see FIG. 24B). And a restraining mechanism 234 for selectively restraining movement of the internal tray member 233 relative to the external tray member 232. On enabling the restraining mechanism 234, the internal tray member 233 is displaceable between its assay device insertion/ejection position and its assay device actuated position. On disabling the restraining mechanism 234, the internal tray member 233 is coupled to the external tray member 232 such that the internal tray member 233 moves in tandem with the external tray member 232 as driven by the drive shaft 213.

The external tray member 232 has opposite longitudinal surfaces 236 each having a leading minor cam surface 237 inclined with respect to the longitudinal tray centerline 202A and a trailing major surface 238 parallel thereto. The restraining mechanism 234 is constituted by an opposite pair of restraining members 239 acting against opposite longitudinal surfaces 236. The restraining members 239 are preferably spring biased by a pair of compression springs 241 having a non-compressed length L1 (see FIG. 21B) in the enabled state of the restraining mechanism 234 for restraining movement of the internal tray member 233 relative to the external tray member 233 and a fully compressed length L2<L1 (see FIG. 22B) in the disabled state of the restraining mechanism 234 for enabling the internal tray member 233 to move in tandem with the external tray member 232.

The external tray member 232 includes a major external tray member component 242 and a minor external tray member component 243 fixedly mounted on the major external tray member component 242. The major external tray member component 242 is fixedly mounted on the drive shaft 213. The minor external tray member component 243 includes the tray pocket 203. The internal tray member 233 is longitudinally slidingly reciprocal between the major external tray member component 242 and the minor external tray member component 243.

The major external tray member component 242 has a vacant interior for enabling backlighting an assay device 100. The major external tray member component 242 includes a longitudinal leading compartment 244 housing a leading specimen slide elevation member 246 and a longitudinal trailing compartment 247 housing a trailing specimen slide elevation member 248. The leading specimen slide elevation member 246 and the trailing specimen slide elevation member 248 are previously described as the leading specimen slide elevation member 161 and the specimen slide trailing elevation member 162 shown in FIG. 15A and FIG. 15B. The leading specimen slide elevation member 246 and the trailing specimen slide elevation member 248 are preferably spring biased but alternatively can be displaced by electro-mechanical means, for example, small electric motors, solenoids, and the like. The leading specimen slide elevation member 246 has a top leading specimen slide elevation member surface 249 with a horizontal leading surface 249A and an inclined trailing surface 249B. The trailing specimen slide elevation member 248 has a top trailing specimen slide elevation member surface 251 with a horizontal leading surface 251A and an inclined trailing surface 251B.

The compartments 244 and 247 are on opposite sides of the longitudinal tray centerline 202A thereby leaving the longitudinal tray centerline 202A unobstructed for scanning therealong. The leading specimen slide elevation member 246 is deployed for urging an assay device's central elevation support 158. The trailing specimen slide elevation member 248 is deployed for urging an assay device's trailing elevation support 159. The leading specimen slide elevation member 246 and the trailing specimen slide elevation member 248 together urge an assay device's specimen slide 104 from its initial lowermost specimen introduction position to its final uppermost specimen examination position. The leading specimen slide elevation member 246 and the trailing specimen slide elevation member 248 also couple the internal tray member 233 to the external tray member 232 such that the internal tray member 233 moves in tandem with the external tray member 232 as driven by the drive shaft 213.

The internal tray member 233 has a generally L-shaped construction including a leading headpiece 252 and a trailing elongated plate 253. The leading headpiece 252 includes the color target 206 and the second optical path shutter 229 extending inwards towards the second optical path 219. The headpiece 252 includes a right plunger 254 and a left plunger 256 in the direction of the trailing elongated plate 253 for correspondingly sliding insertion into an assay device's barrel right 131 and left barrel 132 for dispensing liquid reagent therefrom for reacting with bodily specimen in an internal tray member 233's assay device actuated position. The plungers 254 and 256 are previously described as the plungers 157A and 157B shown FIG. 14A and FIG. 14B.

The trailing elongated plate 253 includes a longitudinal elongated major slot 257 along the longitudinal tray centerline 202A for enabling backlight illumination therethrough for scanning purposes along the second optical path 219. The trailing elongated plate 253 includes a longitudinal leading slot 258 associated with the leading specimen slide elevation member 246 and a longitudinal trailing slot 259 associated with the trailing specimen slide elevation member 248. In the internal tray member's assay device insertion/ejection position, the leading specimen slide elevation member 246 and the trailing specimen slide elevation member 248 are in a blocked position under the plate 253. In the internal tray member's assay device actuated position, the leading specimen slide elevation member 246 and the trailing specimen slide elevation member 248 correspondingly exit through the leading slot 258 and the trailing slot 259.

On sliding displacement of the internal tray member 233 relative to the external tray member 232 from its assay device insertion/ejection position to its assay device actuated position, the inclined trailing surface 249B acts against the plate 253 to enable the leading specimen slide elevation member 246 to gradually exit through the leading slot 258. More importantly, on sliding displacement of the internal tray member 233 relative to the external tray member 232 from its actuated assay device position to its assay device insertion/ejection position, the inclined trailing surface 249B acts against the plate 253 for gradually depressing the leading specimen slide elevation member 246 for enabling its gradual travel under the plate 253 to its blocked position in the internal tray member 233's assay device insertion/ejection position.

Similarly on sliding displacement of the internal tray member 233 relative to the external tray member 232 from its assay device insertion/ejection position to its assay device actuated position, the inclined trailing surface 251B acts against the plate 253 to enable the trailing specimen slide elevation member 248 to gradually exit through the trailing slot 259. More importantly, on sliding displacement of the internal tray member 233 relative to the external tray member 232 from its actuated assay device position to its assay device insertion/ejection position, the inclined trailing surface 251B acts against the plate 253 for gradually depressing the trailing specimen slide elevation member 248 for enabling its gradual travel under the plate 253 to its blocked position in the internal tray member 233's assay device insertion/ejection position.

The assay apparatus 200 preferably includes a used assay device detector 261 for determining whether an assay device newly inserted in the tray pocket 203 is an unused assay device before operation of the assay apparatus 200 for acquiring diagnostic information. Such detection preferably involves determining whether a newly inserted assay device's built-in liquid reagent dispensing arrangement has been previously actuated. Such detection preferably compares one or more parameters of a newly inserted assay device to benchmark parameters for an unused assay device. One such benchmark parameter is the electric motor power consumption for initially displacing an assay device's leading seal since such displacement requires overcoming frictional forces for urging a seal along a barrel. An unused assay device requires a greater electric motor power consumption than a used assay device. Another approach is to optically detect the position of a newly inserted assay device's leading seals and/or trailing seals. A used assay device's leading seals and/or trailing seals are further along barrels than an unused assay device's leading seals and/or trailing seals.

The assay apparatus 200 preferably includes a UV light source 262 for killing bacteria within the apparatus housing 201.

Use of Assay System

The use of the assay system 10 is now described with reference to FIG. 25 to FIG. 37 for acquiring diagnostic information from an assay device 100. FIG. 25 to FIG. 37 show a complete cycle of operation of the assay apparatus 200 from insertion of a fresh assay device 100 to its ejection after diagnostic information has been acquired therefrom. After ejection of a spent assay device 100, the assay apparatus 200 is completely reset for insertion of a fresh assay device 100.

FIG. 25A to FIG. 37A are schematic longitudinal cross sections similar to FIG. 21A and FIG. 22A and similarly modified to show components which would otherwise not be shown in a longitudinal cross section along the longitudinal cross section line B-B. FIG. 25B to FIG. 37B are schematic transverse cross sections similar to FIG. 21B and FIG. 22B and similarly modified to show components which would otherwise not be shown in a transverse cross section along the transverse cross section line C-C.

Figure 25A:
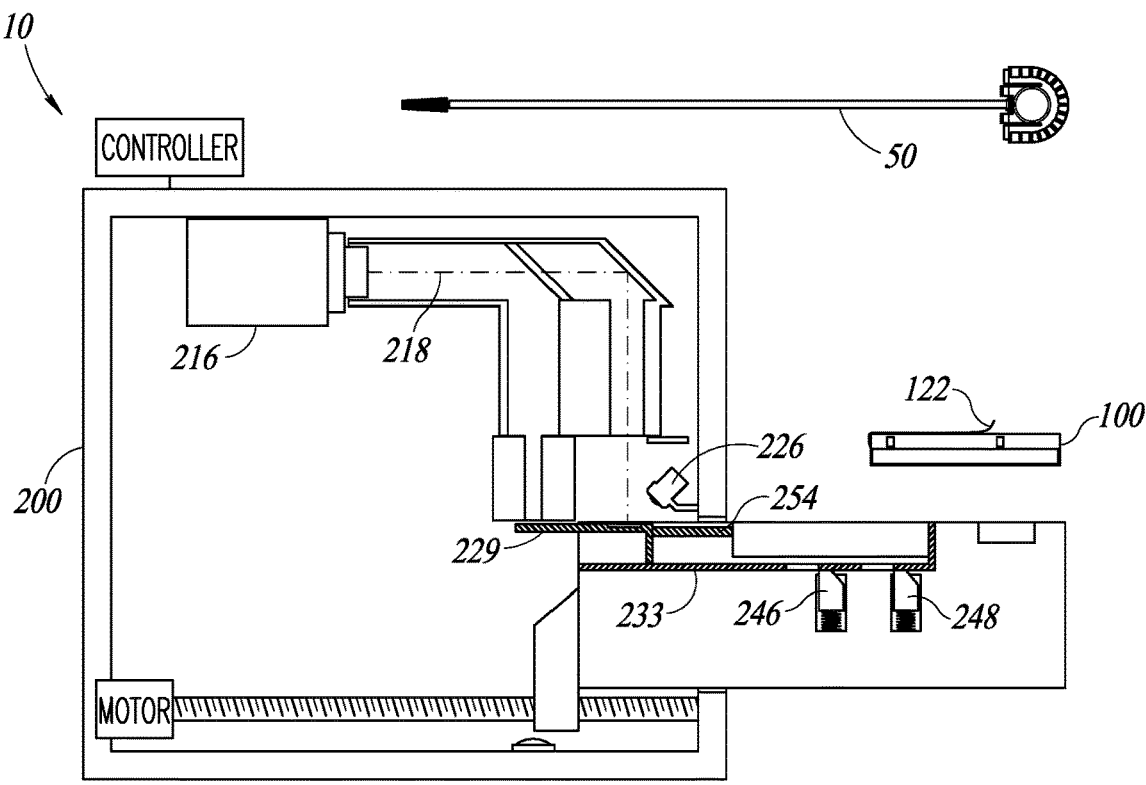
FIG. 25A is a schematic longitudinal cross section of the assay system with the assay apparatus' complete tray at its outermost position before insertion of an assay device therein.
Figure 25B:
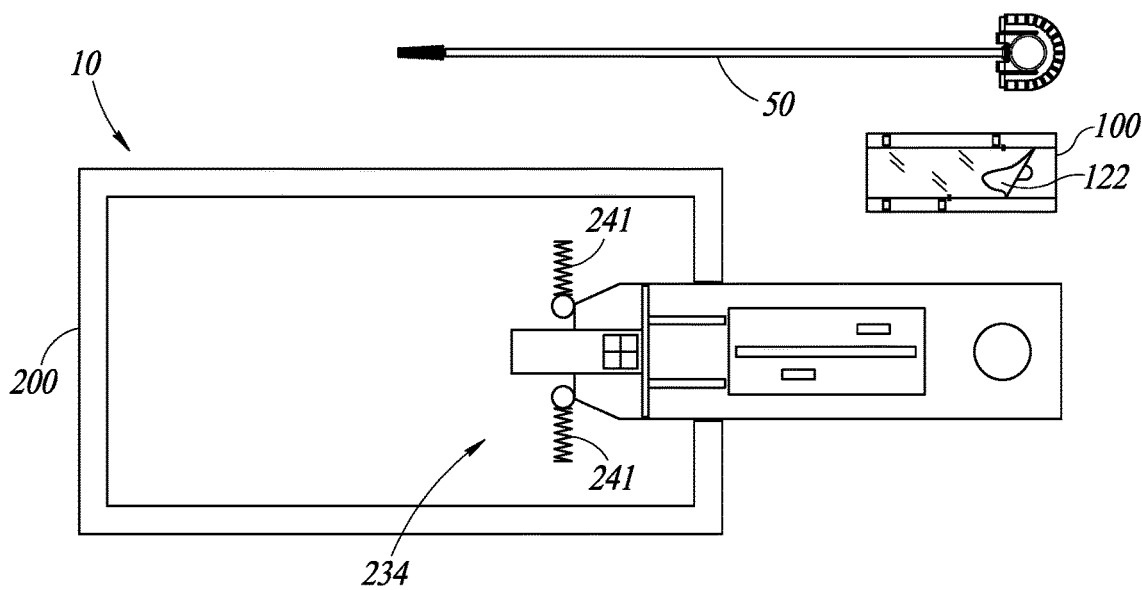
FIG. 25B is a schematic transverse cross section of the assay system with the assay apparatus' complete tray at its outermost position before insertion of an assay device therein.

FIG. 25A and FIG. 25B show the assay system 10 with the assay apparatus 200 having its tray 202 in its outermost position ready for insertion of a fresh assay device 100 in its tray pocket 203. The assay device 100 is suitably prepared by initially slidingly withdrawing its specimen collection tool 50 therethrough for smearing bodily specimen on its specimen slide 104 and subsequently removing its protective foil 122. The user enters information on the user interface 208 regarding a clinical procedure at hand, for example, patient details, and the like. Patient details include inter alia name, ID number, and age.

In the tray 202's outermost position, the assay apparatus 200 is set up as follows: The internal tray member 233 is in its assay device insertion/ejection position relative to the external tray member 232. The internal tray member 233 blocks the leading specimen slide elevation member 246 and the trailing specimen slide elevation member 248. The tray's color target 206 is disposed along the first optical path 218. The first optical path shutter 227 is open. The tray's second optical path shutter 229 closes the second optical path 219. The restraining mechanism 234 is enabled as evidenced by the compression springs at their fully non-compressed length L1 for restraining movement of the internal tray member 233 relative to the external tray member 232 such that the external tray member 232 can be displaced inward while the internal tray member 233 remains stationary.

Figure 26A:
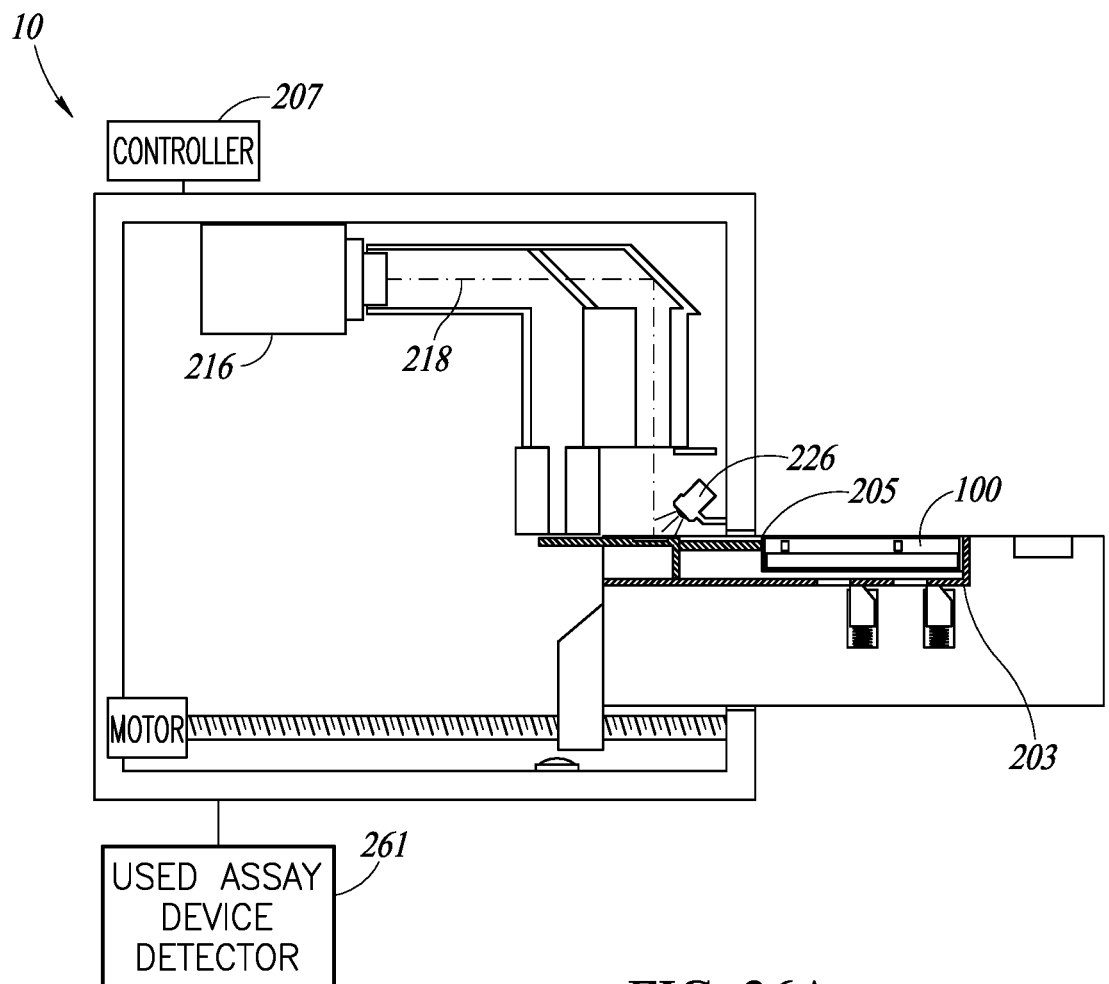
FIG. 26A is a schematic longitudinal cross section of the assay system with the assay apparatus' complete tray at its outermost position after insertion of the assay device therein.
Figure 26B:
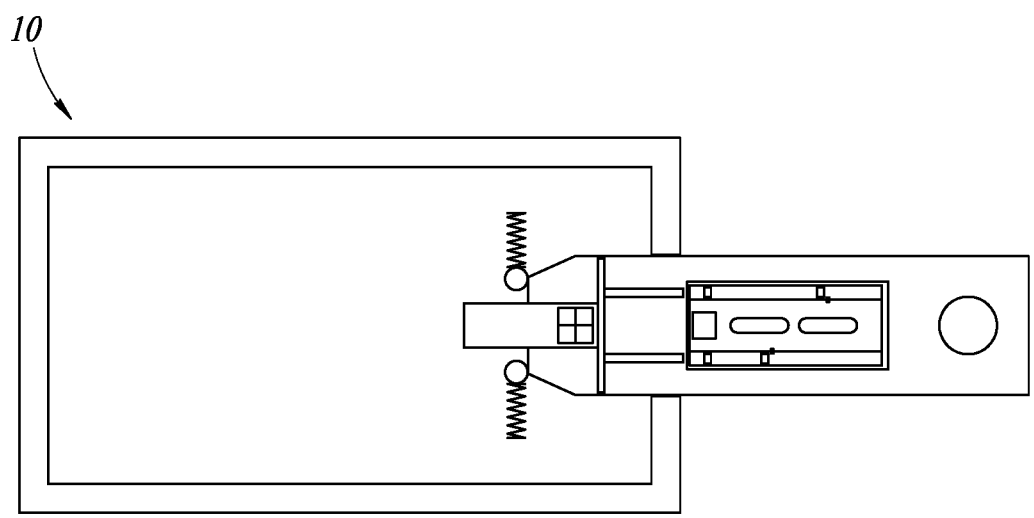
FIG. 26B is a schematic transverse cross section of the assay system with its assay apparatus' complete tray at its outermost position after insertion of the assay device therein.

FIG. 26A and FIG. 26B show the assay device 100 snugly inserted in the tray pocket 203 and if correctly inserted activates the micro-switch 205. The user presses the START button 209 and the assay apparatus 200 checks the assay device 100 has been correctly inserted in the tray pocket 203 and stops operation if the assay device 100 has been incorrectly inserted. If the assay device 100 has been incorrectly inserted, the assay apparatus 200 alerts the user. The used assay device detector 261 checks the assay device 100 is unused and issues an alert if the assay device 100 is a previously used assay device. The controller 207 switches on the illumination source 226 for illuminating the tray's color target 206 and the digital color camera 216 acquires a color target image along the first optical path 218. The illumination source 226 remains switched on until after the digital color camera 216 acquires a color pH reading image.

Figure 27A:
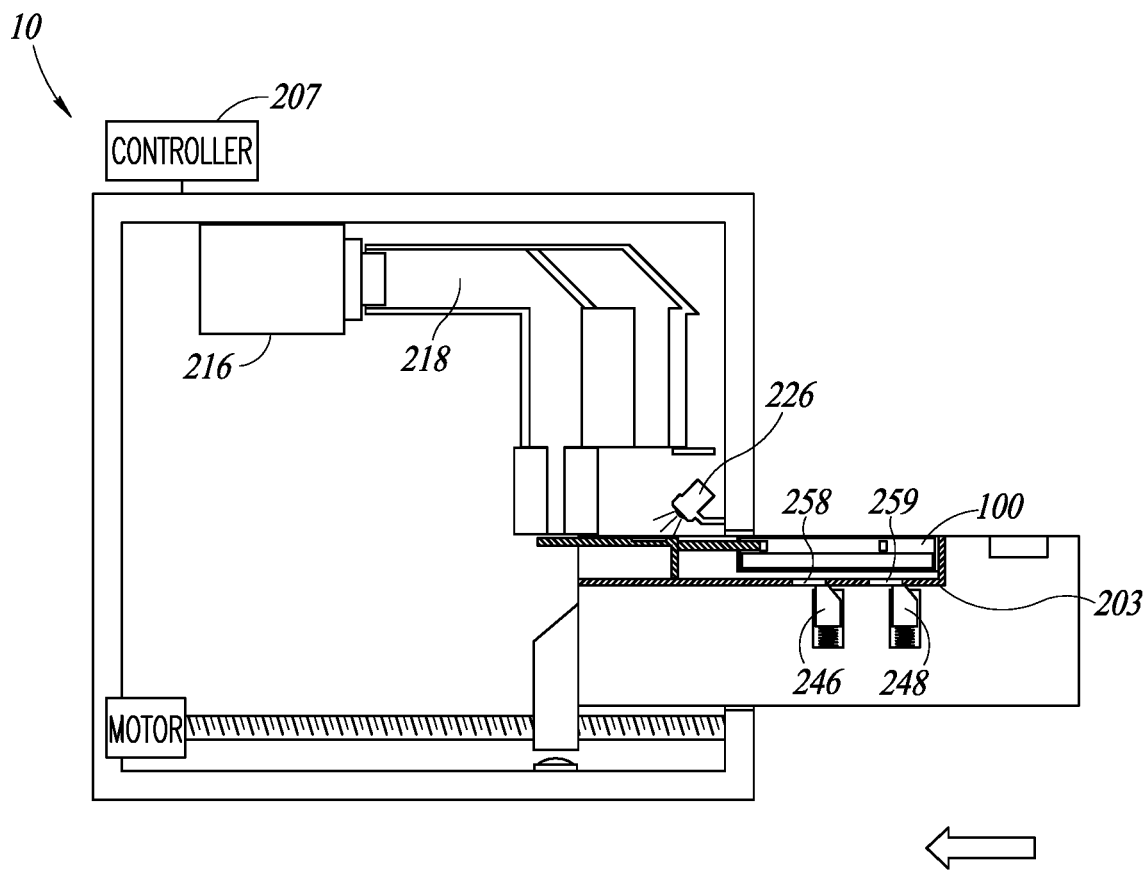
FIG. 27A is a schematic longitudinal cross section of the assay system showing an initial inward movement of the assay apparatus' external tray member relative to its stationary internal tray member.
Figure 27B:
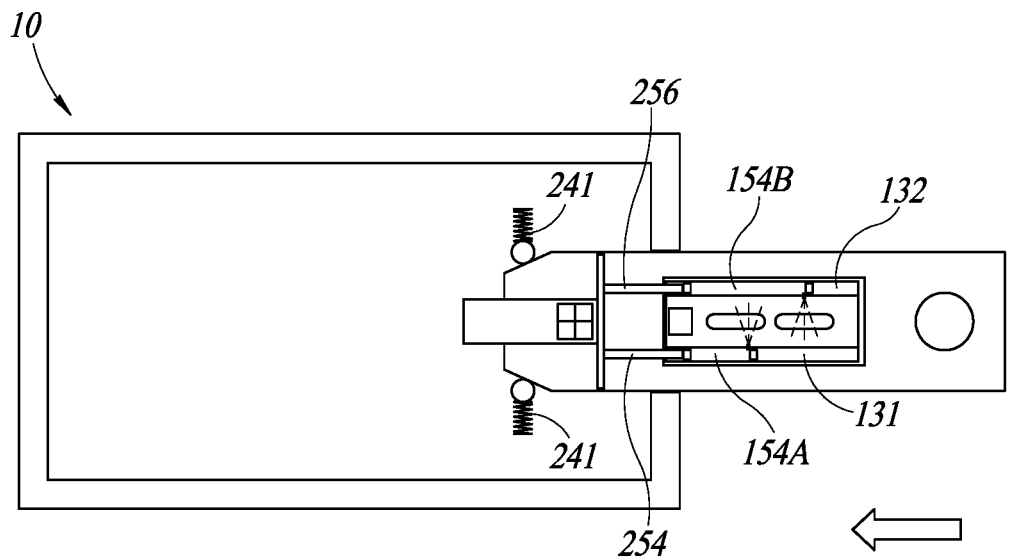
FIG. 27B is a schematic transverse cross section of the assay system showing initial an inward movement of the assay apparatus' external tray member relative to its stationary internal tray member.

FIG. 27A and FIG. 27B show an initial inward movement of the external tray member 232 relative to the stationary internal tray member 233 which leads to the following simultaneous actions: The plungers 254 and 256 correspondingly enter the barrels 131 and 132 for dispensing liquid reagent 154A on the central work surface 146 and the liquid reagent 154B on the trailing work surface 147. The leading elevation member 246 approaches the slot 258. The trailing elevation member 248 approaches the slot 259. The compression springs 241 begin to be compressed.

Figure 28A:
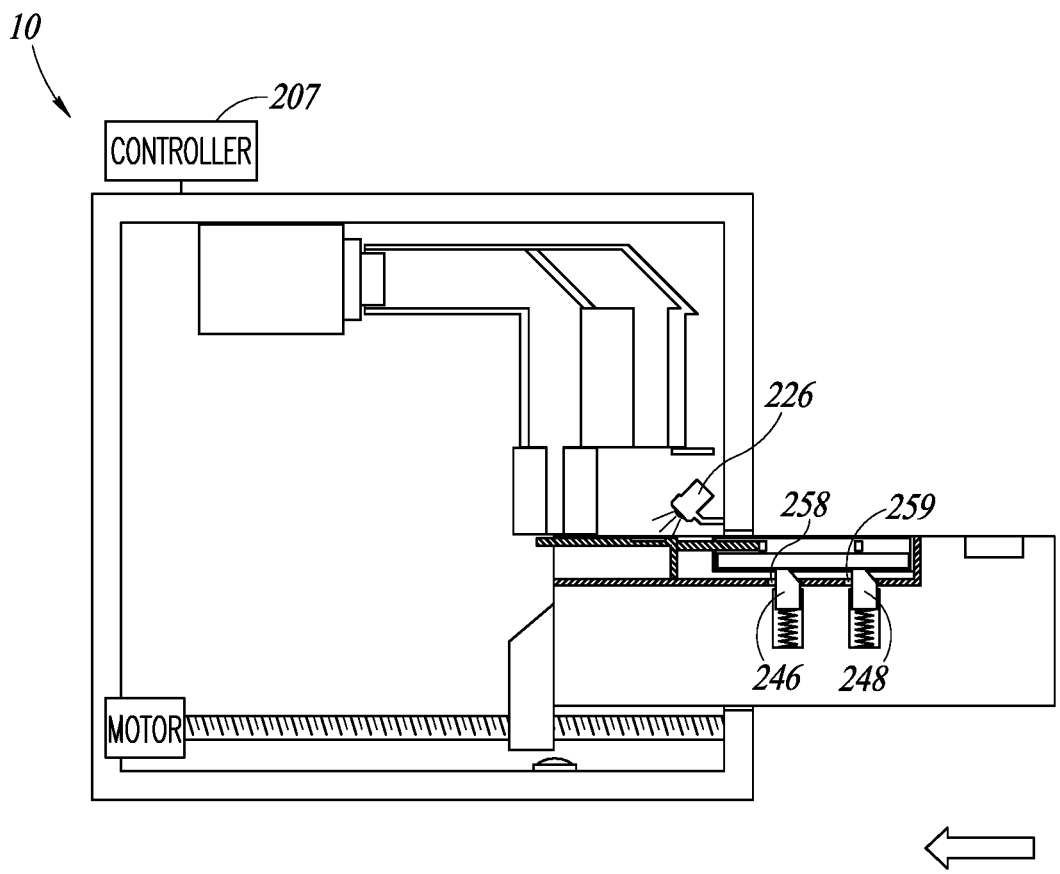
FIG. 28A is a schematic longitudinal cross section of the assay system showing continuing inward movement of the assay apparatus' external tray member relative to its stationary internal tray member.
Figure 28B:
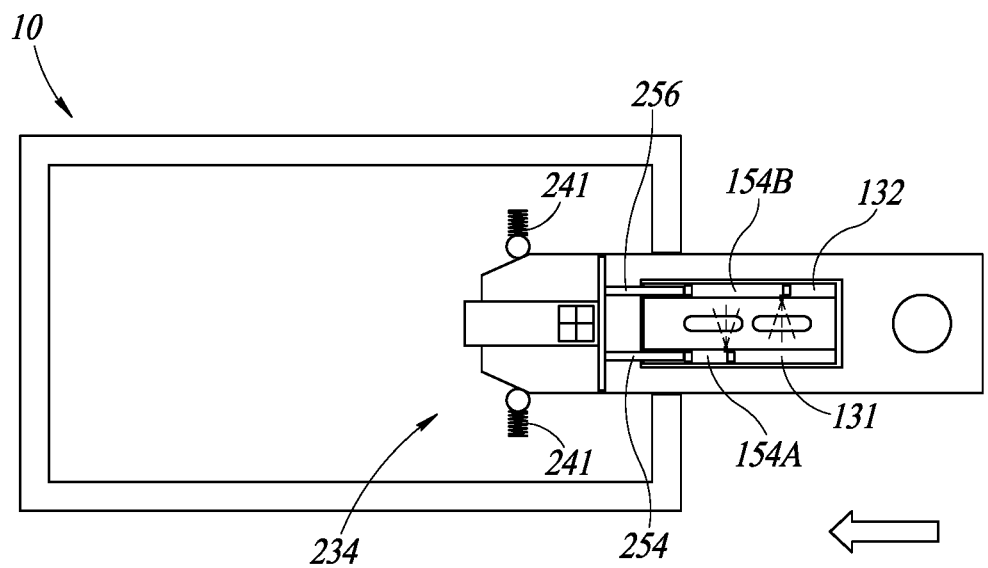
FIG. 28B is a schematic transverse cross section of the assay apparatus showing continuing inward movement of the assay apparatus' external tray member relative to its stationary internal tray member.

FIG. 28A and FIG. 28B show continuing inward movement of the external tray member 232 relative to the stationary internal tray member 233 which leads to the following simultaneous actions: The plungers 254 and 256 continue dispensing liquid reagent 154A and liquid reagent 154B. The leading specimen slide elevation member 246 starts upwardly exiting through the leading slot 258 into the tray pocket 203. The trailing specimen slide elevation member 248 starts upwardly exiting through the trailing slot 259 into the tray pocket 203. The compression springs 241 are further compressed towards disabling the restraining mechanism 234.

Figure 29A:
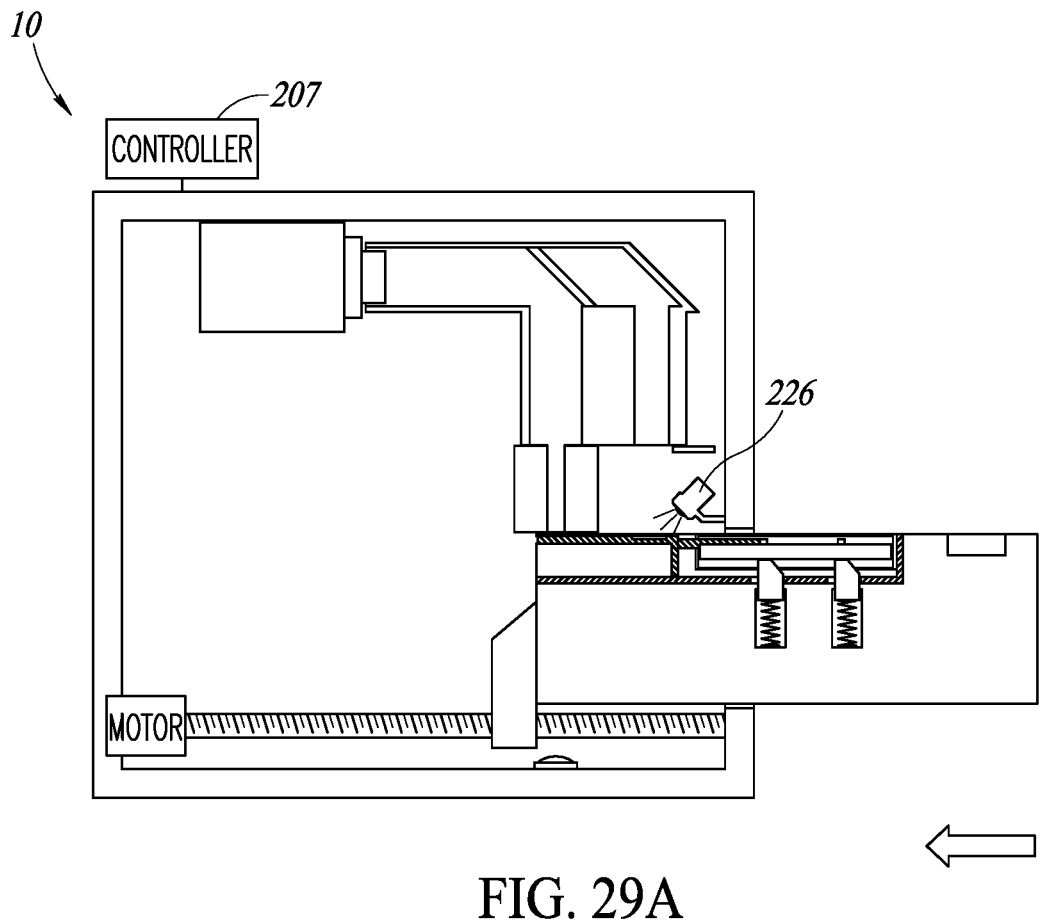
FIG. 29A is a schematic longitudinal cross section of the assay system showing continuing inward movement of the assay apparatus' external tray member relative to its stationary internal tray member.
Figure 29B:
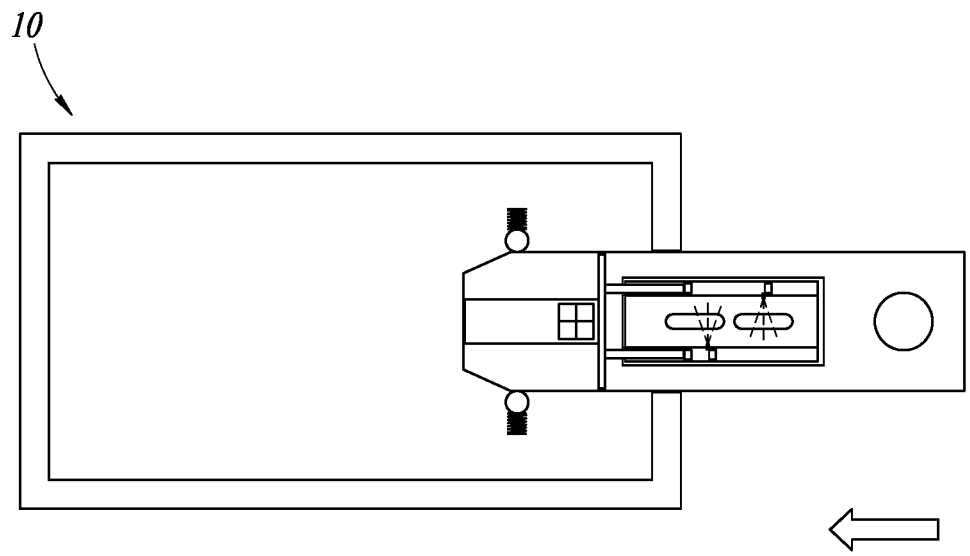
FIG. 29B is a schematic transverse cross section of the assay system showing continuing inward movement of the assay apparatus' external tray member relative to its stationary internal tray member.

FIG. 29A and FIG. 29B show continuing inward movement of the external tray member 232 relative to the stationary internal tray member 233 to the instant immediately before the restraining mechanism 234 is disabled as evidenced by compression of the compression springs 241 to their fully compressed length L2. Disablement of the restraining mechanism 234 enables coupling of the internal tray member 233 to the external tray member 232 for continuing inward movement of the complete tray 202, namely, both external tray member 232 and the internal tray member 233 in tandem. The internal tray member 233 is in its actuated assay device position relative to the external tray member 232 insofar as the leading specimen slide elevation member 246 further upwardly exits through the leading slot 258 and the trailing specimen slide elevation member 248 further upwardly exits through the trailing slot 259 into the tray pocket 203 to latch the internal tray member 233 to the external tray member 232 for enabling their combined continuing inward movement and upwardly urge the assay device's specimen slide 104 towards its final uppermost specimen examination position.

Figure 30A:
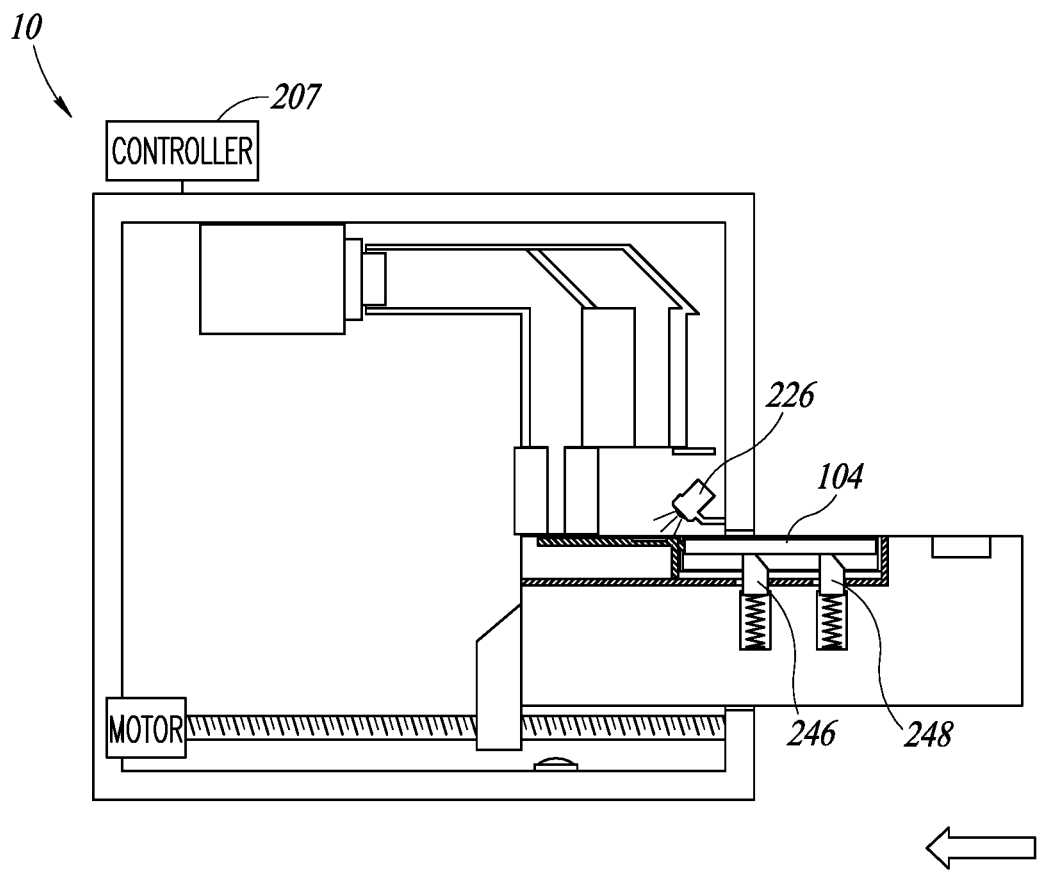
FIG. 30A is a schematic longitudinal cross section of the assay system showing continuing inward movement of the assay apparatus' complete tray towards its innermost position.
Figure 30B:
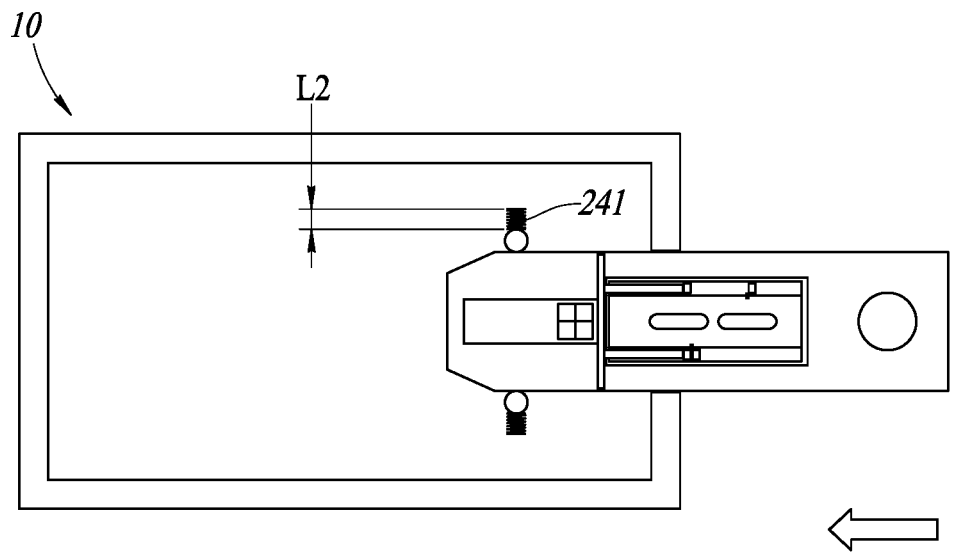
FIG. 30B is a schematic transverse cross section of the assay system showing continuing inward movement of the assay apparatus' complete tray towards its innermost position.

FIG. 30A and FIG. 30B show continuing inward movement of the complete tray 202 which leads to the leading specimen slide elevation member 246 completely exiting through the leading slot 258 and the trailing specimen slide elevation member 248 completely exiting through the trailing slot 259 into the tray pocket 203 to fully upwardly urge the assay device's specimen slide 104 into its final uppermost specimen examination position.

Figure 31A:
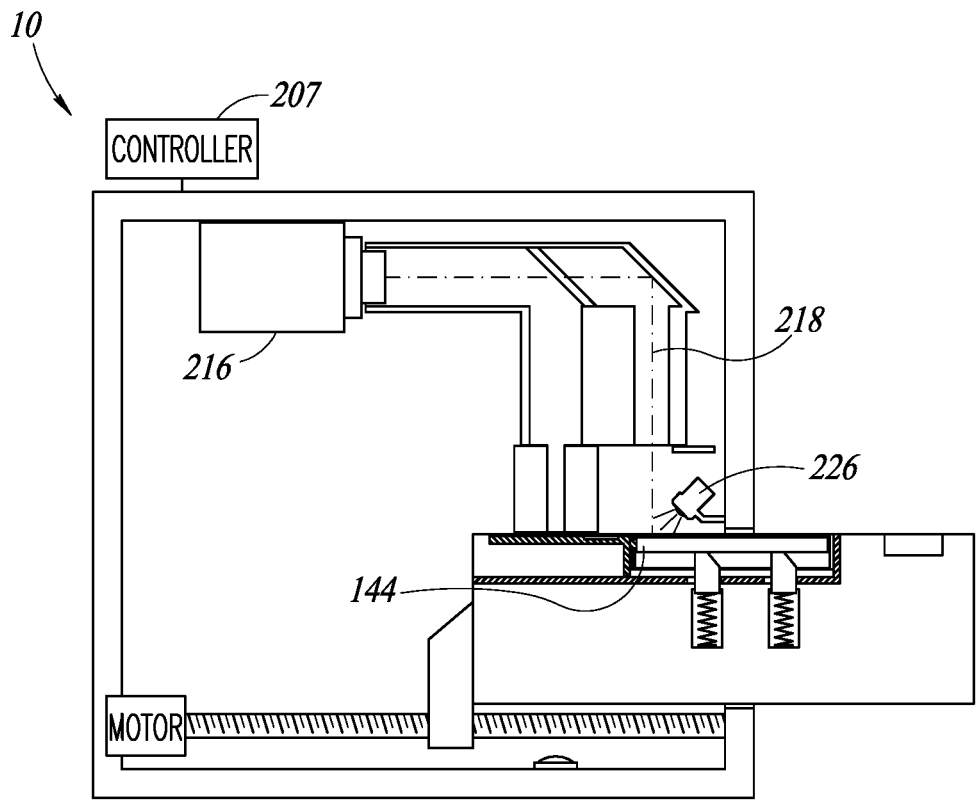
FIG. 31A is a schematic longitudinal cross section of the assay system showing continuing inward movement of the assay apparatus' complete tray towards its innermost position.
Figure 31B:
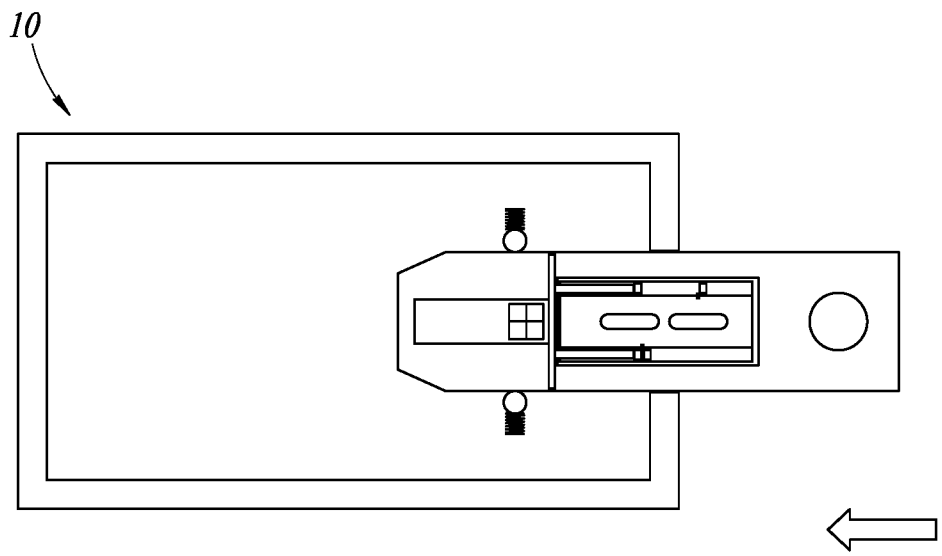
FIG. 31B is a schematic transverse cross section of the assay system showing continuing inward movement of the assay apparatus' complete tray towards its innermost position.

FIG. 31A and FIG. 31B show continuing inward movement of the complete tray 202 until the assay device 100's pH detection surface 144 is disposed along the first optical path 218. The digital color camera 216 acquires a color pH reading image. The controller 207 switches off the illumination source 226.

Figure 32A:
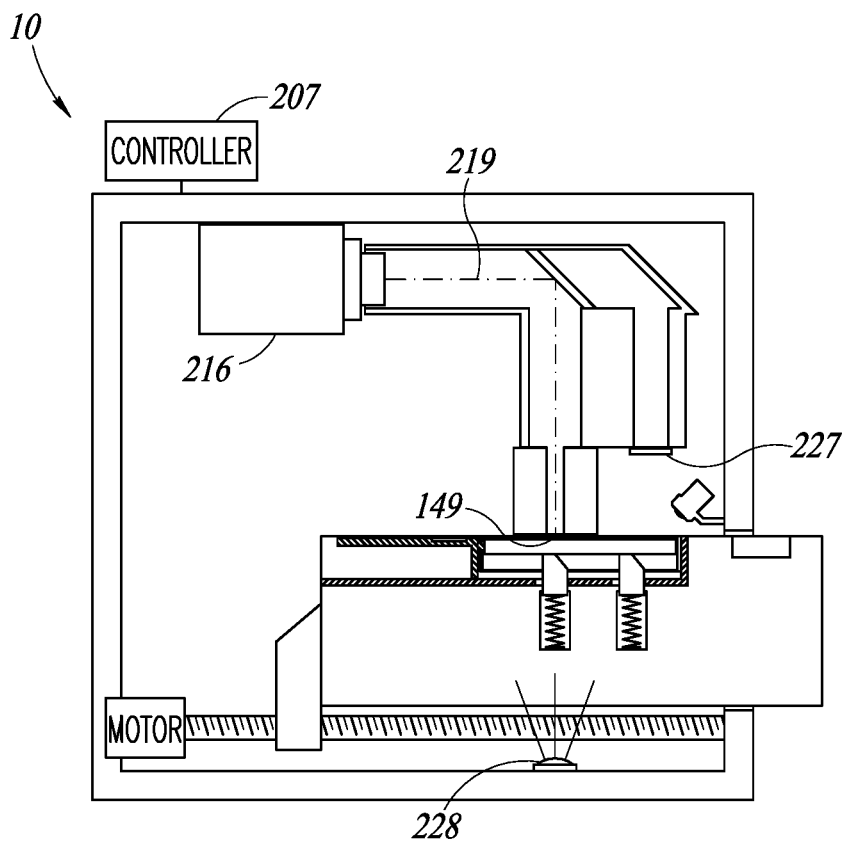
FIG. 32A is a schematic longitudinal cross section of the assay system showing continuing inward movement of the assay apparatus' complete tray towards its innermost position.
Figure 32B:
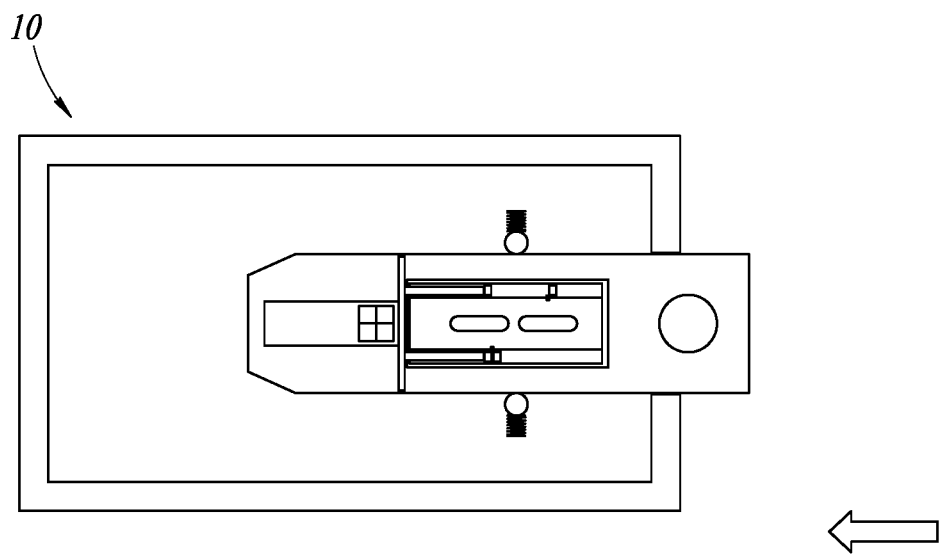
FIG. 32B is a schematic transverse cross section of the assay system showing continuing inward movement of the assay apparatus' complete tray towards its innermost position.

FIG. 32A and FIG. 32B show continuing inward movement of the assay apparatus' complete tray 202 until the assay device 100's target 148A is disposed along the second optical path 219. The continuing inward movement leads to the following simultaneous actions: The controller 207 switches on the illumination source 228 for backlighting the assay device 100. The first optical path shutter 227 closes the first optical path 218 to preclude illumination reaching the color camera 216 via the first optical path 218. The digital color acquisition arrangement 214 focuses the color camera 216 on the target 148A backlighted by the illumination source 228 ready to start acquiring microscope images of bodily specimen reacted with the liquid reagent 154A on the specimen slide panel 148.

Figure 33A:
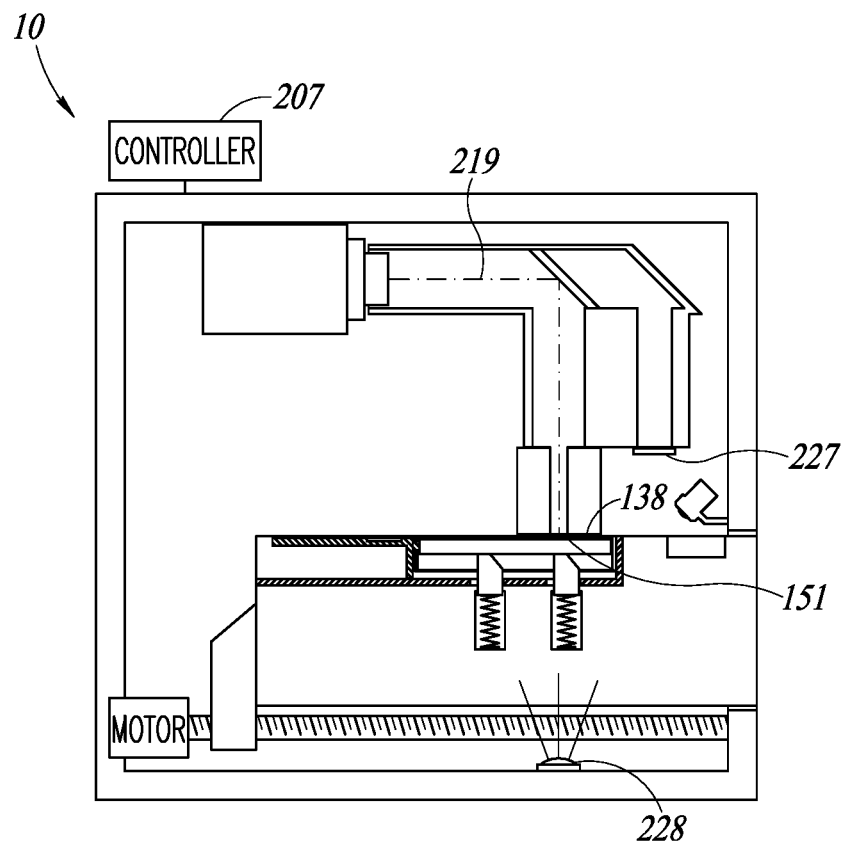
FIG. 33A is a schematic longitudinal cross section of the assay system showing the assay apparatus' complete tray at its innermost position.
Figure 33B:
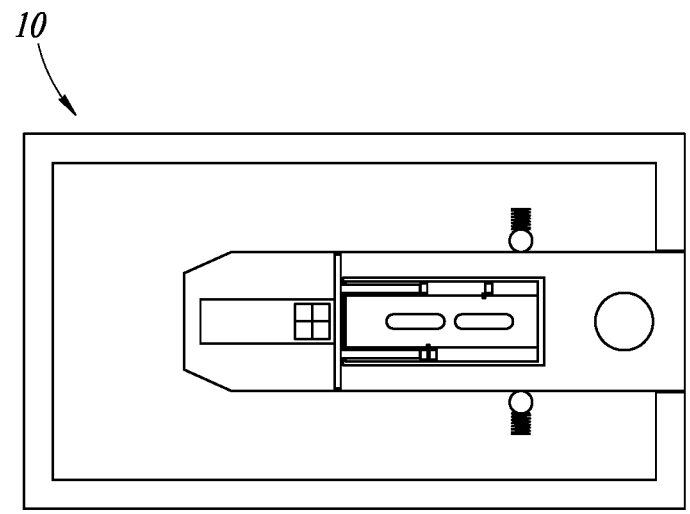
FIG. 33B is a schematic transverse cross section of the assay system showing assay apparatus' complete tray at its innermost position.

FIG. 33A and FIG. 3B show the tray 202 at its innermost position. During continuous inward movement of the complete tray 202 to its innermost position, the following actions took place: The color camera 216 acquires a series of microscope images of bodily specimen reacted with the liquid reagent 154A on the specimen slide panel 148 as the specimen slide panel 148 passes along under the second optical path 219. The bodily specimen on the specimen slide panel 148 is backlighted by illumination from the illumination source 228 passing through the major external tray member component 242 and the longitudinal slot 257.

As the assay device 100's target 151A is disposed along the second optical path 219, the digital color acquisition arrangement 214 focuses the color camera 216 on the target 151A ready to start acquiring microscope images of bodily specimen reacted with the liquid reagent 154B on the specimen slide panel 151.

The color camera 216 acquires a series of microscope images of bodily specimen reacted with the liquid reagent 154B on the specimen slide panel 151 as the specimen slide panel 151 passes along under the second optical path 219. The bodily specimen on the specimen slide panel 151 is backlighted by illumination from the illumination source 228 passing through the major external tray member component 242 and the longitudinal slot 257.

The illumination source 228 is switched off.

Figure 34A:
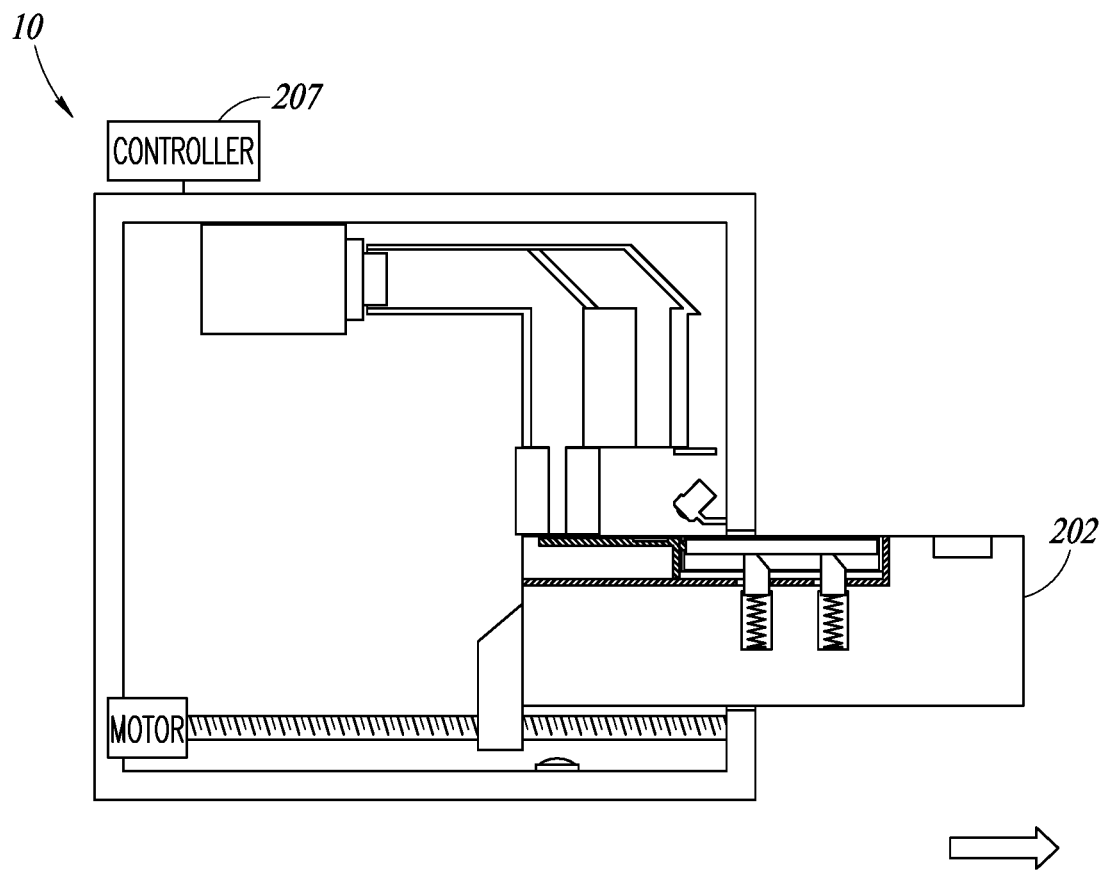
FIG. 34A is a schematic longitudinal cross section of the assay system showing outward movement of the assay apparatus' complete tray until a start of outward movement of the assay apparatus' external tray member relative to its stationary internal tray member.
Figure 34B:
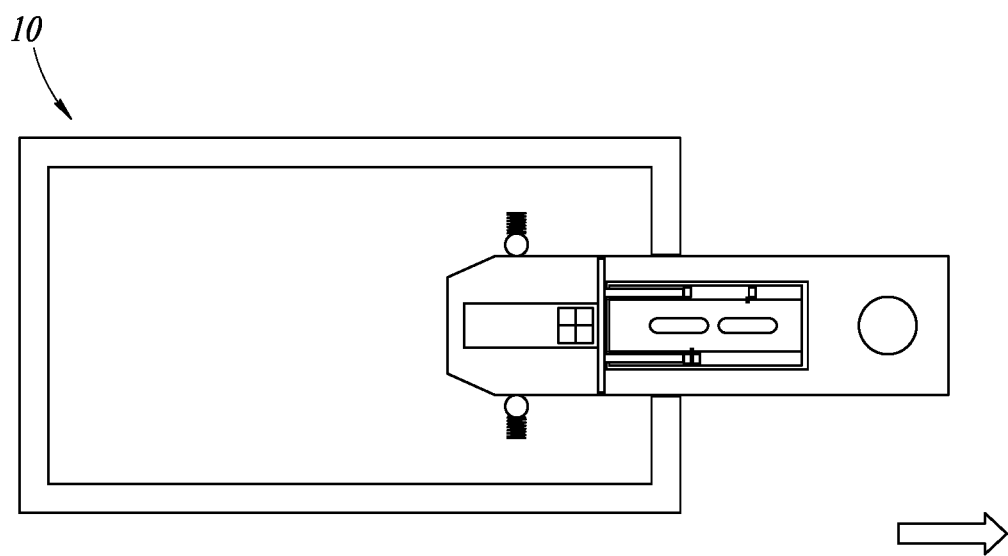
FIG. 34B is a schematic transverse cross section of the assay system showing outward movement of the assay apparatus' complete tray until a start of outward movement of the assay apparatus' external tray member relative to its stationary internal tray member.

FIG. 34A and FIG. 34B show outward movement of the complete tray 202 until a start of decoupling of the internal tray member 233 from the external tray member 232 to enable continued outward movement of the external tray member 232 relative to the internal tray member 233 such that the internal tray member 233 can be reset to its assay device insertion/ejection position. The first optical path shutter 227 is opened.

Figure 35A:
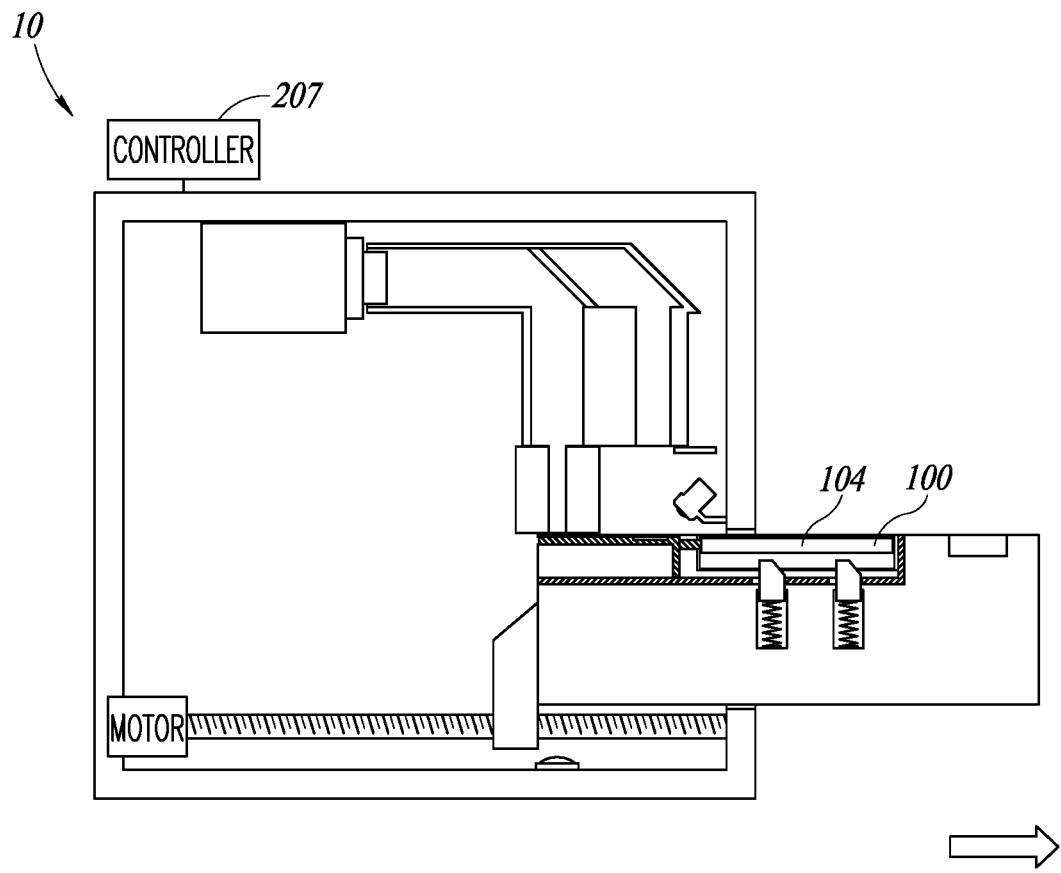
FIG. 35A is a schematic longitudinal cross section of the assay system showing outward movement of the assay apparatus' external tray member relative to its stationary internal tray member.
Figure 35B:
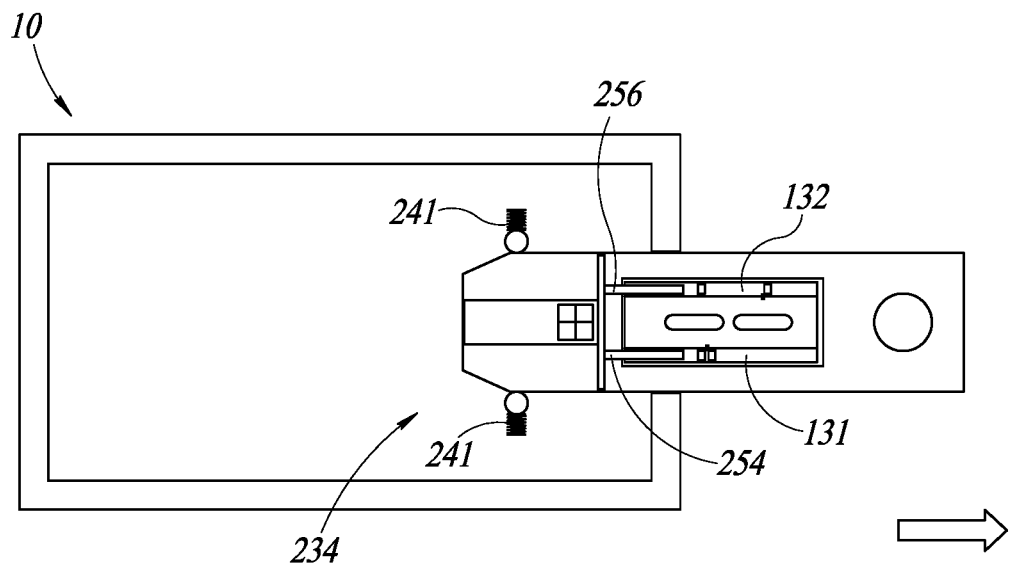
FIG. 35B is a schematic transverse cross section of the assay system showing outward movement of the assay apparatus' external tray member relative to its stationary internal tray member.

FIG. 35A and FIG. 35B show outward movement of the external tray member 232 relative to the stationary internal tray member 233. The restraining mechanism 234 starts to be enabled as evidenced by the compression springs 241 beginning to extend from their fully compressed length L2. The internal tray member 233 begins to depress the leading specimen slide elevation member 246 and the trailing specimen slide elevation member 248 thereunder. The plungers 254 and 256 begin to leave the barrels 131 and 132. The assay device's specimen slide 104 remains in its final uppermost specimen examination position by virtue of its specimen slide securing arrangement 105 thereby precluding its reuse.

Figure 36A:
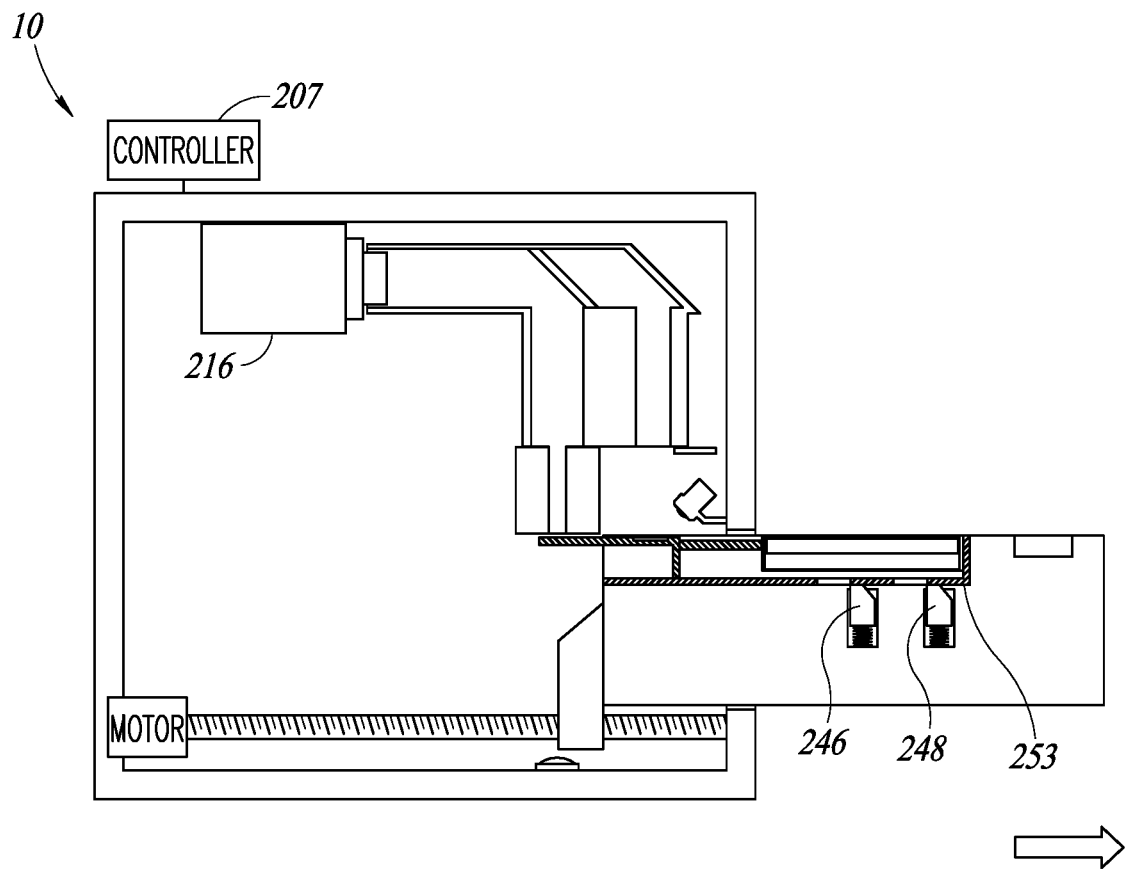
FIG. 36A is a schematic longitudinal cross section of the assay system with the assay apparatus' complete tray at its outermost position.
Figure 36B:
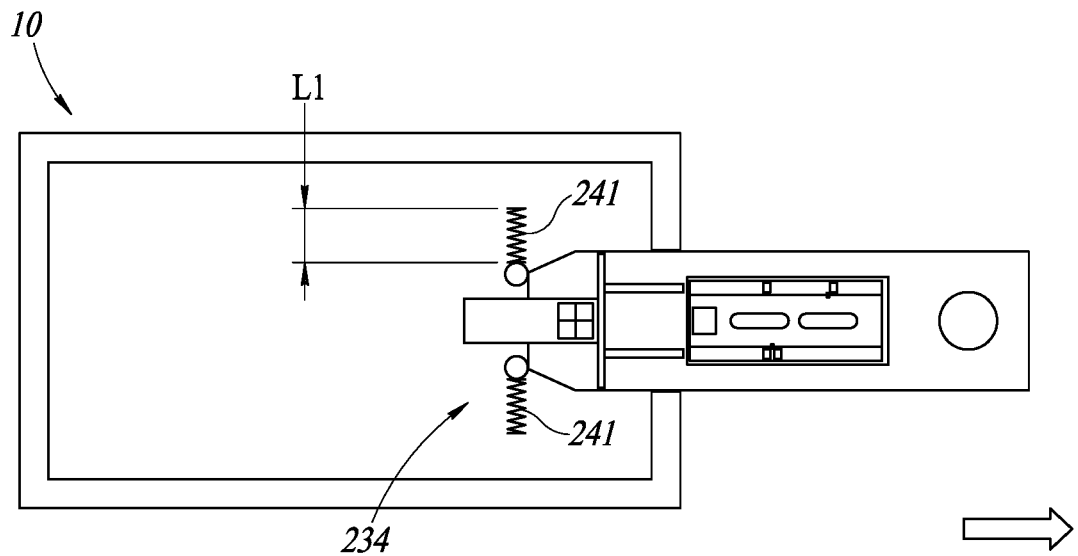
FIG. 36B is a schematic transverse cross section of the assay system with the assay apparatus' complete tray at its outermost position.

FIG. 36A and FIG. 36B show the assay system 10 with the tray 202 at the same outermost position as shown in FIG. 25A and FIG. 25B thereby completing a full cycle of operation of the assay apparatus 200 for obtaining diagnostic information from the assay device 100. The restraining mechanism 234 is fully enabled as evidenced by the compression springs 241 at their fully non-compressed length L1. The leading specimen slide elevation member 246 and the trailing specimen slide elevation member 248 are blocked by the plate 253. In the tray's outermost position, the internal tray member 233 is in its assay device insertion/ejection position relative to the external tray member 232.

Figure 37A:
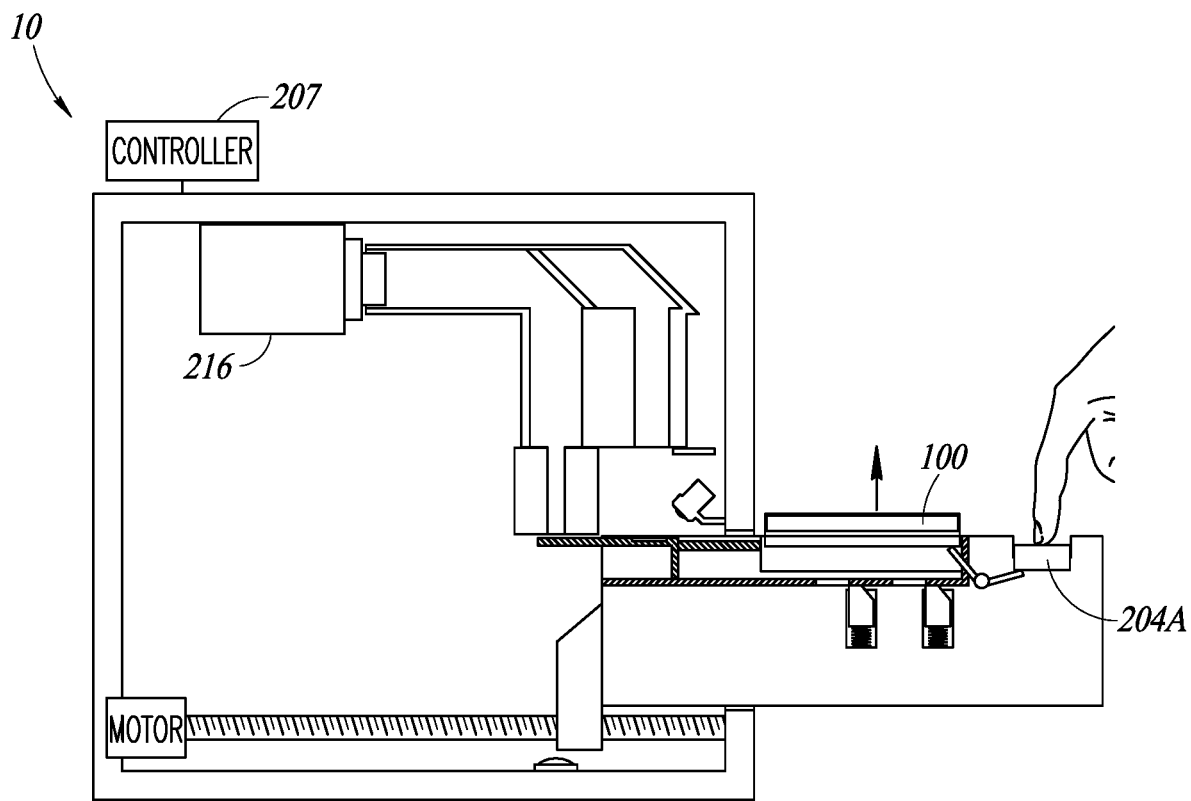
FIG. 37A is a schematic longitudinal cross section of the assay system showing ejection of the assay device from the assay apparatus' tray pocket at its complete tray's outermost position.
Figure 37B:
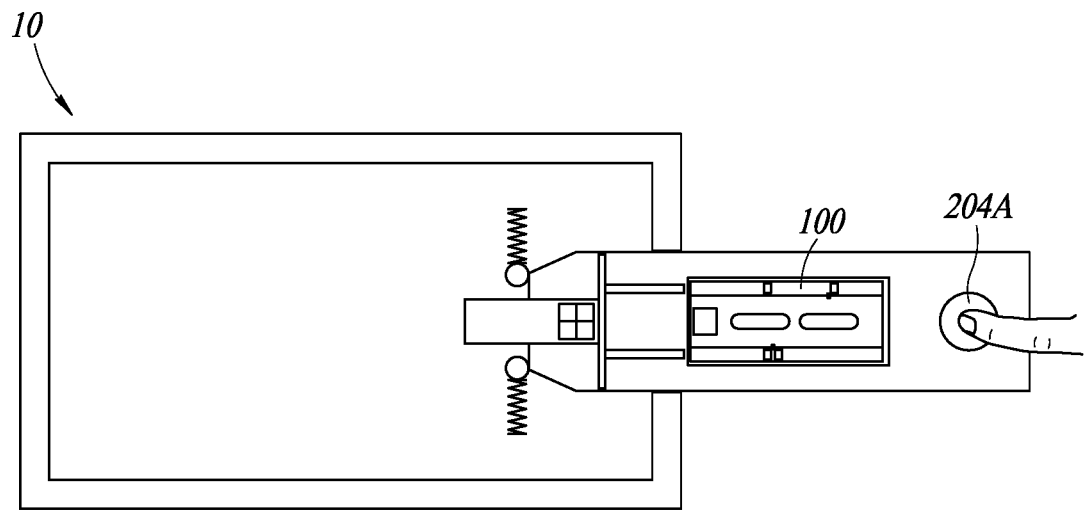
FIG. 37B is a schematic transverse cross section of the assay system showing ejection of the assay device from the assay apparatus' tray pocket at its complete tray's outermost position.

FIG. 37A and FIG. 37B show ejection of the assay device 100 from the tray pocket 203 on manual depression of the eject button 204A. The spent assay device 100 can be safely discarded. The assay apparatus 200 is reset to snugly receive a fresh assay device 100 in its tray pocket 203.

Figure 38:
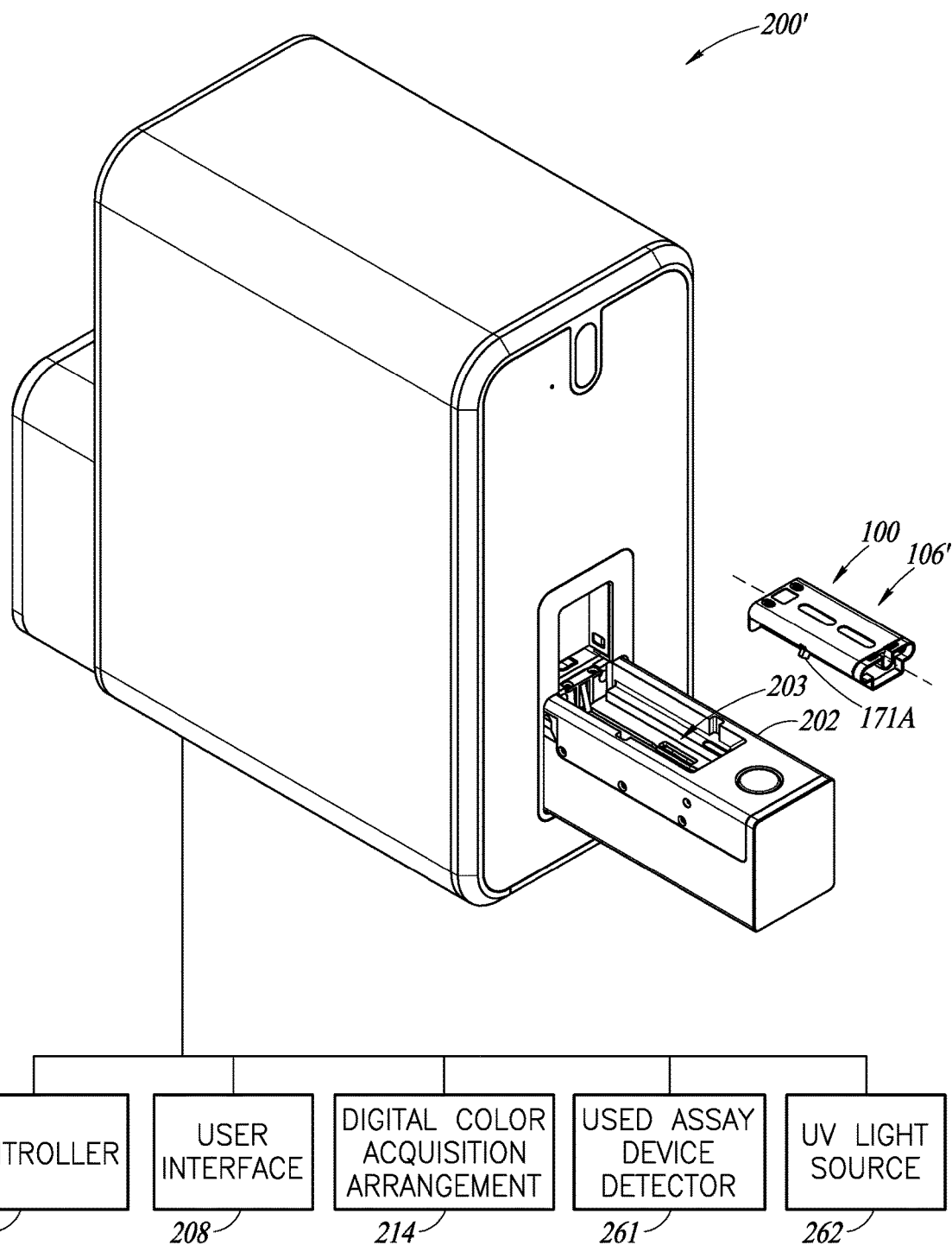
FIG. 38 is a combined perspective view and block diagram of assay apparatus for use with the FIG. 16 assay device.
Figure 39:
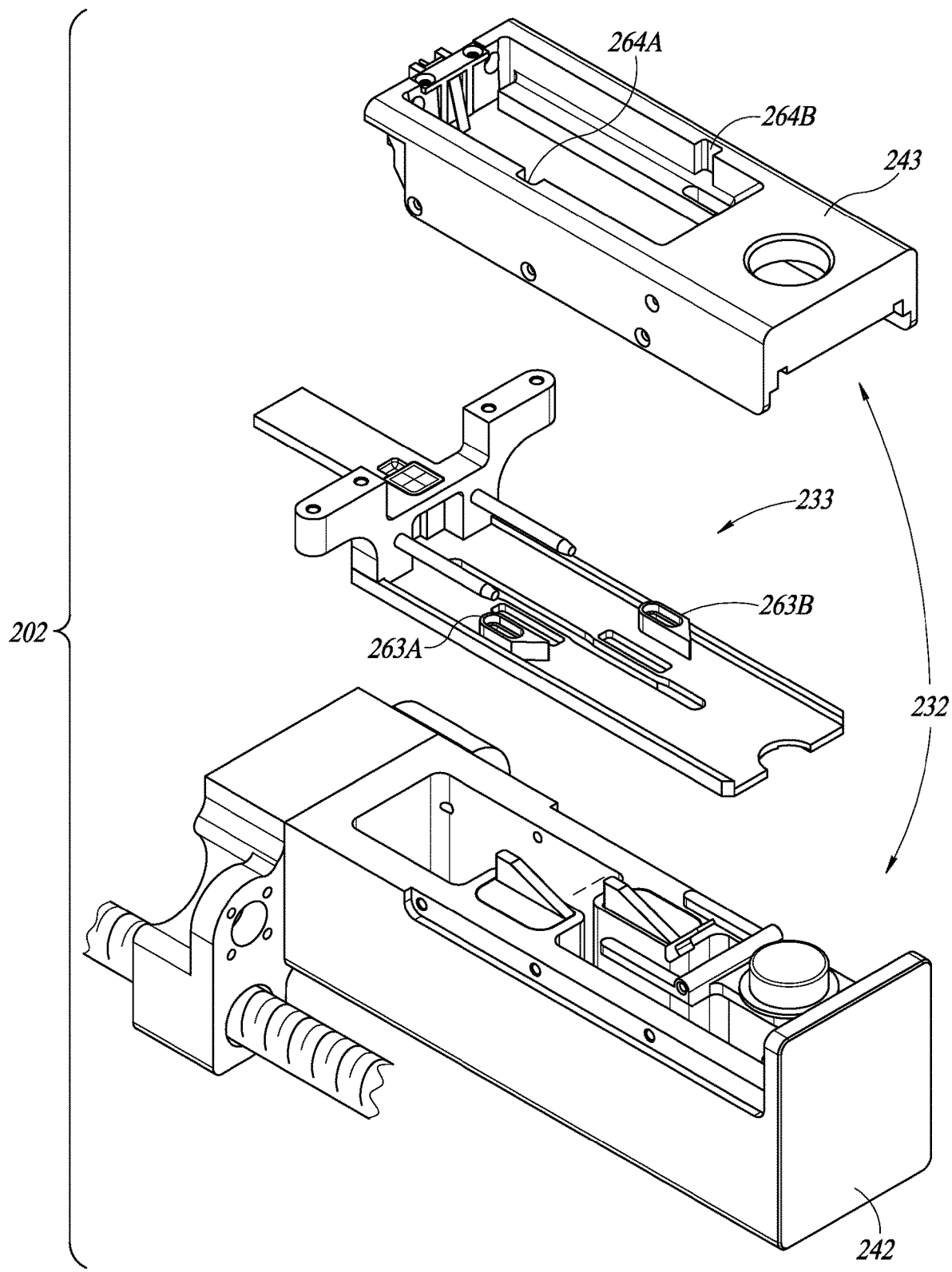
FIG. 39 is an exploded view of Figure assay assembly's tray for use with the FIG. 16 built-in liquid reagent dispensing arrangement.

FIG. 38 and FIG. 39 show an assay apparatus 200' for use with assay devices 100 having a built-in liquid reagent dispensing arrangement 106'. The assay apparatus 200' has a similar construction as the assay apparatus 200 and therefore similar parts are likewise numbered. The assay apparatus 200' differs from the assay apparatus 200 in two respects as follows: First, the internal tray member 233 includes a pair of stopcock actuators 263A and 263B described hereinabove as the stopcock actuators 190A and 190B (see FIG. 16 to FIG. 19B) for actuating an assay device's stopcocks 168A and 168B. And second, the minor external tray member component 243 includes a pair of cutouts 264A and 264B for correspondingly receiving an assay device's stopcock actuation tabs 171A and 171B after actuation of the stopcocks 168A and 168B to their liquid reagent dispensing position. The assay apparatus 200' has the same operation as assay apparatus 200 except that its stopcock actuators 263A and 263B open an assay device's stopcocks 168A and 168B for liquid reagent dispensing purposes.

While the invention has been described with respect to a limited number of embodiments, it will be appreciated that many variations, modifications, and other applications of the invention can be made within the scope of the appended claims.

The invention claimed is:

1. A handheld assay device for use with a handheld specimen collection tool having a shank, a handle and a specimen collection tip for bearing a bodily specimen, the assay device enabling ElectroMagnetic Radiation (EMR) examination of the bodily specimen at at least one predetermined EMR wavelength, the assay device having a longitudinal assay device centerline and comprising:

(a) a cartridge housing including a cartridge housing top face, a cartridge housing bottom face opposite said cartridge housing top face, and a cartridge housing peripheral face between said cartridge housing top face and said cartridge housing bottom face to bound a cartridge housing interior,
said cartridge housing bottom face including at least one throughgoing aperture for providing access to said cartridge housing interior,
said cartridge housing peripheral face include an opposite pair of major side faces co-directional with said longitudinal assay device centerline, and an opposite pair of minor end faces transverse to said longitudinal assay device centerline, said opposite pair of minor end faces includes a leading minor end face and a trailing minor end face,
said cartridge housing peripheral face includes a specimen collection tip throughgoing aperture for providing access to said cartridge housing interior to the specimen collection tip;

(b) a specimen slide snugly accommodated in said cartridge housing interior and slidingly deployable from an initial lowermost specimen introduction position in an unused assay device to a final uppermost specimen examination position in an used assay device, said initial lowermost specimen introduction position and said final uppermost specimen examination position correspondingly remote from and adjacent said cartridge housing top face,
said cartridge housing top face and said specimen slide correspondingly have at least one cartridge housing top face panel and at least one specimen slide panel in registration for defining a line of examination through the assay device, said at least one cartridge housing top face panel and said at least one specimen slide panel being transparent at an EMR wavelength of the at least one predetermined EMR wavelength,
said specimen slide panel being intimately juxtaposed against said cartridge housing top face panel in said actuated state of the assay device; and (c) a built-in liquid reagent dispensing arrangement for dispensing a liquid reagent on said at least one specimen slide panel, said built-in liquid reagent dispensing arrangement including at least one longitudinal directed barrel lateral to said longitudinal assay device centerline,
each said barrel including an exposed leading seal towards said leading minor end face and a trailing seal member disposed towards said trailing minor end face,
each said barrel including liquid reagent between said leading seal and said trailing seal member,
each said barrel having a liquid reagent dispensing port for dispensing liquid reagent on a corresponding specimen slide of said at least one specimen slide panel,
said leading seal having an initial pre-liquid reagent dispensing position in an unused assay device and a liquid reagent dispensing position,
said leading seal being urged along said barrel from said initial pre-liquid reagent dispensing position to said liquid reagent dispensing position,
said trailing seal member being a stopcock permanently deployed at said liquid reagent dispensing port and urged to rotate from a closed position at said initial pre-liquid reagent dispensing position to an open position at said liquid reagent dispensing position for dispensing liquid reagent,
the assay device being such that a user manipulates the specimen collection tip through said specimen collection tip throughgoing aperture to smear bodily specimen on the specimen slide in an unused assay device, and thereafter said built-in liquid reagent dispensing arrangement is actuated for dispensing liquid reagent on the bodily specimen to react therewith and said specimen slide is elevated via said at least one throughgoing aperture in said cartridge housing bottom face from its initial lowermost specimen introduction position to its final uppermost specimen examination position thereby rendering a used assay device ready for examination of the bodily specimen.

2. The device according to claim 1 wherein said specimen slide includes at least one visually discernible target for enabling focusing thereon.

3. The device according to claim 1 and further comprising a specimen slide securing arrangement for securing the specimen slide in said final uppermost specimen examination position wherein said specimen slide securing arrangement enables an irreversible displacement from said initial lowermost specimen introduction position to said final uppermost specimen examination position.

4. The device according to claim 1 wherein said leading seal is highly visually distinguishable within said cartridge housing for enabling determination of its position thereaalong.

5. The device according to claim 1 wherein the assay device is pre-assembled with the handheld specimen collection tool, and said leading minor end face and said trailing minor end face each includes a central throughgoing aperture, such that the handheld specimen collection tool's specimen collection tip extends beyond said leading minor end face and the handheld specimen collection tool's handle extends beyond said trailing minor end face, and the assay device and the handheld specimen collection tool include a manual operated clamping arrangement for clamping them together in a pre-assembled state before use thereby precluding relative movement of the handheld specimen collection tool relative to the assay device.

6. The device according to claim 5 wherein said cartridge housing top face includes guidance members downward depending into said cartridge housing interior for guiding sliding withdrawal of the handheld specimen collection tool from the handheld assay device for smearing bodily specimen on said specimen slide.

7. The device according to claim 5 and further comprising a removable protective foil for protecting said leading minor end face and said cartridge housing top face, said protective foil being manually removal subsequent to sliding withdrawal of the handheld specimen collection tool from the assay device.

8. Assay apparatus for use with the handheld assay device according to claim 1 for diagnostic purposes of a bodily specimen, the assay apparatus comprises:
 (a) apparatus housing including:
  i) a tray having a tray pocket for snugly interchangeably receiving an assay device, and
  ii) a motorized arrangement for linear reciprocation of said tray between an outermost position relative to said apparatus housing for interchanging an assay device and an innermost position relative to said apparatus housing;
 (b) a plunger for insertion into an assay device's barrel for dispensing liquid reagent onto a bodily specimen;
 (c) a specimen slide elevation member for insertion through an assay device's underside throughgoing aperture for urging its specimen slide from its initial lowermost specimen introduction position to its final uppermost specimen examination position;
 (d) a digital image acquisition arrangement for obtaining digital images of at least a bodily specimen contained in an assay device;
 (e) a controller for controlling at least said motorized arrangement and said digital image acquisition arrangement; and
 (f) a stopcock actuator for rotating a stopcock from a closed position at said initial pre-liquid reagent dispensing position to an open position at said liquid reagent dispensing position for dispensing liquid reagent on an inward movement of said tray from said outermost position to said innermost position.

9. Apparatus according to claim 8 wherein an inward movement of said tray from said outermost position to said innermost position leads to insertion of said plunger into an assay device's barrel before said tray reaches said innermost position.

10. Apparatus according to claim 8 wherein an inward movement of said tray from said outermost position to said innermost position leads to insertion of said specimen slide elevation member through an assay device's underside throughgoing aperture for urging an assay device's specimen slide to its final uppermost specimen examination position before said tray reaches said innermost position.

11. Apparatus according to claim 8 wherein an inward movement of said tray from said outermost position to said innermost position leads to said digital image acquisition arrangement acquiring digital images of at least a bodily specimen contained in an assay device.

12. Apparatus according to claim 8 wherein said tray includes:
 i) an external tray member having said tray pocket,
 ii an internal tray member longitudinally slidingly reciprocal between an assay device insertion/ejection position of an assay device in said tray pocket at said outermost position and an actuated assay device position of an assay device in said tray pocket, and
 iii) a restraining mechanism for selectively restraining movement of said internal tray member relative to said external tray member.

13. Apparatus according to claim 12 wherein said internal tray member includes said plunger and a throughgoing slit, said external tray member includes a spring biased specimen slide elevation member, the arrangement being such that in said assay device insertion/ejection position, said plunger is not inserted in the assay device's barrel and said internal tray member blocks said spring biased specimen slide elevation member, and in said assay device actuated position, said plunger is inserted in the assay device's barrel and said spring biased specimen slide elevation member exits through said slit into the assay device's underside throughgoing aperture for urging its specimen slide from its initial lowermost specimen introduction position to its final uppermost specimen examination position.

14. Apparatus according to claim 8 wherein said digital image acquisition arrangement includes a single digital image camera having a first optical path for acquiring a first optical path image of a bodily specimen and a second optical path for acquiring a second optical path image of a bodily specimen wherein said digital image acquisition arrangement is operative to instantaneously acquire images along either said first optical path or said second optical path.

15. Apparatus according to claim 8 and further comprising a used assay device detector for determining whether an assay device newly inserted in said tray pocket is an unused assay device before the assay apparatus's operation for diagnostic purposes.

16. Apparatus according to claim 15 wherein said used assay device detector optically detects a position of a newly inserted assay device's seal compared to a benchmark position for an unused assay device for determining whether the newly inserted assay device is an unused assay device.

17. Apparatus according to claim 15 wherein said used assay device detector determines electric motor power consumption for initially displacing an assay device's leading seal compared to a benchmark electric motor power consumption for determining whether the newly inserted assay device is an unused assay device.

\* \* \* \* \*